US008772343B2

(12) United States Patent
Bell et al.

(10) Patent No.: US 8,772,343 B2
(45) Date of Patent: Jul. 8, 2014

(54) CHEMICAL COMPOUNDS

(75) Inventors: Andrew Simon Bell, Sandwich (GB); Alan Daniel Brown, Sandwich (GB); Russell Andrew Lewthwaite, Sandwich (GB); Manuel Perez-Pacheco, Sandwich (GB); David James Rawson, Sandwich (GB); Robert Ian Storer, Sandwich (GB); Nigel Alan Swain, Sandwich (GB)

(73) Assignee: Pfizer Limited, Sandwich (GB)

( * ) Notice: Subject to any disclaimer, the term of this patent is extended or adjusted under 35 U.S.C. 154(b) by 42 days.

(21) Appl. No.: 13/808,658

(22) PCT Filed: Jul. 6, 2011

(86) PCT No.: PCT/IB2011/052998
§ 371 (c)(1),
(2), (4) Date: Jan. 7, 2013

(87) PCT Pub. No.: WO2012/007877
PCT Pub. Date: Jan. 19, 2012

(65) Prior Publication Data
US 2013/0116285 A1    May 9, 2013

Related U.S. Application Data

(60) Provisional application No. 61/363,421, filed on Jul. 12, 2010, provisional application No. 61/491,540, filed on May 31, 2011.

(51) Int. Cl.
| A01N 41/06 | (2006.01) |
| A61K 31/18 | (2006.01) |
| C07C 303/00 | (2006.01) |
| C07C 307/00 | (2006.01) |
| C07C 309/00 | (2006.01) |
| C07C 311/00 | (2006.01) |

(52) U.S. Cl.
USPC ............................. 514/601; 564/80; 564/98

(58) Field of Classification Search
USPC ...................................... 514/601; 564/80, 98
See application file for complete search history.

(56) References Cited

U.S. PATENT DOCUMENTS

| 4,744,818 | A | 5/1988 | Heiba et al. |
| 5,543,279 | A | 8/1996 | Matsuda et al. |
| 5,565,429 | A | 10/1996 | Vincent et al. |
| 5,851,745 | A | 12/1998 | Takeuchi |
| 6,251,827 | B1 | 6/2001 | Ziemer et al. |
| 6,348,474 | B1 | 2/2002 | Kayakiri et al. |
| 6,376,512 | B1 | 4/2002 | Jayyosi et al. |
| 6,555,584 | B1 | 4/2003 | Ikawa et al. |
| 7,772,285 | B2 | 8/2010 | Chaki et al. |
| 8,314,240 | B2 | 11/2012 | Kubota et al. |
| 2002/0086887 | A1 | 7/2002 | Augeri et al. |
| 2008/0188467 | A1 | 8/2008 | Wong et al. |
| 2009/0143358 | A1 | 6/2009 | Marron et al. |
| 2010/0179137 | A1 | 7/2010 | Kamikubo et al. |
| 2010/0210660 | A1 | 8/2010 | Kremoser et al. |
| 2012/0010182 | A1 | 1/2012 | Brown et al. |
| 2012/0010183 | A1 | 1/2012 | Bell et al. |
| 2012/0010207 | A1 | 1/2012 | Bell et al. |
| 2013/0109667 | A1 | 5/2013 | Markworth et al. |
| 2013/0109696 | A1 | 5/2013 | Greener et al. |
| 2013/0109701 | A1 | 5/2013 | Brown et al. |
| 2013/0109708 | A1 | 5/2013 | Brown et al. |

FOREIGN PATENT DOCUMENTS

| EP | 0003416 | 8/1979 |
| EP | 0023100 | 1/1981 |
| EP | 0029742 | 6/1981 |
| EP | 0194599 | 9/1986 |
| EP | 0281103 | 9/1988 |
| EP | 0325245 | 7/1989 |
| EP | 0399732 | 11/1990 |
| EP | 0412848 | 2/1991 |
| EP | 0453210 | 10/1991 |
| EP | 0570006 | 11/1993 |
| EP | 0684521 | 11/1995 |
| EP | 0753508 | 1/1997 |
| GB | 2266527 | 11/1993 |
| WO | 8801133 | 2/1988 |
| WO | 8904303 | 5/1989 |
| WO | 8904304 | 5/1989 |
| WO | 8904305 | 5/1989 |
| WO | 8912628 | 12/1989 |
| WO | 9104964 | 4/1991 |
| WO | 9300332 | 1/1993 |
| WO | 9413636 | 6/1994 |
| WO | 9421590 | 9/1994 |

(Continued)

OTHER PUBLICATIONS

Naganawa et al., "Further optimization of sulfonamide analogs as EP1 receptor antagonists: Synthesis and evaluation of bioisosteres for the carboxylic acid group", Bioorganic & Medicinal Chemistry, vol. 14(21), pp. 7121-7137 (2006).

Pinkerton et al., "Allosteric potentiators of the metabotropic glutamate receptor 2 (mGlu2). Part 3: Identification and biological activity of indanone containing mGlu2 receptor potentiators", Bioorganic & Medicinal Chemistry Letters, vol. 15(6), pp. 1565-1571 (2005).

(Continued)

*Primary Examiner* — Sarah Pihonak
(74) *Attorney, Agent, or Firm* — J. Michael Dixon

(57) ABSTRACT

The invention relates to sulfonamide derivatives, to their use in medicine, to compositions containing them, to processes for their preparation and to intermediates used in such processes. More particularly the invention relates to a new sulfonamide Nav1.7 inhibitors of formula 10 (I):(I) or a pharmaceutically acceptable salt thereof, wherein Z, R1, R2, R3, R4 and R5 are as defined in the description. Nav1.7 inhibitors are potentially useful in the treatment of a wide range of disorders, particularly pain.

16 Claims, No Drawings

(56) References Cited

FOREIGN PATENT DOCUMENTS

| | | |
|---|---|---|
| WO | 9604905 | 2/1996 |
| WO | 9609818 | 4/1996 |
| WO | 9920275 | 4/1999 |
| WO | 9947508 | 9/1999 |
| WO | 0039077 | 7/2000 |
| WO | 0064876 | 11/2000 |
| WO | 0066120 | 11/2000 |
| WO | 0136365 | 5/2001 |
| WO | 0166098 | 9/2001 |
| WO | 0224636 | 3/2002 |
| WO | 2004018386 | 3/2004 |
| WO | 2005013914 | 2/2005 |
| WO | 2005080346 | 9/2005 |
| WO | 2005094810 | 10/2005 |
| WO | 2006015158 | 2/2006 |
| WO | 2006045514 | 5/2006 |
| WO | 2006121097 | 11/2006 |
| WO | 2007072782 | 6/2007 |
| WO | 2008025539 | 3/2008 |
| WO | 2008092231 | 8/2008 |
| WO | 2008118758 | 10/2008 |
| WO | 2009012242 | 1/2009 |
| WO | 2009049181 | 4/2009 |
| WO | 2009064250 | 5/2009 |
| WO | 2009064251 | 5/2009 |
| WO | 2009067541 | 5/2009 |
| WO | 2009067621 | 5/2009 |
| WO | 2009080835 | 7/2009 |
| WO | 2010079443 | 7/2010 |

OTHER PUBLICATIONS

Ng et al., "Design, Synthesis, and Biological Activity of Novel Factor Xa Inhibitors: 4-Aryloxy Substituents of 2,6-Diphenoxypyridines", Bioorganic & Medicinal Chemistry, vol. 10(3), pp. 657-666 (2002).

Hamill et al., "Development of [11C]L-159,884: A Radiolabelled, Nonpeptide Angiotensin II Antagonist that is Useful for Angiotensin II, AT1 Receptor Imaging", Applied Radiation and Isotopes, vol. 47(2), pp. 211-218 (1996).

Matassa et al., "Synthesis and in Vitro LTD4 Antagonist Activity of Bicyclic and Monocyclic Cyclopentylurethane and Cyclopentylacetamide N-Arylsulfonyl Amides", Journal of Medicinal Chemistry, vol. 33(9), pp. 2621-2629 (1990).

Musser et al., "N-[(Arylmethoxy)phenyl] Carboxylic Acids, Hydroxamic Acids, Tetrazoles, and Sulfonyl Carboxamides. Potent Orally Active Leukotriene D4 Antagonists of Novel Structure", Journal of Medicinal Chemistry, vol. 33(1), pp. 240-245 (1990).

Brown et al., "Hydroxyacetophenone-Derived Antagonists of the Peptidoleukotriens", Journal of Medicinal Chemistry, vol. 32(4), pp. 807-826 (1989).

Dubois et al., "Dihydrochalcone Sweeteners. A Study of the Atypical Temporal Phenomena", Journal of Medicinal Chemistry, vol. 24(4), pp. 408-428 (1981).

Silverman, Richard B. The Organic Chemistry of Drug Design and Drug Action. 2nd Ed., 2004, pp. 29-32, Elsevier, Burlington, MA.

CHEMICAL COMPOUNDS

CROSS REFERENCE

This application is the National Stage Application of International Patent Application No. PCT/IB2011/052998, filed Jul. 6, 2011, which claims priority to U.S. Provisional Patent Application No. 61/491,540, filed on May 31, 2011 and U.S Provisional Patent Application No. 61/363,421, filed on Jul. 12, 2010.

The invention relates to sulfonamide derivatives, to their use in medicine, to compositions containing them, to processes for their preparation and to intermediates used in such processes.

Voltage-gated sodium channels are found in all excitable cells including myocytes of muscle and neurons of the central and peripheral nervous system. In neuronal cells, sodium channels are primarily responsible for generating the rapid upstroke of the action potential. In this manner sodium channels are essential to the initiation and propagation of electrical signals in the nervous system. Proper and appropriate function of sodium channels is therefore necessary for normal function of the neuron. Consequently, aberrant sodium channel function is thought to underlie a variety of medical disorders (see Hubner C A, Jentsch T J, *Hum. Mol. Genet.*, 11(20): 2435-45 (2002) for a general review of inherited ion channel disorders) including epilepsy (Yogeeswari et al., *Curr. Drug Targets*, 5(7): 589-602 (2004)), arrhythmia (Noble D., *Proc. Natl. Acad. Sci. USA*, 99(9): 5755-6 (2002)) myotonia (Cannon, S C, *Kidney Int.* 57(3): 772-9 (2000)), and pain (Wood, J N et al., *J. Neurobiol.*, 61(1): 55-71 (2004)).

There are currently at least nine known members of the family of voltage-gated sodium channel (VGSC) alpha subunits. Names for this family include SCNx, SCNAx, and $Na_vx.x$. The VGSC family has been phylogenetically divided into two subfamilies $Na_v1.x$ (all but SCN6A) and $Na_v2.x$ (SCN6A). The Nav1.x subfamily can be functionally subdivided into two groups, those which are sensitive to blocking by tetrodotoxin (TTX-sensitive or TTX-s) and those which are resistant to blocking by tetrodotoxin (TTX-resistant or TTX-r).

The $Na_v1.7$ (PN1, SCN9A) VGSC is sensitive to blocking by tetrodotoxin and is preferentially expressed in peripheral sympathetic and sensory neurons. The SCN9A gene has been cloned from a number of species, including human, rat, and rabbit and shows ~90% amino acid identity between the human and rat genes (Toledo-Aral et al., *Proc. Natl. Acad. Sci. USA*, 94(4): 1527-1532 (1997)). An increasing body of evidence suggests that $Na_v1.7$ may play a key role in various pain states, including acute, inflammatory and/or neuropathic pain. Deletion of the SCN9A gene in nociceptive neurons of mice led to a reduction in mechanical and thermal pain thresholds and reduction or abolition of inflammatory pain responses (Nassar et al., *Proc Natl Acad Sci USA*, 101(34): 12706-11 (2004)). In humans, $Na_v1.7$ protein has been shown to accumulate in neuromas, particularly painful neuromas (Kretschmer et al., *Acta. Neurochir.* (*Wien*), 144(8): 803-10 (2002)). Gain of function mutations of $Na_v1.7$, both familial and sporadic, have been linked to primary erythermalgia, a disease characterized by burning pain and inflammation of the extremities (Yang et al., *J. Med. Genet.*, 41(3): 171-4 (2004), and paroxysmal extreme pain disorder (Waxman, S G *Neurology.* 7; 69(6): 505-7 (2007)). Congruent with this observation is the report that the non-selective sodium channel blockers lidocaine and mexiletine can provide symptomatic relief in cases of familial erythermalgia (Legroux-Crepel et al., *Ann. Dermatol Venereol.*, 130: 429-433) and carbamazepine is effective in reducing the number and severity of attacks in PEPD (Fertleman et al, *Neuron.;* 52(5):767-74 (2006). Further evidence of the role of Nav1.7 in pain is found in the phenotype of loss of function mutations of the SCN9A gene. Cox and colleagues (*Nature*, 444(7121):894-8 (2006)) were the first to report an association between loss-of-function mutations of SNC9A and congenital indifference to pain (CIP), a rare autosomal recessive disorder characterized by a complete indifference or insensitivity to painful stimuli. Subsequent studies have revealed a number of different mutations that result in a loss of function of the SCN9A gene and the CIP phenotype (Goldberg et al, *Clin Genet.;* 71(4): 311-9 (2007), Ahmad et al, *Hum Mol. Genet.* 1; 16(17): 2114-21 (2007)).

Nav 1.7 inhibitors are therefore potentially useful in the treatment of a wide range of disorders, particularly pain, including: acute pain; chronic pain; neuropathic pain; inflammatory pain; visceral pain; nociceptive pain including post-surgical pain; and mixed pain types involving the viscera, gastrointestinal tract, cranial structures, musculoskeletal system, spine, urogenital system, cardiovascular system and CNS, including cancer pain, back and orofacial pain.

Certain inhibitors of voltage gated sodium channels useful in the treatment of pain are known. Thus WO-A-2005/013914 discloses heteroarylamino sulfonylphenyl derivatives, WO-A-2008/118758 aryl sulphonamides and WO-A-2009/012242 N-thiazolyl benzenesulfonamides.

There is, however, an ongoing need to provide new $Na_v1.7$ inhibitors that are good drug candidates.

Preferably compounds are selective Nav1.7 channel inhibitors. That is, preferred compounds show an affinity for the Nav1.7 channel over other Nav channels. In particular, they should show an affinity for the Nav1.7 channel which is greater than their affinity for Nav1.5 channels. Advantageously, compounds should show little or no affinity for the Nav1.5 channel.

Selectivity for the Nav1.7 channel over Nav1.5 may potentially lead to one or more improvements in side-effect profile. Without wishing to be bound by theory, such selectivity is thought to reduce any cardiovascular side effects which may be associated with affinity for the Nav1.5 channel. Preferably compounds demonstrate a selectivity of 10-fold, more preferably 30-fold, most preferably 100-fold, for the Nav 1.7 channel when compared to their selectivity for the Nav1.5 channel whilst maintaining good potency for the Nav1.7 channel.

Furthermore, preferred compounds should have one or more of the following properties: be well absorbed from the gastrointestinal tract; be metabolically stable; have a good metabolic profile, in particular with respect to the toxicity or allergenicity of any metabolites formed; or possess favourable pharmacokinetic properties whilst still retaining their activity profile as Nav1.7 channel inhibitors. They should be non-toxic and demonstrate few side-effects. Ideal drug candidates should exist in a physical form that is stable, non-hygroscopic and easily formulated.

We have now found new sulphonamide Nav1.7 inhibitors.

According to a first aspect of the invention there is provided a compound of formula (I)

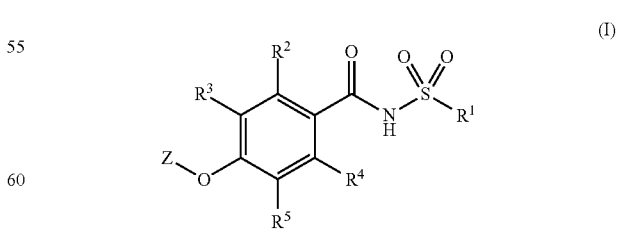

or a pharmaceutically acceptable salt thereof, wherein:
Z is a group selected from naphthyl, phenyl and $Het^1$, said group being optionally independently substituted by one to three substituents selected from $Y^1$ and $Y^2$;

Y¹ and Y² are independently selected from F; Cl; CN; (C₁-C₈)alkyl, optionally substituted by (C₃-C₈)cycloalkyl or one to three F; (C₃-C₈)cycloalkyl, optionally substituted by one to three F; NR⁷R⁸; (C₁-C₈)alkyloxy, optionally independently substituted by one to three R⁹; (C₃-C₈)cycloalkyloxy; phenyl, optionally independently substituted by one to three R¹⁰; Het² and Het³; wherein (C₃-C₈)cycloalkyloxy may be optionally fused to a phenyl ring or may be independently substituted by one to three R¹⁰;

R¹ is (C₁-C₆)alkyl or (C₃-C₈)cycloalkyl, each of which is optionally substituted by one to three F;

R², R³, R⁴ are independently H, F, Cl or —OCH₃;

R⁵ is phenyl optionally substituted by one to three substituents independently selected from CN, Cl, F and R⁶; or Het³;

R⁶ is a group selected from (C₁-C₆)alkyl and (C₁-C₆)alkyloxy, wherein each group is optionally substituted, valency permitting, by one to five F;

R⁷ and R⁸ are independently H; (C₁-C₈)alkyl, optionally independently substituted by one to three R¹¹; (C₃-C₈) cycloalkyl; or 'C-linked' Het²; wherein (C₃-C₈)cycloalkyl may be optionally fused to a phenyl ring or may be independently substituted by one to three R¹⁰; or R⁷ and R⁸, taken together with the nitrogen atom to which they are attached, form a saturated, bridged, 7- to 9-membered ring;

R⁹ is F; (C₁-C₆)alkyloxy; (C₃-C₈)cycloalkyl, optionally substituted by one to three F; Het¹; or phenyl, optionally independently substituted by one to three R⁶;

R¹⁰ is F, Cl or R⁶;

R¹¹ is F; (C₁-C₆)alkyloxy; (C₃-C₈)cycloalkyl, optionally substituted by one to three F; 'C-linked' Het¹; or phenyl, optionally independently substituted by one to three R⁶;

Het¹ is a 6-, 9- or 10-membered heteroaryl comprising one to three nitrogen atoms;

Het² is a 3- to 8-membered saturated monoheterocycloalkyl comprising one or two ring members selected from —NR¹²— and —O—, said monoheterocycloalkyl being optionally substituted on a ring carbon atom by one to three substituents independently selected from F, (C₁-C₆)alkyl, (C₁-C₄)alkyloxy(C₀-C₄)alkylene and (C₃-C₈)cycloalkyl;

Het³ is a 5- or 6-membered heteroaryl comprising one to three nitrogen atoms, said heteroaryl being optionally substituted by one to three substituents selected from F, Cl, CN and R⁶; and R¹² is H, (C₁-C₆)alkyl or (C₃-C₈)cycloalkyl, wherein (C₁-C₆) alkyl and (C₃-C₈)cycloalkyl are optionally substituted by one to three F; or, when Het² is 'N-linked', is absent.

Described below are a number of embodiments (E) of this first aspect of the invention, where for convenience E1 is identical thereto.

E1 A compound of formula (I) as defined above or a pharmaceutically acceptable salt thereof.

E2 A compound according to E1 wherein Z is phenyl optionally independently substituted by one to three substituents selected from Y¹ and Y².

E3 A compound according to either of E1 or E2 wherein Z is phenyl optionally independently substituted by one or two substituents selected from Y¹ and Y².

E4 A compound according to any of E1 to E3 wherein Z is phenyl para-substituted by Y².

E5 A compound according to E1 wherein Z is a 6-membered heteroaryl comprising one to three nitrogen atoms, said heteroaryl being optionally independently substituted by one to three substituents selected from Y¹ and Y².

E6 A compound according to either of E1 or E5 wherein Z is pyridyl optionally independently substituted by one to three substituents selected from Y¹ and Y².

E7 A compound according to any of E1, E5 or E6 wherein Z is pyridyl optionally independently substituted by one or two substituents selected from Y¹ and Y².

E8 A compound according to any of E1 or E5 to E7 wherein Z is pyridyl optionally independently substituted by one or two substituents selected from Y¹ and Y² and wherein said pyridyl is orientated as below:

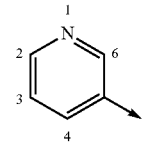

E9 A compound according to E8 wherein said pyridyl is 2-substituted or, where di-substituted, 2- and 3-substituted.

E10 A compound according to any of E1 to E9 wherein R¹ is (C₁-C₄)alkyl or (C₃-C₆)cycloalkyl.

E11 A compound according to any of E1 to E10 wherein R¹ is (C₁-C₃)alkyl or (C₃-C₄)cycloalkyl.

E12 A compound according to any of E1 to E11 wherein R¹ is methyl or cyclopropyl.

E13 A compound according to any of E1 to E12 wherein R², R³ and R⁴ are independently H or F.

E14 A compound according to any of E1 to E13 wherein R² is H or F; and R³ and R⁴ are both H.

E15 A compound according to any of E1 to E14 wherein R⁵ is (i) phenyl optionally substituted by one or two substituents independently selected from CN, Cl, F and R⁶; or (ii) a 5- or 6-membered heteroaryl comprising one or two nitrogen atoms, said heteroaryl being optionally substituted by one or two substituents selected from F, Cl, CN and R⁶.

E16 A compound according to any of E1 to E15 wherein R⁵ is (i) phenyl optionally substituted by CN, Cl, F or R⁶; or (ii) a heteroaryl selected from pyrazolyl, pyridyl or pyrimidinyl, said heteroaryl being optionally substituted by (C₁-C₆)alkyloxy or (C₁-C₆)alkyloxy substituted, valency permitting, by one to five F.

E17 A compound according to any of E1 to E18 wherein R⁶ is a group selected from (C₁-C₄)alkyl and (C₁-C₄)alkyloxy, wherein each group is optionally substituted, valency permitting, by one to five F.

E18 A compound according to any of E1 to E17 wherein R⁶ is a group selected from CH₃, C₂H₅, CF₃, —OCH₃, —OC₂H₅ or —OCF₃.

E19 A compound according to E1 selected from:
4-(4-chloro-2-methoxyphenoxy)-3-(2-methoxypyridin-3-yl)-N-(methylsulfonyl)benzamide;
4-[(6-isobutoxypyridin-3-yl)oxy]-3-(2-methoxypyridin-3-yl)-N-(methylsulfonyl)benzamide;
Examples 3 to 94; and
4-(4-chloro-3-ethylphenoxy)-N-(methylsulfonyl)-3-(1H-pyrazol-5-yl)benzamide;
or a pharmaceutically acceptable salt thereof.

Alkyl, alkylene, and alkoxy groups, containing the requisite number of carbon atoms, can be unbranched or branched. Examples of alkyl include methyl, ethyl, n-propyl, i-propyl, n-butyl, i-butyl, sec-butyl and t-butyl. Examples of alkoxy include methoxy, ethoxy, n-propoxy, i-propoxy, n-butoxy, i-butoxy, sec-butoxy and t-butoxy. Examples of alkylene include methylene, 1,1-ethylene, 1,2-ethylene, 1,1-propylene, 1,2-propylene, 1,3-propylene and 2,2-propylene.

Examples of cycloalkyl include cyclopropyl, cyclobutyl, cyclopentyl, cyclohexyl, cycloheptyl and cyclooctyl.

Halo means fluoro, chloro, bromo or iodo.

The term 'C-linked' used in the definitions of formula (I) means that the group in question is joined via a ring carbon. The term 'N-linked' used in the definitions of formula (I) means that the group in question is joined via a ring nitrogen.

Specific examples of 5- or 6-membered heteroaryl used in the definitions of formula (I) include pyrrolyl, pyrazolyl, imidazoyl, thiazolyl, isothiazolyl, thiadiazolyl, pyridyl, pyridazinyl, pyrimidinyl and pyrazinyl. Except as expressly defined above, when such heteroaryls are substituted, the substituent may be located on a ring carbon (in all cases) or a ring nitrogen with appropriate valency (if the substituent is joined through a carbon atom).

Specific examples of 9- or 10-membered heteroaryl used in the definitions of formula (I) include indolyl, benzimidazolyl, indazolyl, benzotriazolyl, pyrrolo[2,3-b]pyridyl, pyrrolo[2,3-c]pyridyl, pyrrolo[3,2-c]pyridyl, pyrrolo[3,2-b]pyridyl, imidazo[4,5-b]pyridyl, imidazo[4,5-c]pyridyl, pyrazolo[4,3-d]pyridyl, pyrazolo[4,3-c]pyridyl, pyrazolo[3,4-c]pyridyl, pyrazolo[3,4-b]pyridyl, isoindolyl, indazolyl, purinyl, indolizinyl, imidazo[1,2-a]pyridyl, imidazo[1,5-a]pyridyl, pyrazolo[1,5-a]pyridyl, pyrrolo[1,2-b]pyridazinyl, imidazo[1,2-c]pyrimidinyl, quinolinyl, isoquinolinyl, cinnolinyl, quinazolinyl, quinoxalinyl, phthalazinyl, 1,6-naphthyridinyl, 1,7-naphthyridinyl, 1,8-naphthyridinyl, 1,5-naphthyridinyl, 2,6-naphthyridinyl, 2,7-naphthyridinyl, pyrido[3,2-d]pyrimidinyl, pyrido[4,3-d]pyrimidinyl, pyrido[3,4-d]pyrimidinyl, pyrido[2,3-d]pyrimidinyl, pyrido[2,3-d]pyrazinyl and pyrido[3,4-b]pyrazinyl. Except as expressly defined above, when such heteroaryls are substituted, the substituent may be located on a ring carbon (in all cases) or a ring nitrogen with appropriate valency (if the substituent is joined through a carbon atom).

Specific examples of Het[1] include oxiranyl, aziridinyl, oxetanyl, azetidinyl, tetrahydrofuranyl, pyrrolidinyl, tetrahydropyranyl, piperidinyl, morpholinyl, piperazinyl, azepanyl, oxepanyl, oxazepanyl and diazepinyl.

Hereinafter, all references to compounds of the invention include compounds of formula (I) or pharmaceutically acceptable salts, solvates, or multi-component complexes thereof, or pharmaceutically acceptable solvates or multi-component complexes of pharmaceutically acceptable salts of compounds of formula (I), as discussed in more detail below.

Preferred compounds of the invention are compounds of formula (I) or pharmaceutically acceptable salts thereof.

Suitable acid addition salts are formed from acids which form non-toxic salts. Examples include the acetate, adipate, aspartate, benzoate, besylate, bicarbonate/carbonate, bisulphate/sulphate, borate, camsylate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, pyroglutamate, saccharate, stearate, succinate, tannate, tartrate, tosylate, trifluoroacetate and xinofoate salts.

Suitable base salts are formed from bases which form non-toxic salts. Examples include the aluminium, arginine, benzathine, calcium, choline, diethylamine, diolamine, glycine, lysine, magnesium, meglumine, olamine, potassium, sodium, tromethamine and zinc salts.

Hemisalts of acids and bases may also be formed, for example, hemisulphate and hemicalcium salts.

The skilled person will appreciate that the aforementioned salts include ones wherein the counterion is optically active, for example d-lactate or l-lysine, or racemic, for example dl-tartrate or dl-arginine.

For a review on suitable salts, see "Handbook of Pharmaceutical Salts: Properties, Selection, and Use" by Stahl and Wermuth (Wiley-VCH, Weinheim, Germany, 2002).

Pharmaceutically acceptable salts of compounds of formula (I) may be prepared by one or more of three methods:
(i) by reacting the compound of formula (I) with the desired acid or base;
(ii) by removing an acid- or base-labile protecting group from a suitable precursor of the compound of formula (I) using the desired acid or base; or
(iii) by converting one salt of the compound of formula (I) to another by reaction with an appropriate acid or base or by means of a suitable ion exchange column.

All three reactions are typically carried out in solution. The resulting salt may precipitate out and be collected by filtration or may be recovered by evaporation of the solvent. The degree of ionisation in the resulting salt may vary from completely ionised to almost non-ionised.

The compounds of formula (I) or pharmaceutically acceptable salts thereof may exist in both unsolvated and solvated forms. The term 'solvate' is used herein to describe a molecular complex comprising a compound of formula (I) or a pharmaceutically acceptable salt thereof and one or more pharmaceutically acceptable solvent molecules, for example, ethanol. The term 'hydrate' is employed when said solvent is water. Pharmaceutically acceptable solvates in accordance with the invention include those wherein the solvent of crystallization may be isotopically substituted, e.g. $D_2O$, $d_6$-acetone and $d_6$-DMSO.

A currently accepted classification system for organic hydrates is one that defines isolated site, channel, or metal-ion coordinated hydrates—see *Polymorphism in Pharmaceutical Solids* by K. R. Morris (Ed. H. G. Brittain, Marcel Dekker, 1995), incorporated herein by reference. Isolated site hydrates are ones in which the water molecules are isolated from direct contact with each other by intervening organic molecules. In channel hydrates, the water molecules lie in lattice channels where they are next to other water molecules. In metal-ion coordinated hydrates, the water molecules are bonded to the metal ion.

When the solvent or water is tightly bound, the complex will have a well-defined stoichiometry independent of humidity. When, however, the solvent or water is weakly bound, as in channel solvates and hygroscopic compounds, the water/solvent content will be dependent on humidity and drying conditions. In such cases, non-stoichiometry will be the norm.

The compounds of the invention may exist in a continuum of solid states ranging from fully amorphous to fully crystalline. The term 'amorphous' refers to a state in which the material lacks long range order at the molecular level and, depending upon temperature, may exhibit the physical properties of a solid or a liquid. Typically such materials do not give distinctive X-ray diffraction patterns and, while exhibiting the properties of a solid, are more formally described as a liquid. Upon heating, a change from solid to liquid properties occurs which is characterised by a change of state, typically second order ('glass transition'). The term 'crystalline' refers to a solid phase in which the material has a regular ordered internal structure at the molecular level and gives a distinctive X-ray diffraction pattern with defined peaks. Such materials when heated sufficiently will also exhibit the properties of a liquid, but the change from solid to liquid is characterised by a phase change, typically first order ('melting point').

Also included within the scope of the invention are multi-component complexes (other than salts and solvates) of compounds of formula (I) or pharmaceutically acceptable salts thereof wherein the drug and at least one other component are present in stoichiometric or non-stoichiometric amounts. Complexes of this type include clathrates (drug-host inclusion complexes) and co-crystals. The latter are typically defined as crystalline complexes of neutral molecular constituents which are bound together through non-covalent interactions, but could also be a complex of a neutral molecule with a salt. Co-crystals may be prepared by melt crystallisation, by recrystallisation from solvents, or by physically grinding the components together—see Chem Commun, 17, 1889-1896, by O. Almarsson and M. J. Zaworotko (2004), incorporated herein by reference. For a general review of multi-component complexes, see J Pharm Sci, 64 (8), 1269-1288, by Haleblian (August 1975), incorporated herein by reference.

The compounds of the invention may also exist in a mesomorphic state (mesophase or liquid crystal) when subjected to suitable conditions. The mesomorphic state is intermediate between the true crystalline state and the true liquid state (either melt or solution). Mesomorphism arising as the result of a change in temperature is described as 'thermotropic' and that resulting from the addition of a second component, such as water or another solvent, is described as 'lyotropic'. Compounds that have the potential to form lyotropic mesophases are described as 'amphiphilic' and consist of molecules which possess an ionic (such as —$COO^-Na^+$, —$COO^-K^+$, or —$SO_3^-Na^+$) or non-ionic (such as —$N^-N^+(CH_3)_3$) polar head group. For more information, see *Crystals and the Polarizing Microscope* by N. H. Hartshorne and A. Stuart, 4$^{th}$ Edition (Edward Arnold, 1970), incorporated herein by reference.

The compounds of the invention may be administered as prodrugs. Thus certain derivatives of compounds of formula (I) which may have little or no pharmacological activity themselves can, when administered into or onto the body, be converted into compounds of formula (I) having the desired activity, for example, by hydrolytic cleavage. Such derivatives are referred to as 'prodrugs'. Further information on the use of prodrugs may be found in 'Pro-drugs as Novel Delivery Systems, Vol. 14, ACS Symposium Series (T Higuchi and W Stella) and 'Bioreversible Carriers in Drug Design', Pergamon Press, 1987 (ed. E B Roche, American Pharmaceutical Association).

Prodrugs can, for example, be produced by replacing appropriate functionalities present in a compound of formula (I) with certain moieties known to those skilled in the art as 'pro-moieties' as described, for example, in "Design of Prodrugs" by H Bundgaard (Elsevier, 1985).

Examples of prodrugs include phosphate prodrugs, such as dihydrogen or dialkyl (e.g. di-tert-butyl) phosphate prodrugs. Further examples of replacement groups in accordance with the foregoing examples and examples of other prodrug types may be found in the aforementioned references.

Also included within the scope of the invention are metabolites of compounds of formula (I), that is, compounds formed in vivo upon administration of the drug. Some examples of metabolites in accordance with the invention include, where the compound of formula (I) contains a phenyl (Ph) moiety, a phenol derivative thereof (-Ph>-PhOH);

Compounds of the invention containing one or more asymmetric carbon atoms can exist as two or more stereoisomers. Included within the scope of the invention are all stereoisomers of the compounds of the invention and mixtures of one or more thereof.

Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC).

Alternatively, the racemate (or a racemic precursor) may be reacted with a suitable optically active compound, for example, an alcohol, or, in the case where the compound of formula (I) contains an acidic or basic moiety, a base or acid such as 1-phenylethylamine or tartaric acid. The resulting diastereomeric mixture may be separated by chromatography and/or fractional crystallization and one or both of the diastereoisomers converted to the corresponding pure enantiomer(s) by means well known to a skilled person.

Chiral compounds of the invention (and chiral precursors thereof) may be obtained in enantiomerically-enriched form using chromatography, typically HPLC, on an asymmetric resin with a mobile phase consisting of a hydrocarbon, typically heptane or hexane, containing from 0 to 50% by volume of isopropanol, typically from 2% to 20%, and from 0 to 5% by volume of an alkylamine, typically 0.1% diethylamine. Concentration of the eluate affords the enriched mixture.

Mixtures of stereoisomers may be separated by conventional techniques known to those skilled in the art; see, for example, "Stereochemistry of Organic Compounds" by E. L. Eliel and S. H. Wilen (Wiley, New York, 1994.

The scope of the invention includes all crystal forms of the compounds of the invention, including racemates and racemic mixtures (conglomerates) thereof. Stereoisomeric conglomerates may also be separated by the conventional techniques described herein just above.

The scope of the invention includes all pharmaceutically acceptable isotopically-labelled compounds of the invention wherein one or more atoms are replaced by atoms having the same atomic number, but an atomic mass or mass number different from the atomic mass or mass number which predominates in nature.

Examples of isotopes suitable for inclusion in the compounds of the invention include isotopes of hydrogen, such as $^2H$ and $^3H$, carbon, such as $^{11}C$, $^{13}C$ and $^{14}C$, chlorine, such as $^{36}Cl$, fluorine, such as $^{18}F$, iodine, such as $^{123}I$ and $^{125}I$, nitrogen, such as $^{13}N$ and $^{15}N$, oxygen, such as $^{15}O$, $^{17}O$ and $^{18}O$, phosphorus, such as $^{32}P$, and sulphur, such as $^{35}S$.

Certain isotopically-labelled compounds of the invention, for example, those incorporating a radioactive isotope, are useful in drug and/or substrate tissue distribution studies. The radioactive isotopes tritium, i.e. $^3H$, and carbon-14, i.e. $^{14}C$, are particularly useful for this purpose in view of their ease of incorporation and ready means of detection. Substitution with heavier isotopes such as deuterium, i.e. $^2H$, may afford certain therapeutic advantages resulting from greater metabolic stability, for example, increased in vivo half-life or reduced dosage requirements, and hence may be preferred in some circumstances. Substitution with positron emitting isotopes, such as $^{11}C$, $^{18}F$, $^{15}O$ and $^{13}N$, can be useful in Positron Emission Topography (PET) studies for examining substrate receptor occupancy.

Isotopically-labeled compounds of formula (I) can generally be prepared by conventional techniques known to those skilled in the art or by processes analogous to those described in the accompanying Examples and Preparations using an appropriate isotopically-labeled reagent in place of the non-labeled reagent previously employed.

Also within the scope of the invention are intermediate compounds as hereinafter defined, all salts, solvates and complexes thereof and all solvates and complexes of salts thereof as defined hereinbefore for compounds of formula (I). The invention includes all polymorphs of the aforementioned species and crystal habits thereof.

When preparing a compound of formula (I) in accordance with the invention, a person skilled in the art may routinely select the form of intermediate which provides the best combination of features for this purpose. Such features include the melting point, solubility, processability and yield of the intermediate form and the resulting ease with which the product may be purified on isolation.

The compounds of the invention may be prepared by any method known in the art for the preparation of compounds of analogous structure. In particular, the compounds of the invention can be prepared by the procedures described by reference to the Schemes that follow, or by the specific methods described in the Examples, or by similar processes to either.

lar, it may be necessary or desirable to protect amino or carboxylic acid groups. The protecting groups used in the preparation of the compounds of the invention may be used in conventional manner. See, for example, those described in 'Greene's Protective Groups in Organic Synthesis' by Theodora W Greene and Peter G M Wuts, third edition, (John Wiley and Sons, 1999), in particular chapters 7 ("Protection for the Amino Group") and 5 ("Protection for the Carboxyl Group"), incorporated herein by reference, which also describes methods for the removal of such groups.

In the following general methods, Z is $R^1$, $R^2$, $R^3$, $R^4$ and $R^5$ are as previously defined for a derivative of the formula (I) unless otherwise stated. Pg is a suitable carboxylic acid ester protecting group tent butyl, methyl, ethyl, or tolyl. W is —$CO_2$Pg or CN. M is an optionally substituted/ligated metal or boron group suitable for cross coupling reactions, such as trialkylstannane, dihydroxyborane, dialkoxyborane or halozinc. —V is OH or $NH_2$.

Where ratios of solvents are given, the ratios are by volume.

According to a first process, compounds of formula (I) may be prepared by the process illustrated in Scheme 1.

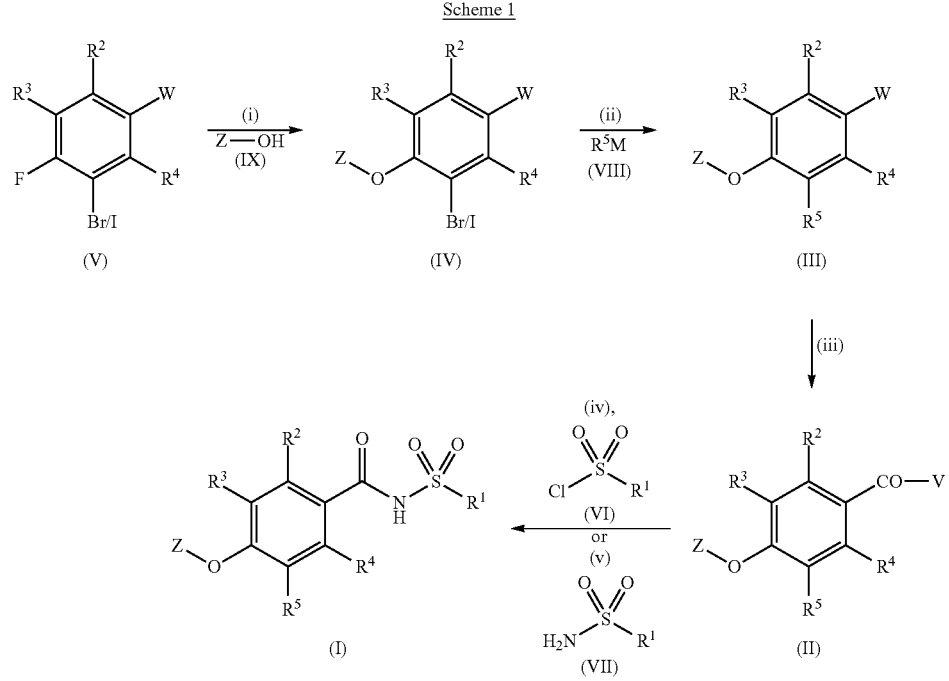

The skilled person will appreciate that the experimental conditions set forth in the schemes that follow are illustrative of suitable conditions for effecting the transformations shown, and that it may be necessary or desirable to vary the precise conditions employed for the preparation of compounds of formula (I). It will be further appreciated that it may be necessary or desirable to carry out the transformations in a different order from that described in the schemes, or to modify one or more of the transformations, to provide the desired compound of the invention.

In addition, the skilled person will appreciate that it may be necessary or desirable at any stage in the synthesis of compounds of the invention to protect one or more sensitive groups, so as to prevent undesirable side reactions. In particu- Compounds of formula (I) can be prepared from compounds of formula (II) (—V=$NH_2$) according to reaction step (iv) by displacement of a sulfonyl chloride of formula (VI) under basic reaction conditions. Typical conditions comprise lithium hexamethyldisilazane in THF at −78° C.

Alternatively compounds of formula (I) can be prepared from compounds of formulae (II) (—V=OH) according to reaction step (v) by activation of the acid group with reagents such as oxalyl chloride, carbonyl di-imidazole (CDI), a uronium based peptide coupling agent, propylphosphonic anhydride or a carbodiimide reagent followed by displacement with a suitable sulfonamide of formula (VII) in the presence of a nucleophilic base such as 4-dimethylaminopyridine.

Typical conditions comprise N,N-dimethylaminopropyl-N'-ethylcarbodiimide and 4-dimethylaminopyridine in DCM with methanesulfonamide.

Compounds of formula (II) can be prepared by hydrolysis of the nitrile functional group in compounds of formula (III, W=nitrile) by either acidic or basic methods according to step (iii). Preferred conditions are potassium carbonate in aqueous 30% hydrogen peroxide and DMSO.

Compounds of formula (II) can also be prepared by hydrolysis of the ester functional group in compounds of formula (III, W=—CO$_2$Pg) under basic or acidic conditions according to step (iii). Preferred conditions are lithium hydroxide in MeOH at room temperature.

Compounds of formula (III) can be prepared from compounds of formula (IV) by palladium-catalysed coupling of a compound of formula (VIII) according to step (ii). Conveniently the coupling is effected with a boronic acid or ester of formula (VIII). The coupling reaction can be carried out with a variety of palladium catalysts such as palladium acetate and tetrakistriphenylphosphine palladium (0) in various solvents such as 1,4-dioxan, ethanol, toluene and dimethoxyethane and in the presence of bases such as sodium and potassium carbonate, cesium fluoride and potassium phosphate. The temperature of the reaction can be between room temperature and 120° C. Preferably the coupling is effected with a boronic acid or ester of formula (VIII) in the presence of tetrakistriphenylphosphine palladium (0) and sodium carbonate in 1,4-dioxan and water, and at 100° C.

Compounds of formula (IV) can be made from compounds of formula (V) by a nucleophilic aromatic substitution reaction (SNAr) using an alcohol of formula (IX) and base according to step (i). Conveniently the reaction is effected in the presence of a solvent. Suitable reaction conditions include potassium carbonate in DMF or DMSO, sodium hydride in NMP or DMF, sodium hydroxide or potassium hydroxide in 1,4-dioxane and water or DMSO or potassium tert-butoxide in THF at room temperature to 150° C. Preferred conditions comprise 2 equivalents of potassium carbonate in DMF at 90° C.

As noted hereinabove, it may be desirable to carry out the transformations shown in Scheme 1 in a different order from that described in the schemes, or to modify one or more of the transformations, to provide the desired compound of the invention. Thus compounds of formula (I) can also be made from compounds of formula (V) by an alteration of the order of steps (i) and (ii). The palladium-catalysed coupling of a variety of boronic acids and esters can be performed on compounds of formula (V) as outlined above and then the nucleophilic aromatic substitution of the fluoro group can then be performed as outlined above. This alternate route would yield compounds of formula (III) which can be progressed as already outlined in steps (iii) and (iv) in Scheme 1.

Compounds of formulae (V), (VI), (VII), (VIII) and (IX) are either commercially available, known from the literature, easily prepared by methods well known to those skilled in the art, or can be made according to preparations described herein.

All new processes for preparing compounds of formula (I), and corresponding new intermediates employed in such processes, form further aspects of the present invention.

Compounds of the invention intended for pharmaceutical use may be administered as crystalline or amorphous products or may exist in a continuum of solid states ranging from fully amorphous to fully crystalline. They may be obtained, for example, as solid plugs, powders, or films by methods such as precipitation, crystallization, freeze drying, spray drying, or evaporative drying. Microwave or radio frequency drying may be used for this purpose.

They may be administered alone or in combination with one or more other compounds of the invention or in combination with one or more other drugs (or as any combination thereof). Generally, they will be administered as a formulation in association with one or more pharmaceutically acceptable excipients. The term 'excipient' is used herein to describe any ingredient other than the compound(s) of the invention. The choice of excipient will to a large extent depend on factors such as the particular mode of administration, the effect of the excipient on solubility and stability, and the nature of the dosage form.

In another aspect the invention provides a pharmaceutical composition comprising a compound of the invention together with one or more pharmaceutically acceptable excipients.

Pharmaceutical compositions suitable for the delivery of compounds of the present invention and methods for their preparation will be readily apparent to those skilled in the art. Such compositions and methods for their preparation may be found, for example, in "Remington's Pharmaceutical Sciences", 19th Edition (Mack Publishing Company, 1995).

Suitable modes of administration include oral, parenteral, topical, inhaled/intranasal, rectal/intravaginal, and ocular/aural administration.

Formulations suitable for the aforementioned modes of administration may be formulated to be immediate and/or modified release. Modified release formulations include delayed-, sustained-, pulsed-, controlled-, targeted and programmed release.

The compounds of the invention may be administered orally. Oral administration may involve swallowing, so that the compound enters the gastrointestinal tract, or buccal or sublingual administration may be employed by which the compound enters the blood stream directly from the mouth. Formulations suitable for oral administration include solid formulations such as tablets, capsules containing particulates, liquids, or powders, lozenges (including liquid-filled), chews, multi- and nano-particulates, gels, solid solution, liposome, films, ovules, sprays, liquid formulations and buccal/mucoadhesive patches.

Liquid formulations include suspensions, solutions, syrups and elixirs. Such formulations may be employed as fillers in soft or hard capsules and typically comprise a carrier, for example, water, ethanol, polyethylene glycol, propylene glycol, methylcellulose, or a suitable oil, and one or more emulsifying agents and/or suspending agents. Liquid formulations may also be prepared by the reconstitution of a solid, for example, from a sachet.

The compounds of the invention may also be used in fast-dissolving, fast-disintegrating dosage forms such as those described in Expert Opinion in Therapeutic Patents, 11 (6), 981-986, by Liang and Chen (2001).

For tablet dosage forms, depending on dose, the drug may make up from 1 weight % to 80 weight % of the dosage form, more typically from 5 weight % to 60 weight % of the dosage form. In addition to the drug, tablets generally contain a disintegrant. Examples of disintegrants include sodium starch glycolate, sodium carboxymethyl cellulose, calcium carboxymethyl cellulose, croscarmellose sodium, crospovidone, polyvinylpyrrolidone, methyl cellulose, microcrystalline cellulose, lower alkyl-substituted hydroxypropyl cellulose, starch, pregelatinised starch and sodium alginate. Generally, the disintegrant will comprise from 1 weight % to 25 weight %, preferably from 5 weight % to 20 weight % of the dosage form.

Binders are generally used to impart cohesive qualities to a tablet formulation. Suitable binders include microcrystalline cellulose, gelatin, sugars, polyethylene glycol, natural and synthetic gums, polyvinylpyrrolidone, pregelatinised starch, hydroxypropyl cellulose and hydroxypropyl methylcellulose. Tablets may also contain diluents, such as lactose (monohydrate, spray-dried monohydrate, anhydrous and the like), mannitol, xylitol, dextrose, sucrose, sorbitol, microcrystalline cellulose, starch and dibasic calcium phosphate dihydrate.

Tablets may also optionally comprise surface active agents, such as sodium lauryl sulfate and polysorbate 80, and glidants such as silicon dioxide and talc. When present, surface active agents may comprise from 0.2 weight % to 5 weight % of the tablet, and glidants may comprise from 0.2 weight % to 1 weight % of the tablet.

Tablets also generally contain lubricants such as magnesium stearate, calcium stearate, zinc stearate, sodium stearyl fumarate, and mixtures of magnesium stearate with sodium lauryl sulphate. Lubricants generally comprise from 0.25 weight % to 10 weight %, preferably from 0.5 weight % to 3 weight % of the tablet. Other possible ingredients include anti-oxidants, colourants, flavouring agents, preservatives and taste-masking agents.

Exemplary tablets contain up to about 80% drug, from about 10 weight % to about 90 weight % binder, from about 0 weight % to about 85 weight % diluent, from about 2 weight % to about 10 weight % disintegrant, and from about 0.25 weight % to about 10 weight % lubricant. Tablet blends may be compressed directly or by roller to form tablets. Tablet blends or portions of blends may alternatively be wet-, dry-, or melt-granulated, melt congealed, or extruded before tabletting. The final formulation may comprise one or more layers and may be coated or uncoated; it may even be encapsulated. The formulation of tablets is discussed in "Pharmaceutical Dosage Forms: Tablets", Vol. 1, by H. Lieberman and L. Lachman (Marcel Dekker, New York, 1980).

Suitable modified release formulations for the purposes of the invention are described in U.S. Pat. No. 6,106,864. Details of other suitable release technologies such as high energy dispersions and osmotic and coated particles are to be found in "Pharmaceutical Technology On-line", 25(2), 1-14, by Verma et al (2001). The use of chewing gum to achieve controlled release is described in WO 00/35298.

The compounds of the invention may also be administered directly into the blood stream, into muscle, or into an internal organ. Suitable means for parenteral administration include intravenous, intraarterial, intraperitoneal, intrathecal, intraventricular, intraurethral, intrasternal, intracranial, intramuscular and subcutaneous. Suitable devices for parenteral administration include needle (including microneedle) injectors, needle-free injectors and infusion techniques.

Parenteral formulations are typically aqueous solutions which may contain excipients such as salts, carbohydrates and buffering agents (preferably to a pH of from 3 to 9), but, for some applications, they may be more suitably formulated as a sterile non-aqueous solution or as a dried form to be used in conjunction with a suitable vehicle such as sterile, pyrogen-free water.

The preparation of parenteral formulations under sterile conditions, for example, by lyophilisation, may readily be accomplished using standard pharmaceutical techniques well known to those skilled in the art.

The solubility of compounds of formula (I) used in the preparation of parenteral solutions may be increased by the use of appropriate formulation techniques, such as the incorporation of solubility-enhancing agents. Formulations for parenteral administration may be formulated to be immediate and/or modified release. Modified release formulations include delayed-, sustained-, pulsed-, controlled-, targeted and programmed release. Thus compounds of the invention may be formulated as a solid, semi-solid, or thixotropic liquid for administration as an implanted depot providing modified release of the active compound. Examples of such formulations include drug-coated stents and poly(dl-lactic-coglycolic)acid (PGLA) microspheres.

The compounds of the invention may also be administered topically to the skin or mucosa, that is, dermally or transdermally. Typical formulations for this purpose include gels, hydrogels, lotions, solutions, creams, ointments, dusting powders, dressings, foams, films, skin patches, wafers, implants, sponges, fibres, bandages and microemulsions. Liposomes may also be used. Typical carriers include alcohol, water, mineral oil, liquid petrolatum, white petrolatum, glycerin, polyethylene glycol and propylene glycol. Penetration enhancers may be incorporated—see, for example, J Pharm Sci, 88 (10), 955-958, by Finnin and Morgan (October 1999).

Other means of topical administration include delivery by electroporation, iontophoresis, phonophoresis, sonophoresis and microneedle or needle-free (e.g. Powderject™, Bioject™, etc.) injection.

The compounds of the invention can also be administered intranasally or by inhalation, typically in the form of a dry powder (either alone, as a mixture, for example, in a dry blend with lactose, or as a mixed component particle, for example, mixed with phospholipids, such as phosphatidylcholine) from a dry powder inhaler or as an aerosol spray from a pressurised container, pump, spray, atomiser (preferably an atomiser using electrohydrodynamics to produce a fine mist), or nebuliser, with or without the use of a suitable propellant, such as 1,1,1,2-tetrafluoroethane or 1,1,1,2,3,3,3-heptafluoropropane. For intranasal use, the powder may comprise a bioadhesive agent, for example, chitosan or cyclodextrin.

The pressurised container, pump, spray, atomizer, or nebuliser contains a solution or suspension of the compound(s) of the invention comprising, for example, ethanol, aqueous ethanol, or a suitable alternative agent for dispersing, solubilising, or extending release of the active, a propellant(s) as solvent and an optional surfactant, such as sorbitan trioleate, oleic acid, or an oligolactic acid.

Prior to use in a dry powder or suspension formulation, the drug product is micronised to a size suitable for delivery by inhalation (typically less than 5 microns). This may be achieved by any appropriate comminuting method, such as spiral jet milling, fluid bed jet milling, supercritical fluid processing to form nanoparticles, high pressure homogenisation, or spray drying.

Capsules (made, for example, from gelatin or hydroxypropylmethylcellulose), blisters and cartridges for use in an inhaler or insufflator may be formulated to contain a powder mix of the compound of the invention, a suitable powder base such as lactose or starch and a performance modifier such as l-leucine, mannitol, or magnesium stearate. The lactose may be anhydrous or in the form of the monohydrate, preferably the latter. Other suitable excipients include dextran, glucose, maltose, sorbitol, xylitol, fructose, sucrose and trehalose.

A suitable solution formulation for use in an atomiser using electrohydrodynamics to produce a fine mist may contain from 1 µg to 20 mg of the compound of the invention per actuation and the actuation volume may vary from 1 µl to 100 µl. A typical formulation may comprise a compound of formula (I), propylene glycol, sterile water, ethanol and sodium chloride. Alternative solvents which may be used instead of propylene glycol include glycerol and polyethylene glycol.

Suitable flavours, such as menthol and levomenthol, or sweeteners, such as saccharin or saccharin sodium, may be added to those formulations of the invention intended for inhaled/intranasal administration.

In the case of dry powder inhalers and aerosols, the dosage unit is determined by means of a valve which delivers a metered amount. Units in accordance with the invention are typically arranged to administer a metered dose or "puff" containing from 1 μg to 100 mg of the compound of formula (I). The overall daily dose will typically be in the range 1 μg to 200 mg which may be administered in a single dose or, more usually, as divided doses throughout the day.

The compounds of the invention may be administered rectally or vaginally, for example, in the form of a suppository, pessary, microbicide, vaginal ring or enema. Cocoa butter is a traditional suppository base, but various alternatives may be used as appropriate.

The compounds of the invention may also be administered directly to the eye or ear, typically in the form of drops of a micronised suspension or solution in isotonic, pH-adjusted, sterile saline. Other formulations suitable for ocular and aural administration include ointments, biodegradable (e.g. absorbable gel sponges, collagen) and non-biodegradable (e.g. silicone) implants, wafers, lenses and particulate or vesicular systems, such as niosomes or liposomes. A polymer such as crossed-linked polyacrylic acid, polyvinylalcohol, hyaluronic acid, a cellulosic polymer, for example, hydroxypropylmethylcellulose, hydroxyethylcellulose, or methyl cellulose, or a heteropolysaccharide polymer, for example, gelan gum, may be incorporated together with a preservative, such as benzalkonium chloride. Such formulations may also be delivered by iontophoresis.

The compounds of the invention may be combined with soluble macromolecular entities, such as cyclodextrin and suitable derivatives thereof or polyethylene glycol-containing polymers, in order to improve their solubility, dissolution rate, taste-masking, bioavailability and/or stability for use in any of the aforementioned modes of administration.

Drug-cyclodextrin complexes, for example, are found to be generally useful for most dosage forms and administration routes. Both inclusion and non-inclusion complexes may be used. As an alternative to direct complexation with the drug, the cyclodextrin may be used as an auxiliary additive, i.e. as a carrier, diluent, or solubiliser. Most commonly used for these purposes are alpha-, beta- and gamma-cyclodextrins, examples of which may be found in International Patent Applications Nos. WO 91/11172, WO 94/02518 and WO 98/55148.

For administration to human patients, the total daily dose of the compounds of the invention is typically in the range 1 mg to 10 g, such as 10 mg to 1 g, for example 25 mg to 500 mg depending, of course, on the mode of administration and efficacy. For example, oral administration may require a total daily dose of from 50 mg to 100 mg. The total daily dose may be administered in single or divided doses and may, at the physician's discretion, fall outside of the typical range given herein. These dosages are based on an average human subject having a weight of about 60 kg to 70 kg. The physician will readily be able to determine doses for subjects whose weight falls outside this range, such as infants and the elderly.

As noted above, the compounds of the invention are useful because they exhibit pharmacological activity in animals, i.e., Nav1.7 channel inhibition. More particularly, the compounds of the invention are of use in the treatment of disorders for which a Nav1.7 inhibitor is indicated. Preferably the animal is a mammal, more preferably a human.

In a further aspect of the invention there is provided a compound of the invention for use as a medicament.

In a further aspect of the invention there is provided a compound of the invention for the treatment of a disorder for which a Nav1.7 inhibitor is indicated.

In a further aspect of the invention there is provided use of a compound of the invention for the preparation of a medicament for the treatment of a disorder for which a Nav1.7 inhibitor is indicated.

In a further aspect of the invention there is provided a method of treating a disorder in an animal (preferably a mammal, more preferably a human) for which a Nav1.7 inhibitor is indicated, comprising administering to said animal a therapeutically effective amount of a compound of the invention.

Disorders for which a Nav1.7 inhibitor is indicated include pain, particularly neuropathic, nociceptive and inflammatory pain.

Physiological pain is an important protective mechanism designed to warn of danger from potentially injurious stimuli from the external environment. The system operates through a specific set of primary sensory neurones and is activated by noxious stimuli via peripheral transducing mechanisms (see Millan, 1999, Prog. Neurobiol., 57, 1-164 for a review). These sensory fibres are known as nociceptors and are characteristically small diameter axons with slow conduction velocities. Nociceptors encode the intensity, duration and quality of noxious stimulus and by virtue of their topographically organised projection to the spinal cord, the location of the stimulus. The nociceptors are found on nociceptive nerve fibres of which there are two main types, A-delta fibres (myelinated) and C fibres (non-myelinated). The activity generated by nociceptor input is transferred, after complex processing in the dorsal horn, either directly, or via brain stem relay nuclei, to the ventrobasal thalamus and then on to the cortex, where the sensation of pain is generated.

Pain may generally be classified as acute or chronic. Acute pain begins suddenly and is short-lived (usually twelve weeks or less). It is usually associated with a specific cause such as a specific injury and is often sharp and severe. It is the kind of pain that can occur after specific injuries resulting from surgery, dental work, a strain or a sprain. Acute pain does not generally result in any persistent psychological response. In contrast, chronic pain is long-term pain, typically persisting for more than three months and leading to significant psychological and emotional problems. Common examples of chronic pain are neuropathic pain (e.g. painful diabetic neuropathy, postherpetic neuralgia), carpal tunnel syndrome, back pain, headache, cancer pain, arthritic pain and chronic post-surgical pain.

When a substantial injury occurs to body tissue, via disease or trauma, the characteristics of nociceptor activation are altered and there is sensitisation in the periphery, locally around the injury and centrally where the nociceptors terminate. These effects lead to a hightened sensation of pain. In acute pain these mechanisms can be useful, in promoting protective behaviours which may better enable repair processes to take place. The normal expectation would be that sensitivity returns to normal once the injury has healed. However, in many chronic pain states, the hypersensitivity far outlasts the healing process and is often due to nervous system injury. This injury often leads to abnormalities in sensory nerve fibres associated with maladaptation and aberrant activity (Woolf & Salter, 2000, Science, 288, 1765-1768).

Clinical pain is present when discomfort and abnormal sensitivity feature among the patient's symptoms. Patients tend to be quite heterogeneous and may present with various pain symptoms. Such symptoms include: 1) spontaneous pain which may be dull, burning, or stabbing; 2) exaggerated pain responses to noxious stimuli (hyperalgesia); and 3) pain produced by normally innocuous stimuli (allodynia—Meyer et al., 1994, Textbook of Pain, 13-44). Although patients suffering from various forms of acute and chronic pain may have similar symptoms, the underlying mechanisms may be different and may, therefore, require different treatment strategies. Pain can also therefore be divided into a number of different subtypes according to differing pathophysiology, including nociceptive, inflammatory and neuropathic pain.

Nociceptive pain is induced by tissue injury or by intense stimuli with the potential to cause injury. Pain afferents are activated by transduction of stimuli by nociceptors at the site of injury and activate neurons in the spinal cord at the level of their termination. This is then relayed up the spinal tracts to the brain where pain is perceived (Meyer et al., 1994, Textbook of Pain, 13-44). The activation of nociceptors activates two types of afferent nerve fibres. Myelinated A-delta fibres transmit rapidly and are responsible for sharp and stabbing pain sensations, whilst unmyelinated C fibres transmit at a slower rate and convey a dull or aching pain. Moderate to severe acute nociceptive pain is a prominent feature of pain from central nervous system trauma, strains/sprains, burns, myocardial infarction and acute pancreatitis, post-operative pain (pain following any type of surgical procedure), post-traumatic pain, renal colic, cancer pain and back pain. Cancer pain may be chronic pain such as tumour related pain (e.g. bone pain, headache, facial pain or visceral pain) or pain associated with cancer therapy (e.g. postchemotherapy syndrome, chronic postsurgical pain syndrome or post radiation syndrome). Cancer pain may also occur in response to chemotherapy, immunotherapy, hormonal therapy or radiotherapy. Back pain may be due to herniated or ruptured intervertebral discs or abnormalities of the lumber facet joints, sacroiliac joints, paraspinal muscles or the posterior longitudinal ligament. Back pain may resolve naturally but in some patients, where it lasts over 12 weeks, it becomes a chronic condition which can be particularly debilitating.

Neuropathic pain is currently defined as pain initiated or caused by a primary lesion or dysfunction in the nervous system. Nerve damage can be caused by trauma and disease and thus the term 'neuropathic pain' encompasses many disorders with diverse aetiologies. These include, but are not limited to, peripheral neuropathy, diabetic neuropathy, post herpetic neuralgia, trigeminal neuralgia, back pain, cancer neuropathy, HIV neuropathy, phantom limb pain, carpal tunnel syndrome, central post-stroke pain and pain associated with chronic alcoholism, hypothyroidism, uremia, multiple sclerosis, spinal cord injury, Parkinson's disease, epilepsy and vitamin deficiency. Neuropathic pain is pathological as it has no protective role. It is often present well after the original cause has dissipated, commonly lasting for years, significantly decreasing a patient's quality of life (Woolf and Mannion, 1999, Lancet, 353, 1959-1964). The symptoms of neuropathic pain are difficult to treat, as they are often heterogeneous even between patients with the same disease (Woolf & Decosterd, 1999, Pain Supp., 6, S141-S147; Woolf and Mannion, 1999, Lancet, 353, 1959-1964). They include spontaneous pain, which can be continuous, and paroxysmal or abnormal evoked pain, such as hyperalgesia (increased sensitivity to a noxious stimulus) and allodynia (sensitivity to a normally innocuous stimulus).

The inflammatory process is a complex series of biochemical and cellular events, activated in response to tissue injury or the presence of foreign substances, which results in swelling and pain (Levine and Taiwo, 1994, Textbook of Pain, 45-56). Arthritic pain is the most common inflammatory pain. Rheumatoid disease is one of the commonest chronic inflammatory conditions in developed countries and rheumatoid arthritis is a common cause of disability. The exact aetiology of rheumatoid arthritis is unknown, but current hypotheses suggest that both genetic and microbiological factors may be important (Grennan & Jayson, 1994, Textbook of Pain, 397-407). It has been estimated that almost 16 million Americans have symptomatic osteoarthritis (OA) or degenerative joint disease, most of whom are over 60 years of age, and this is expected to increase to 40 million as the age of the population increases, making this a public health problem of enormous magnitude (Houge & Mersfelder, 2002, Ann Pharmacother., 36, 679-686; McCarthy et al., 1994, Textbook of Pain, 387-395). Most patients with osteoarthritis seek medical attention because of the associated pain. Arthritis has a significant impact on psychosocial and physical function and is known to be the leading cause of disability in later life. Ankylosing spondylitis is also a rheumatic disease that causes arthritis of the spine and sacroiliac joints. It varies from intermittent episodes of back pain that occur throughout life to a severe chronic disease that attacks the spine, peripheral joints and other body organs.

Another type of inflammatory pain is visceral pain which includes pain associated with inflammatory bowel disease (IBD). Visceral pain is pain associated with the viscera, which encompass the organs of the abdominal cavity. These organs include the sex organs, spleen and part of the digestive system. Pain associated with the viscera can be divided into digestive visceral pain and non-digestive visceral pain. Commonly encountered gastrointestinal (GI) disorders that cause pain include functional bowel disorder (FBD) and inflammatory bowel disease (IBD). These GI disorders include a wide range of disease states that are currently only moderately controlled, including, in respect of FBD, gastro-esophageal reflux, dyspepsia, irritable bowel syndrome (IBS) and functional abdominal pain syndrome (FAPS), and, in respect of IBD, Crohn's disease, ileitis and ulcerative colitis, all of which regularly produce visceral pain. Other types of visceral pain include the pain associated with dysmenorrhea, cystitis and pancreatitis and pelvic pain.

It should be noted that some types of pain have multiple aetiologies and thus can be classified in more than one area, e.g. back pain and cancer pain have both nociceptive and neuropathic components.

Other types of pain include:
pain resulting from musculo-skeletal disorders, including myalgia, fibromyalgia, spondylitis, sero-negative (non-rheumatoid) arthropathies, non-articular rheumatism, dystrophinopathy, glycogenolysis, polymyositis and pyomyositis;
heart and vascular pain, including pain caused by angina, myocardical infarction, mitral stenosis, pericarditis, Raynaud's phenomenon, scleredoma and skeletal muscle ischemia;
head pain, such as migraine (including migraine with aura and migraine without aura), cluster headache, tension-type headache mixed headache and headache associated with vascular disorders;
erythermalgia; and
orofacial pain, including dental pain, otic pain, burning mouth syndrome and temporomandibular myofascial pain.

A Nav1.7 inhibitor may be usefully combined with another pharmacologically active compound, or with two or more other pharmacologically active compounds, particularly in the treatment of pain. Such combinations offer the possibility of significant advantages, including patient compliance, ease of dosing and synergistic activity.

In the combinations that follow the compound of the invention may be administered simultaneously, sequentially or separately in combination with the other therapeutic agent or agents.

A Nav1.7 inhibitor of formula (I), or a pharmaceutically acceptable salt thereof, as defined above, may be administered in combination with one or more agents selected from:
- an alternative Nav1.7 channel modulator, such as another compound of the present invention or a compound disclosed in WO 2009/012242;
- an alternative sodium channel modulator, such as a Nav1.3 modulator (e.g. as disclosed in WO2008/118758); or a Nav1.8 modulator (e.g. as disclosed in WO 2008/135826, more particularly N-[6-Amino-5-(2-chloro-5-methoxyphenyl)pyridin-2-yl]-1-methyl-1H-pyrazole-5-carboxamide);
- an inhibitor of nerve growth factor signaling, such as: an agent that binds to NGF and inhibits NGF biological activity and/or downstream pathway(s) mediated by NGF signaling (e.g. tanezumab), a TrkA antagonist or a p75 antagonist;
- a compound which increases the levels of endocannabinoid, such as a compound with fatty acid amid hydrolase inhibitory (FAAH) activity, in particular those disclosed in WO 2008/047229 (e.g. N-pyridazin-3-yl-4-(3-{[5-(trifluoromethyl)pyridine-2-yl]oxy}benzylidene) piperidene-1-carboxamide);
- an opioid analgesic, e.g. morphine, heroin, hydromorphone, oxymorphone, levorphanol, levallorphan, methadone, meperidine, fentanyl, cocaine, codeine, dihydrocodeine, oxycodone, hydrocodone, propoxyphene, nalmefene, nalorphine, naloxone, naltrexone, buprenorphine, butorphanol, nalbuphine or pentazocine;
- a nonsteroidal antiinflammatory drug (NSAID), e.g. aspirin, diclofenac, diflusinal, etodolac, fenbufen, fenoprofen, flufenisal, flurbiprofen, ibuprofen, indomethacin, ketoprofen, ketorolac, meclofenamic acid, mefenamic acid, meloxicam, nabumetone, naproxen, nimesulide, nitroflurbiprofen, olsalazine, oxaprozin, phenylbutazone, piroxicam, sulfasalazine, sulindac, tolmetin or zomepirac;
- a barbiturate sedative, e.g. amobarbital, aprobarbital, butabarbital, butabital, mephobarbital, metharbital, methohexital, pentobarbital, phenobartital, secobarbital, talbutal, theamylal or thiopental;
- a benzodiazepine having a sedative action, e.g. chlordiazepoxide, clorazepate, diazepam, flurazepam, lorazepam, oxazepam, temazepam or triazolam;
- an $H_1$ antagonist having a sedative action, e.g. diphenhydramine, pyrilamine, promethazine, chlorpheniramine or chlorcyclizine;
- a sedative such as glutethimide, meprobamate, methaqualone or dichloralphenazone;
- a skeletal muscle relaxant, e.g. baclofen, carisoprodol, chlorzoxazone, cyclobenzaprine, methocarbamol or orphrenadine;
- an NMDA receptor antagonist, e.g. dextromethorphan ((+)-3-hydroxy-N-methylmorphinan) or its metabolite dextrorphan ((+)-3-hydroxy-N-methylmorphinan), ketamine, memantine, pyrroloquinoline quinine, cis-4-(phosphonomethyl)-2-piperidinecarboxylic acid, budipine, EN-3231 (MorphiDex®, a combination formulation of morphine and dextromethorphan), topiramate, neramexane or perzinfotel including an NR2B antagonist, e.g. ifenprodil, traxoprodil or (−)-(R)-6-{2-[4-(3-fluorophenyl)-4-hydroxy-1-piperidinyl]-1-hydroxyethyl-3,4-dihydro-2(1H)-quinolinone;
- an alpha-adrenergic, e.g. doxazosin, tamsulosin, clonidine, guanfacine, dexmetatomidine, modafinil, or 4-amino-6,7-dimethoxy-2-(5-methane-sulfonamido-1,2,3,4-tetrahydroisoquinol-2-yl)-5-(2-pyridyl) quinazoline;
- a tricyclic antidepressant, e.g. desipramine, imipramine, amitriptyline or nortriptyline;
- an anticonvulsant, e.g. carbamazepine, lamotrigine, topiratmate or valproate;
- a tachykinin (NK) antagonist, particularly an NK-3, NK-2 or NK-1 antagonist, e.g. (αR,9R)-7-[3,5-bis(trifluoromethyl)benzyl]-8,9,10,11-tetrahydro-9-methyl-5-(4-methylphenyl)-7H-[1,4]diazocino[2,1-g][1,7]-naphthyridine-6-13-dione (TAK-637), 5-[[(2R,3S)-2-[(1R)-1-[3,5-bis(trifluoromethyl)phenyl]ethoxy-3-(4-fluorophenyl)-4-morpholinyl]-methyl]-1,2-dihydro-3H-1,2,4-triazol-3-one (MK-869), aprepitant, lanepitant, dapitant or 3-[[2-methoxy-5-(trifluoromethoxy)phenyl]-methylamino]-2-phenylpiperidine (2S,3S);
- a muscarinic antagonist, e.g oxybutynin, tolterodine, propiverine, tropsium chloride, darifenacin, solifenacin, temiverine and ipratropium;
- a COX-2 selective inhibitor, e.g. celecoxib, rofecoxib, parecoxib, valdecoxib, deracoxib, etoricoxib, or lumiracoxib;
- a coal-tar analgesic, in particular paracetamol;
- a neuroleptic such as droperidol, chlorpromazine, haloperidol, perphenazine, thioridazine, mesoridazine, trifluoperazine, fluphenazine, clozapine, olanzapine, risperidone, ziprasidone, quetiapine, sertindole, aripiprazole, sonepiprazole, blonanserin, iloperidone, perospirone, raclopride, zotepine, bifeprunox, asenapine, lurasidone, amisulpride, balaperidone, palindore, eplivanserin, osanetant, rimonabant, meclinertant, Miraxion® or sarizotan;
- a vanilloid receptor agonist (e.g. resinferatoxin) or antagonist (e.g. capsazepine);
- a beta-adrenergic such as propranolol;
- a local anaesthetic such as mexiletine;
- a corticosteroid such as dexamethasone;
- a 5-HT receptor agonist or antagonist, particularly a $5\text{-HT}_{1B/1D}$ agonist such as eletriptan, sumatriptan, naratriptan, zolmitriptan or rizatriptan;
- a $5\text{-HT}_2$, receptor antagonist such as R(+)-alpha-(2,3-dimethoxy-phenyl)-1-[2-(4-fluorophenylethyl)]-4-piperidinemethanol (MDL-100907);
- a $5\text{-HT}_3$ antagonist, such as ondansetron
- a cholinergic (nicotinic) analgesic, such as ispronicline (TC-1734), (E)-N-methyl-4-(3-pyridinyl)-3-buten-1-amine (RJR-2403), (R)-5-(2-azetidinylmethoxy)-2-chloropyridine (ABT-594) or nicotine;
- Tramadol®;
- a PDEV inhibitor, such as 5-[2-ethoxy-5-(4-methyl-1-piperazinyl-sulphonyl)phenyl]-1-methyl-3-n-propyl-1,6-dihydro-7H-pyrazolo[4,3-d]pyrimidin-7-one (sildenafil), (6R,12aR)-2,3,6,7,12,12a-hexahydro-2-methyl-6-(3,4-methylenedioxyphenyl)-pyrazino[2',1':6,1]-pyrido[3,4-b]indole-1,4-dione (IC-351 or tadalafil), 2-[2-ethoxy-5-(4-ethyl-piperazin-1-yl-1-sulphonyl)-phenyl]-5-methyl-7-propyl-3H-imidazo[5,1-f][1,2,4]triazin-4-one (vardenafil), 5-(5-acetyl-2-butoxy-3-pyridinyl)-3-ethyl-2-(1-ethyl-3-azetidinyl)-2,6-dihydro-7H-pyrazolo[4,3-d]pyrimidin-7-one, 5-(5- acetyl-2-propoxy-3-pyridinyl)-3-ethyl-2-(1-isopropyl-3-azetidinyl)-2,6-dihydro-7H-pyrazolo[4,3-d]pyrimidin-7-one, 5-[2-ethoxy-5-(4-ethylpiperazin-1-ylsulphonyl)pyridin-3-yl]-3-ethyl-2-[2-methoxyethyl]-2,6-dihydro-7H-pyrazolo[4,3-d]pyrimidin-7-one, 4-[(3-chloro-4-methoxybenzyl)amino]-2-[(2S)-2-(hydroxymethyl)pyrrolidin-1-yl]-N-(pyrimidin-2-ylmethyl)pyrimidine-5-carboxamide, 3-(1-methyl-7-oxo-3-propyl-6,7-dihydro-1H-pyrazolo[4,3-d]pyrimidin-5-yl)-N-[2-(1-methylpyrrolidin-2-yl)ethyl]-4-propoxybenzenesulfonamide;

an alpha-2-delta ligand such as gabapentin, pregabalin, 3-methylgabapentin, (1α,3α,5α)(3-amino-methyl-bicyclo[3.2.0]hept-3-yl)-acetic acid, (3S,5R)-3-aminomethyl-5-methyl-heptanoic acid, (3S,5R)-3-amino-5-methyl-heptanoic acid, (3S,5R)-3-amino-5-methyl-octanoic acid, (2S,4S)-4-(3-chlorophenoxy)proline, (2S,4S)-4-(3-fluorobenzyl)-proline, [(1R,5R,6S)-6-(aminomethyl)bicyclo[3.2.0]hept-6-yl]acetic acid, 3-(1-aminomethyl-cyclohexylmethyl)-4H-[1,2,4]oxadiazol-5-one, C-[1-(1H-tetrazol-5-ylmethyl)-cycloheptyl]-methylamine, (3S,4S)-(1-aminomethyl-3,4-dimethyl-cyclopentyl)-acetic acid, (3S,5R)-3-aminomethyl-5-methyl-octanoic acid, (3S,5R)-3-amino-5-methyl-nonanoic acid, (3S,5R)-3-amino-5-methyl-octanoic acid, (3R,4R,5R)-3-amino-4,5-dimethyl-heptanoic acid and (3R,4R,5R)-3-amino-4,5-dimethyl-octanoic acid;

metabotropic glutamate subtype 1 receptor (mGluR1) antagonist;

a serotonin reuptake inhibitor such as sertraline, sertraline metabolite demethylsertraline, fluoxetine, norfluoxetine (fluoxetine desmethyl metabolite), fluvoxamine, paroxetine, citalopram, citalopram metabolite desmethylcitalopram, escitalopram, d,l-fenfluramine, femoxetine, ifoxetine, cyanodothiepin, litoxetine, dapoxetine, nefazodone, cericlamine and trazodone;

a noradrenaline (norepinephrine) reuptake inhibitor, such as maprotiline, lofepramine, mirtazepine, oxaprotiline, fezolamine, tomoxetine, mianserin, buprorion, buprorion metabolite hydroxybuproprion, nomifensine and viloxazine (Vivalan®), especially a selective noradrenaline reuptake inhibitor such as reboxetine, in particular (S,S)-reboxetine;

a dual serotonin-noradrenaline reuptake inhibitor, such as venlafaxine, venlafaxine metabolite O-desmethylvenlafaxine, clomipramine, clomipramine metabolite desmethylclomipramine, duloxetine, milnacipran and imipramine;

an inducible nitric oxide synthase (iNOS) inhibitor such as S-[2-[(1-iminoethyl)amino]ethyl]-L-homocysteine, S-[2-[(1-iminoethyl)-amino]ethyl]-4,4-dioxo-L-cysteine, S-[2-[(1-iminoethyl)amino]ethyl]-2-methyl-L-cysteine, (2S,5Z)-2-amino-2-methyl-7-[(1-iminoethyl)amino]-5-heptenoic acid, 2-[[(1R,3S)-3-amino-4-hydroxy-1-(5-thiazolyl)-butyl]thio]-5-chloro-3-pyridinecarbonitrile; 2-[[(1R,3S)-3-amino-4-hydroxy-1-(5-thiazolyl)butyl]thio]-4-chlorobenzonitrile, (2S,4R)-2-amino-4-[[2-chloro-5-(trifluoromethyl)phenyl]thio]-5-thiazolebutanol, 2-[[(1R,3S)-3-amino-4-hydroxy-1-(5-thiazolyl) butyl]thio]-6-(trifluoromethyl)-3 pyridinecarbonitrile, 2-[[(1R,3S)-3-amino-4-hydroxy-1-(5-thiazolyl)butyl]thio]-5-chlorobenzonitrile, N-[4-[2-(3-chlorobenzylamino) ethyl]phenyl]thiophene-2-carboxamidine, or guanidinoethyldisulfide;

an acetylcholinesterase inhibitor such as donepezil;

a prostaglandin $E_2$ subtype 4 (EP4) antagonist such as N-[({2-[4-(2-ethyl-4,6-dimethyl-1H-imidazo[4,5-c]pyridin-1-yl)phenyl]ethyl}amino)-carbonyl]-4-methyl-benzenesulfonamide or 4-[(1S)-1-({[5-chloro-2-(3-fluorophenoxy)pyridin-3-yl]carbonyl}amino)ethyl] benzoic acid;

a microsomal prostaglandin E synthase type 1 (mPGES-1) inhibitor;

a leukotriene B4 antagonist; such as 1-(3-biphenyl-4-ylmethyl-4-hydroxy-chroman-7-yl)-cyclopentanecarboxylic acid (CP-105696), 5-[2-(2-Carboxyethyl)-3-[6-(4-methoxyphenyl)-5E-hexenyl]oxyphenoxy]-valeric acid (ONO-4057) or DPC-11870, and a 5-lipoxygenase inhibitor, such as zileuton, 6-[(3-fluoro-5-[4-methoxy-3,4,5,6-tetrahydro-2H-pyran-4-yl])phenoxy-methyl]-1-methyl-2-quinolone (ZD-2138), or 2,3,5-trimethyl-6-(3-pyridylmethyl),1,4-benzoquinone (CV-6504).

There is also included within the scope the present invention combinations of a compound of the invention together with one or more additional therapeutic agents which slow down the rate of metabolism of the compound of the invention, thereby leading to increased exposure in patients. Increasing the exposure in such a manner is known as boosting. This has the benefit of increasing the efficacy of the compound of the invention or reducing the dose required to achieve the same efficacy as an unboosted dose. The metabolism of the compounds of the invention includes oxidative processes carried out by P450 (CYP450) enzymes, particularly CYP 3A4 and conjugation by UDP glucuronosyl transferase and sulphating enzymes. Thus, among the agents that may be used to increase the exposure of a patient to a compound of the present invention are those that can act as inhibitors of at least one isoform of the cytochrome P450 (CYP450) enzymes. The isoforms of CYP450 that may be beneficially inhibited include, but are not limited to, CYP1A2, CYP2D6, CYP2C9, CYP2C19 and CYP3A4. Suitable agents that may be used to inhibit CYP 3A4 include ritonavir, saquinavir, ketoconazole, N-(3,4-diffluorobenzyl)-N-methyl-2-{[(4-methoxypyridin-3-yl)amino]sulfonyl}benzamide and N-(1-(2-(5-(4-fluorobenzyl)-3-(pyridin-4-yl)-1H-pyrazol-1-yl) acetyl)piperidin-4-yl)methanesulfonamide.

It is within the scope of the invention that two or more pharmaceutical compositions, at least one of which contains a compound of the invention, may conveniently be combined in the form of a kit suitable for coadministration of the compositions. Thus the kit of the invention comprises two or more separate pharmaceutical compositions, at least one of which contains a compound of the invention, and means for separately retaining said compositions, such as a container, divided bottle, or divided foil packet. An example of such a kit is the familiar blister pack used for the packaging of tablets, capsules and the like. The kit of the invention is particularly suitable for administering different dosage forms, for example, oral and parenteral, for administering the separate compositions at different dosage intervals, or for titrating the separate compositions against one another. To assist compliance, the kit typically comprises directions for administration and may be provided with a so-called memory aid.

In another aspect the invention provides a pharmaceutical product (such as in the form of a kit) comprising a compound of the invention together with one or more additional therapeutically active agents as a combined preparation for simultaneous, separate or sequential use in the treatment of a disorder for which a Nav1.7 inhibitor is indicated.

It is to be appreciated that all references herein to treatment include curative, palliative and prophylactic treatment.

In the non-limiting Examples and Preparations that are set out later in the description, and in the aforementioned Schemes, the following the abbreviations, definitions and analytical procedures may be referred to:
AcOH is acetic acid,
DAD is diode array detector;
DCM is dichloromethane; methylene chloride;
DMAP is 4-dimethylaminopyridine;
DMF is N,N-dimethylformamide;
DMSO is dimethyl sulphoxide;
EDCl is 1-(3-dimethylaminopropyl)-3-ethylcarbodiimide hydrochloride;
ELSD is evaporative light scattering detection;
$Et_2O$ is diethyl ether;
EtOAc is ethyl acetate;
isoPrOAc is isopropyl acetate;
EtOH is ethanol;
HCl is hydrochloric acid;
IPA is isopropanol;
LCMS is liquid chromatography mass spectrometry ($R_t$=retention time)
LiOH is lithium hydroxide;
MeOH is methanol;
NaH is sodium hydride;
NaOH is sodium hydroxide;
THF is tetrahydrofuran;

$^1$H Nuclear magnetic resonance (NMR) spectra were in all cases consistent with the proposed structures. Characteristic chemical shifts (δ) are given in parts-per-million downfield from tetramethylsilane using conventional abbreviations for designation of major peaks: e.g. s, singlet; d, doublet; t, triplet; q, quartet; m, multiplet; br, broad. The following abbreviations have been used for common solvents: $CDCl_3$, deuterochloroform; $d_6$-DMSO, deuterodimethylsulphoxide; and $CD_3OD$, deuteromethanol.

Mass spectra, MS (m/z), were recorded using either electrospray ionisation (ESI) or atmospheric pressure chemical ionisation (APCI). When relevant, and unless stated otherwise, the m/z data provided are for isotopes $^{19}F$, $^{35}Cl$ and $^{79}Br$. Automated Preparative High Performance Liquid Chromatography (Auto-HPLC)

Certain compounds of the Examples and Preparations were purified using Automated Preparative High Performance Liquid Chromatography (HPLC). Reversed-phase HPLC conditions were either on FractionLynx systems or on a Trilution system.

In the case of the Fractionlynx system, Samples were submitted dissolved in 1 mL of DMSO. Depending on the nature of the compounds and the results of a pre-analysis, the purification was performed under either acidic ('A-HPLC'), or basic ('B-HPLC') conditions at ambient temperature. A-HPLC was carried out on a Sunfire Prep C18 OBD column (19×100 mm, 5 μm). B-HPLC was carried out on an Xterra Prep MS C18 (19×100 mm, 5 μm), both from Waters. A flow rate of 18 mL/min was used with mobile phase A: water+0.1% modifier (v/v) and B: acetonitrile+0.1% modifier (v/v). For acidic runs the modifier was formic acid, for basic run the modifier was diethylamine. A Waters 2525 binary LC pump supplied a mobile phase with a composition of 5% B for 1 minutes then ran from 5% to 98% B over 6 minutes followed by a 2 minutes hold at 98% B.

Detection was achieved using a Waters 2487 dual wavelength absorbance detector set at 225 nm followed in series by a Polymer Labs PL-ELS 2100 detector and a Waters ZQ 2000 4 way MUX mass spectrometer in parallel. The PL 2100 ELSD was set at 30° C. with 1.6 L/min supply of Nitrogen. The Waters ZQ MS was tuned with the following parameters:

| | |
|---|---|
| ES+ Cone voltage: 30 v | Capillary: 3.20 kv |
| ES− Cone voltage: −30 v | Capillary: −3.00 kv |
| Desolvation gas: 600 L/hr | |
| Source Temp: 120° C. | |
| Scan range 150-900 Da | |

The fraction collection was triggered by both MS and ELSD.

Quality control (QC) analysis was performed using a LCMS method. Acidic runs were carried out on a Sunfire C18 (4.6×50 mm, 5 μm), basic runs were carried out on a Xterra C18 (4.6×50 mm, 5 μm), both from Waters. A flow rate of 1.5 mL/min was used with mobile phase A: water+0.1% modifier (v/v) and B: acetonitrile+0.1% modifier (v/v). For acidic runs the modifier was formic acid, for basic run the modifier was ammonia. A Waters 1525 binary LC pump ran a gradient elution from 5% to 95% B over 3 minutes followed by a 1 minute hold at 95% B. Detection was achieved using a Waters MUX UV 2488 detector set at 225 nm followed in series by a Polymer Labs PL-ELS 2100 detector and a Waters ZQ 2000 4 way MUX mass spectrometer in parallel. The PL 2100 ELSD was set at 30° C. with 1.6 L/min supply of Nitrogen. The Waters ZQ MS was tuned with the following parameters:

| | |
|---|---|
| ES+ Cone voltage: 25 v | Capillary: 3.30 kv |
| ES− Cone voltage: −30 v | Capillary: −2.50 kv |
| Desolvation gas: 800 L/hr | |
| Source Temp: 150° C. | |
| Scan range 160-900 Da | |

Where the reversed-phase Trilution system was used (T-HPLC) the conditions were as follows:
Mobile phase A: 0.1% formic acid in water
Mobile phase B: 0.1% formic acid in acetonitrile
Column: Phenomenex C18 Luna 21.5 mm×15 cm with 5 micron particle size
Gradient: 95-5% A over 15 min, 15 min hold, 15 mL/min flow rate
UV: 200 nm-400 nm
Temperature: Room temperature
Liquid Chromatography Mass Spectrometry Unless carried out by Auto-HPLC (under conditions of A-HPLC or B-HPLC) as described just above, or as specifically set out in the Examples and Preparations that follow, LCMS conditions were run according to one of the conditions given below (where ratios of solvents are given, the ratios are by volume):
Acidic 2 Minute LCMS
Mobile phase A: 0.1% formic acid in water
Mobile phase B: 0.1% formic acid in 70% methanol: 30% iso-propanol
Column: C18 phase Phenomenex20×4.0 mm with 3 micron particle size
Gradient: 98-10% A over 1.5 min, 0.3 min hold, 0.2 re-eqilibration, 2 mL/min flow rate
UV: 210 nm-450 nm DAD
Temperature: 75° C.
Or
Mobile phase A: 0.1% formic acid in water
Mobile phase B: 0.1% formic acid in acetonitrile
Column: C18 phase Phenomenex20×4.0 mm with 3 micron particle size Gradient: 70-2% A over 1.5 min, 0.3 min hold, 0.2 re-equilibration, 1.8 mL/min flow rate
UV: 210 nm-450 nm DAD
Temperature: 75° C.
Acidic 4.5 Minute LCMS
Mobile phase A: 0.05% formic acid in water
Mobile phase B: acetonitrile
Column: Phenomenex Gemini C18 45×45 mm with 5 micron particle size
Gradient: 80-50% A over 0.5 min, 50-2% A over 3 min, 1 min hold, 0.2 min re-equilibration, 2.0 mL/min flow rate
UV: 220 nm-254 nm DAD
Temperature: 40° C.
Acidic 8 Minute LCMS
Mobile phase A: 0.05% formic acid in water
Mobile phase B: acetonitrile
Column: Phenomenex Gemini C18 45×45 mm with 5 micron particle size
Gradient: 80-50% A over 0.5 min, 50-2% A over 3 min, 4.5 min hold, 0.2 min re-equilibration, 2.0 mL/min flow rate
UV: 220 nm-254 nm DAD
Temperature: 40° C.
Acidic 6 Minute LCMS
Mobile phase A: 0.1% formic acid in water
Mobile phase B: 0.1% formic acid in acetonitrile
Column: C18 phase Waters Sunfire 50×4.6 mm with 5 micron particle size
Gradient: 95-5% A over 3 min, 1 min hold, 2 min re-equilibration, 1.5 mL/min flow rate
UV: 210 nm-450 nm DAD
Temperature: 50° C.
Basic 6 Minute LCMS
Mobile phase A: 0.1% ammonium hydroxide in water
Mobile phase B: 0.1% ammonium hydroxide in acetonitrile
Column: C18 phase Fortis 50×4.6 mm with 5 micron particle size
Gradient: 95-5% A over 3 min, 1 min hold, 2 min re-equilibration, 1 mL/min flow rate
UV: 210 nm-450 nm DAD
Temperature: 50° C.
Acidic 30 Minute LCMS
Mobile phase A: 0.1% formic acid in water
Mobile phase B: 0.1% formic acid in acetonitrile
Column: Phenomenex C18 phase Gemini 150×4.6 mm with 5 micron particle size
Gradient: 98-2% A over 18 min, 2 min hold, 1 mL/min flow rate
UV: 210 nm-450 nm DAD
Temperature: 50° C.
Basic 30 minute LCMS
Mobile phase A: 10 mM ammonium acetate in water
Mobile phase B: 10 mM ammonium acetate in methanol
Column: Phenomenex Phenyl Hexyl 150×4.6 mm with 5 micron particle size
Gradient: 98-2% A over 18 min, 2 min hold, 1 mL/min flow rate
UV: 210 nm-450 nm DAD
Temperature: 50° C.

In the tabulated experimental details that follow, the Examples and Preparations were prepared according to the corresponding reference method. The skilled person will appreciate that, in the synthesis of any specific Example or Preparation, it may be desirable to make minor variations to the reaction conditions of the reference method (e.g. with regard to solvent, temperature and so on).

EXAMPLE 1

4-(4-chloro-2-methoxyphenoxy)-3-(2-methoxypyridin-3-yl)-N-(methylsulfonyl)benzamide diethylamine salt

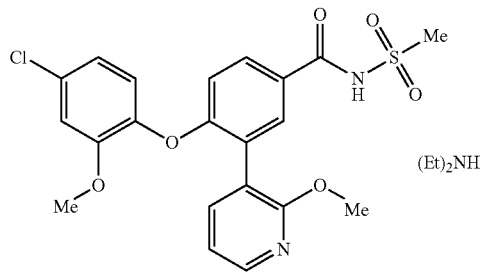 [SMILES: "(Et)2NH" ; COc1cc(Cl)ccc1Oc1ccc(C(=O)NS(C)(=O)=O)cc1-c1cccnc1OC]

A solution of 4-(4-chloro-2-methoxyphenoxy)-3-(2-methoxypyridin-3-yl)benzamide (Preparation 1, 0.299 g, 0.777 mmol) in dry THF (10 mL) was prepared. A solution of lithium bis(trimethylsilyl)amide 1M in THF (2.33 mL, 2.33 mmol) was added. The mixture was stirred at room temperature for 10 minutes, then methanesulfonyl chloride (0.120 mL, 0.178 g, 1.55 mmol) was added and the reaction stirred at room temperature for 3 hours. The reaction was quenched by slow addition of water (30 mL) and the pH of the aqueous (pH=7-8) adjusted to pH=4-5 by slow addition of saturated aqueous solution of potassium hydrogen sulfate. The mixture was extracted with EtOAc (3×20 mL) and the combined organics were washed with brine (30 mL), filtered and concentrated in vacuo to give the crude title compound. The crude product was purified by B-HPLC to afford the title compound as a diethylamine salt (23.7 mg).

LCMS Rt=2.20 minutes MS m/z 463 [MH]$^+$, 461 [M−H]$^-$

EXAMPLE 2

4-[(6-isobutoxypyridin-3-yl)oxy]-3-(2-methoxypyridin-3-yl)-N-(methylsulfonyl)benzamide diethylamine salt

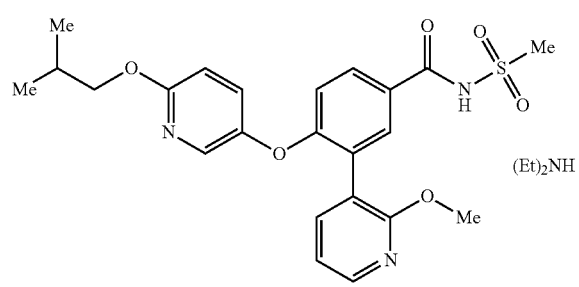 [SMILES: "(Et)2NH" ; COc1ncccc1-c1cc(C(=O)NS(C)(=O)=O)ccc1Oc1ccc(OCC(C)C)nc1]

Prepared according to Example 1 with 4-[(6-isobutoxypyridin-3-yl)oxy]-3-(2-methoxypyridin-3-yl)benzamide (Preparation 4), leaving the reaction 18 hours. The crude product was purified by B-HPLC to afford the title compound as a diethylamine salt (43.1 mg).

LCMS Rt=3.70 minutes MS m/z 472 [MH]$^+$, 470 [M−H]$^-$

EXAMPLE 3

4-(4-chlorophenoxy)-3-(3-methoxypyridin-2-yl)-N-(methylsulfonyl)benzamide

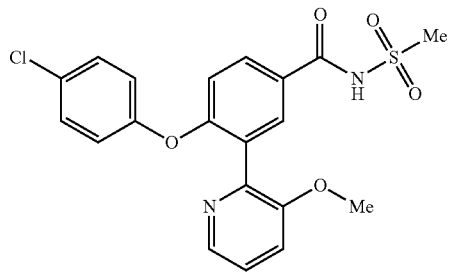 [SMILES: COc1cccnc1-c1cc(C(=O)NS(C)(=O)=O)ccc1Oc1ccc(Cl)cc1]

Lithium hexamethyldisilazane (1.5 mL, 1.55 mmol) was added to a solution of 4-(4-chlorophenoxy)-3-(3-methoxypyridin-2-yl)benzamide (Preparation 11, 0.184 g, 0.52 mmol) in THF (10 mL) and then the mixture was stirred at room temperature for 10 minutes. Methansulfonyl chloride (0.14 mL, 1.81 mmol) was added to the yellow solution and the mixture was stirred at room temperature for 18 hours. The reaction was quenched by the addition of aqueous ammonium chloride (10 mL) and extracted with DCM (3×30 mL). The organic layer was washed with water (2×30 mL), dried over magnesium sulfate, and concentrated in vacuo to afford the crude product (0.294 g). The crude material was purified by preparative A-HPLC to afford the title compound (12.2 mg).
LCMS Rt=3.04 minutes MS m/z 433 [MH]$^+$, 431 [M−H]$^-$

EXAMPLE 4

4-(4-chloro-2-methoxyphenoxy)-2-fluoro-5-(2-methoxypyridin-3-yl)-N-(methylsulfonyl)benzamide

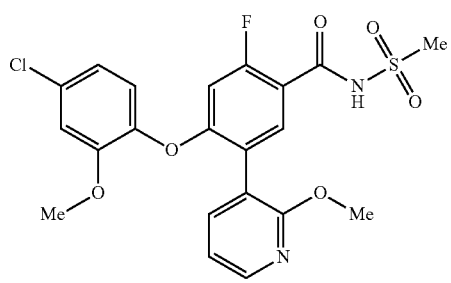 [SMILES: COc1cc(Cl)ccc1Oc1cc(F)c(C(=O)NS(C)(=O)=O)cc1-c1cccnc1OC]

A mixture of 4-(4-chloro-2-methoxyphenoxy)-2-fluoro-5-(2-methoxypyridin-3-yl)benzoic acid (Preparation 15, 0.070 g, 0.114 mmol), O-(7-azabenzotriazol-1-yl)-N,N,N',N'-tetramethyluronium hexafluorophosphate (0.112 g, 0.294 mmol) and N,N-diisopropylethylamine (191 µL, 1.09 mmol) in DCM (10 mL) and dimethylformamide (1.1 mL) was stirred at room temperature for 10 minutes, then methyl sulfonamide (0.0397 g, 0.417 mmol) was added. The reaction was heated at 45° C. for 18 hours under a nitrogen atmosphere, then cooled to room temperature and concentrated in vacuo to afford a pale brown residue. This was partitioned between aqueous hydrochloric acid (0.5 M, 10 mL) and DCM (25 mL). The organic extract was washed with aqueous hydrochloric acid (0.5 M, 2×10 mL), dried over sodium sulfate and concentrated in vacuo to afford a pale brown gum (0.062 g). The crude product was purified by preparative A-HPLC to afford the title compound (26.7 mg):
LCMS Rt=2.32 minutes MS m/z 481 [MH]$^+$, 479 [M−H]$^-$

EXAMPLE 5

3-(2-methoxypyridin-3-yl)-N-(methylsulfonyl)-4-phenoxybenzamide

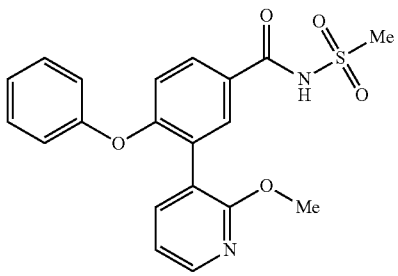 [SMILES: COc1ncccc1-c1cc(C(=O)NS(C)(=O)=O)ccc1Oc1ccccc1]

Lithium bis(trimethylsilyl)amide solution in THF (1 M, 0.78 mL, 0.78 mmol) was added to a solution of 3-(2-methoxypyridin-3-yl)-4-phenoxybenzamide (Preparation 19, 0.1 g, 0.31 mmol) in THF (4 mL) at room temperature and the reaction allowed to stir for 30 minutes. Methanesulfonyl chloride (0.088 g, 0.78 mmol) was added and the reaction was stirred at room temperature for 18 hours. The mixture was then partitioned between EtOAc (40 mL) and water (10 mL). The combined organics were dried over sodium sulfate and concentrated in vacuo to afford a brown solid. The crude product was purified by preparative HPLC to afford the title compound as a white solid (20 mg).
$^1$H NMR (400 MHz, CD$_3$OD): δ 3.37 (s, 3H), 3.82 (s, 3H), 6.97 (m, 3H), 7.05 (m, 1H), 7.15 (t, 1H), 7.38 (m, 2H), 7.70 (d, 1H), 7.88 (d, 1H), 7.92 (s, 1H), 8.18 (d, 1H).
LCMS Rt=2.79 minutes MS m/z 399 [MH]$^+$

EXAMPLE 6

N-(cyclopropylsulfonyl)-3-(2-methoxypyridin-3-yl)-4-phenoxybenzamide

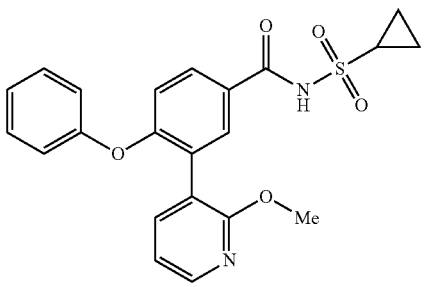 [SMILES: COc1ncccc1-c1cc(C(=O)NS(=O)(=O)C2CC2)ccc1Oc1ccccc1]

Prepared according to Example 5 with 3-(2-methoxypyridin-3-yl)-4-phenoxybenzamide (Preparation 19, 0.030 g, 0.09 mmol) and cyclopropylsulfonyl chloride (0.030 g, 0.21 mmol). The product was purified by preparative HPLC to afford the title compound as a white solid (6.5 mg).
$^1$H NMR (400 MHz, CD$_3$OD): δ 1.0 (m, 2H), 1.20 (m, 2H), 3.02 (m, 1H), 3.84 (s, 3H), 6.85 (m, 4H), 7.02 (t, 1H), 7.22 (t, 2H), 7.58 (d, 1H), 7.78 (d, 1H), 7.80 (s, 1H), 8.02 (d, 1H).
LCMS Rt=2.98 minutes MS m/z 425 [MH]$^+$

EXAMPLE 7

4-[(5-Chloro-6-isopropoxypyridin-3-yl)oxy]-3-(2-methoxypyridin-3-yl)-N-(methylsulfonyl)benzamide

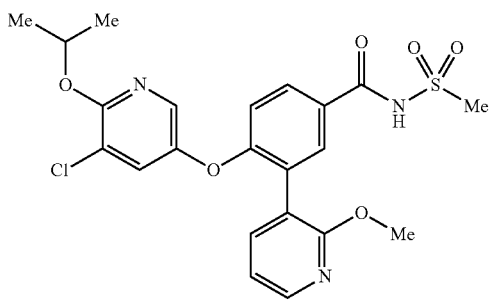 [SMILES: COc1ncccc1-c1cc(C(=O)NS(C)(=O)=O)ccc1Oc1cnc(OC(C)C)c(Cl)c1]

To a solution of 4-[(5-chloro-6-isopropoxypyridin-3-yl)oxy]-3-(2-methoxypyridin-3-yl)benzamide (Preparation 27, 436 mg, 1.05 mmol) in anhydrous THF (10.0 mL) was added lithium bis(trimethylsilyl) amide (1.0 M in THF, 2.63 mL, 2.63 mmol). The solution was stirred for 30 minutes before the addition of methanesulfonyl chloride (210 uL, 2.63 mmol). The reaction mixture was stirred for 1 hour and then a saturated aqueous solution of ammonium chloride (25 mL) was added to the reaction mixture. The reaction mixture was partitioned between water (30 mL) and EtOAc (25 mL). The aqueous phase was separated and extracted with EtOAc (2×25 mL). The combined organic extracts were dried over anhydrous sodium sulfate, filtered and concentrated in vacuo to afford a solid. The material was purified by silica gel column chromatography, eluting with 60:40:1 heptane/EtOAc/acetic acid. Fractions containing product were combined and concentrated in vacuo to obtain the title compound as a solid (230 mg):

$^1$H NMR (400 MHz, CDCl$_3$): δ 1.15 (d, 6H), 3.20 (s, 3H), 3.55 (s, 3H), 5.05 (m, 1H), 6.65 (m, 1H), 6.75 (m, 1H), 7.20 (m, 1H), 7.35 (m, 1H), 7.55 (m, 3H), 7.95 (m, 1H).

LCMS Rt=3.66 minutes MS m/z 492 [MH]$^+$, 490 [M−H]$^-$.

Examples 8-10 were made via a library protocol typified by the following general method using the intermediate prepared in Preparation 24.

General method for the synthesis of 4-(4-chlorophenoxy)-3-aryl-N-(methylsulfonyl)benzamides To a solution of 3-bromo-4-(4-chlorophenoxy)-N-(methylsulfonyl)benzamide (Preparation 24, 33.4 mg, 0.0825 mmol) and arylboronic acid (0.075 mmol) in 0.75 mL 1,4-dioxane was added a solution of cesium carbonate (73.3 mg, 0.225 mmol) in water (113 μL) followed by 1,1'-bis(di-tert-butylphosphino)ferrocene palladium dichloride (2.41 mg, 0.00370 mmol). The reaction mixture was heated to 60° C. in a nitrogen atmosphere for 14 hours, evaporated to dryness in vacuo and the product purified on a HPLC column.

Purification condition 1: Agella Venusil ASB C18 150*21.2 mm*5 m, acetonitrile-water (0.1% trifluoroacetic acid) gradient Purification condition 2: Boston Symmetrix ODS-H 150*30 mm*5 m, acetonitrile-water (0.1% trifluoroacetic acid) gradient.

EXAMPLE 8

4-(4-Chlorophenoxy)-3-(2-ethoxypyridin-3-yl)-N-(methylsulfonyl)benzamide

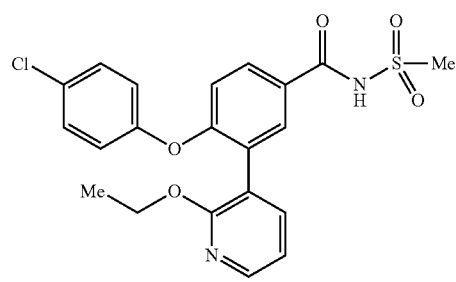 [SMILES: CCOc1ncccc1-c1cc(C(=O)NS(C)(=O)=O)ccc1Oc1ccc(Cl)cc1]

Using 19 mg (0.075 mmol) 2-ethoxy-3-(4,4,5,5-tetramethyl-1,3,2-dioxaborolan-2-yl)pyridine and purified using purification condition 1 to afford the title compound (9.01 mg; 29%).

LCMS Rt=3.407 minutes MS m/z=447 [MH]$^+$
LCMS method:

| | |
|---|---|
| Column | Welch XB-C18 2.1 × 50 mm 5 μm |
| Temperature | 50° C. |
| Mobile Phase A | 0.0375% trifluoroacetic acid in water |
| Mobile Phase B | 0.01875% trifluoroacetic acid in acetonitrile |
| Gradient - Initial | 10% B |
| Time 0.00 min | 10% B |
| Time 0.50 min | 10% B |
| Time 4.00 min | 100% B |
| Time 4.30 min | 10% B |
| Time 4.70 min | 10% B |
| Flow rate | 0.8 mL/min |
| Injection volume | 2 μl |
| Agilent | 1200 HPLC/1956 MSD/SEDEX 75 ELSD |
| Ionization Mode | API-ES |
| Polarity | Positive |

EXAMPLE 9

6-(4-Chlorophenoxy)-4'-fluoro-N-(methylsulfonyl)biphenyl-3-carboxamide

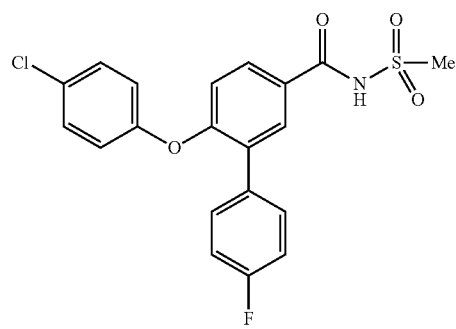 [SMILES: CS(=O)(=O)NC(=O)c1ccc(Oc2ccc(Cl)cc2)c(-c2ccc(F)cc2)c1]

Using 11 mg (0.075 mmol) 4-(fluorophenyl)boronic acid and purification using condition 2 to afford the title compound. (12 mg; 15%):

LCMS Rt=2.967 minutes MS m/z=420 [MH]+

LCMS method:

| Column | Welch XB-C18 2.1 × 50 mm 5 μm |
|---|---|
| Temperature | 50° C. |
| Mobile Phase A | 0.0375% trifluoroacetic acid in water |
| Mobile Phase B | 0.01875% trifluoroacetic acid in acetonitrile |
| Gradient - Initial | 25% B |
| Time 0.00 min | 25% B |
| Time 0.50 min | 25% B |
| Time 3.50 min | 100% B |
| Time 4.00 min | 25% B |
| Time 4.70 min | 25% B |
| Flow rate | 0.8 mL/min |
| Injection volume | 2 μL |
| Agilent | 1200 HPLC/1956 MSD/SEDEX 75 ELSD |
| Ionization Mode | API-ES |
| Polarity | Positive |

EXAMPLE 10

4-(4-Chlorophenoxy)-N-(methylsulfonyl)-3-(1H-pyrazol-3-yl)benzamide

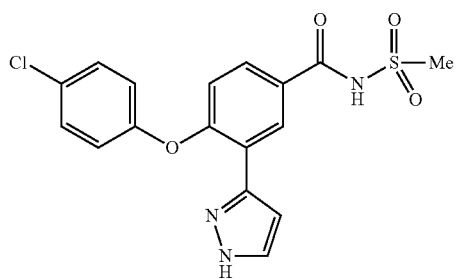 [SMILES: CS(=O)(=O)NC(=O)c1ccc(Oc2ccc(Cl)cc2)c(-c2cc[nH]n2)c1]

Using 15 mg (0.075 mmol) 4-(4,4,5,5-tetramethyl-1,3,2-dioxaborolan-2-yl)-1H-pyrazole and purification condition 1 to afford the title compound (4.21 mg; 9%):

LCMS Rt=3.101 minutes MS m/z 392 [MH]+

LCMS method:

| Column | Welch XB-C18 2.1 × 50 mm 5 μm |
|---|---|
| Temperature | 50° C. |
| Mobile Phase A | 0.0375% trifluoroacetic acid in water |
| Mobile Phase B | 0.01875% trifluoroacetic acid in acetonitrile |
| Gradient - Initial | 1% B |
| Time 0.00 min | 1% B |
| Time 0.60 min | 5% B |
| Time 4.00 min | 100% B |
| Time 4.30 min | 1% B |
| Time 4.70 min | 1% B |
| Flow rate | 0.8 mL/min |
| Injection volume | 2 μL |
| Agilent | 1200 HPLC/1956 MSD/SEDEX 75 ELSD |
| Ionization Mode | API-ES |
| Polarity | Positive |

EXAMPLE 11

4-(4-Chlorophenoxy)-2-fluoro-5-(2-methoxypyridin-3-yl)-N-(methylsulfonyl)benzamide

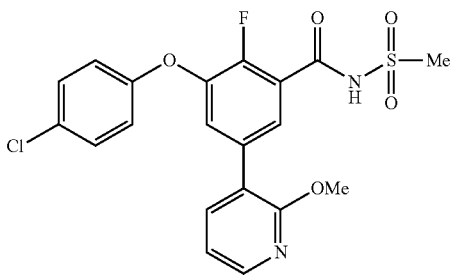 [SMILES: COc1ncccc1-c1cc(Oc2ccc(Cl)cc2)c(F)c(C(=O)NS(C)(=O)=O)c1]

To a mixture of 4-(4-chlorophenoxy)-2-fluoro-5-(2-methoxypyridin-3-yl)benzoic acid (Preparation 30, 236 mg, 0.63 mmol), O-(7-azabenzotriazol-1-yl)-N,N,N',N'-tetramethyluronium hexafluorophosphate (462 mg, 1.21 mmol), N,N-diisopropylethylamine (838 μL, 4.81 mmol) in dichloromethane (40 mL) and dimethylformamide (5.4 mL) which had been stirred at room temperature for 10 minutes was added methyl sulfonamide (151 mg, 1.59 mmol). The reaction was heated at 45° C. for 18 hours under a nitrogen atmosphere. The mixture was cooled to room temperature and concentrated in vacuo to afford a brown residue. The brown residue was partitioned between aqueous hydrochloric acid (0.5 M, 40 mL) and dichloromethane (100 mL). The organic extract was washed with aqueous hydrochloric acid (0.5 M, 2×40 mL), dried over sodium sulfate, filtered and concentrated in vacuo to afford a brown oil (335 mg). The product was purified by flash column chromatography eluting with dichloromethane/methanol (100% to 97%) to afford a yellow gum (91.0 mg). A portion of this material (50 mg) was purified by A-HPLC to afford the title compound as an off-white solid (35.8 mg, 13%):

$^1$H NMR (400 MHz, d$_6$-DMSO): δ 3.33 (s, 3H), 3.75 (s, 3H), 6.88 (d, 1H), 7.04-7.09 (m, 3H), 7.45 (m, 2H), 7.70-7.73 (m, 2H), 8.19 (m, 1H), 12.17 (br s, 1H).

LCMS Rt=3.37 minutes MS m/z 451 [MH]+

Examples 12 to 50 were made via a library protocol employing the following general method using the intermediate prepared in Preparation 24.

General method for the synthesis of 4-(4-chlorophenoxy)-3-aryl-N-(methylsulfonyl)benzamides A solution of cesium carbonate (73.3 mg, 0.225 mmol) in water (113 μL) was added to a solution of 3-bromo-4-(4-chlorophenoxy)-N-(methylsulfonyl)benzamide (Preparation 24, 33.4 mg, 0.0825 mmol) and arylboronic acid (0.075 mmol) in 0.75 mL 1,4-dioxane, followed by 1,1'-bis(di-tert-butylphosphino)ferrocene palladium dichloride (2.41 mg, 0.00370 mmol). The reaction mixture was heated at 60° C. in a nitrogen atmosphere for 14 hours, evaporated to dryness in vacuo and the product purified on a HPLC column with acetonitrile-water (0.1% trifluoroacetic acid) gradient. The equipment used in all cases was Agilent 1200 HPLC/1956 MSD/SEDEX 75 ELSD. The Ionisation mode used was API-ES with positive polarity. All mass spectra, MS (m/z), are [MH]+ unless otherwise stated.

| Ex | NAME | MS |
|---|---|---|
| 12 | 6-(4-chlorophenoxy)-4'-ethoxy-N-(methylsulfonyl)-biphenyl-3-carboxamide | 446 |
| 13 | 6-(4-chlorophenoxy)-N-(methylsulfonyl)-3'-(trifluoromethyl)biphenyl-3-carboxamide | 470 |
| 14 | 4-(4-chlorophenoxy)-3-(3,5-dimethyl-1H-pyrazol-4-yl)-N-(methylsulfonyl)benzamide | 420 |
| 15 | 6-(4-chlorophenoxy)-2'-methoxy-N-(methylsulfonyl)-biphenyl-3-carboxamide | 432 |
| 16 | 4-(4-chlorophenoxy)-3-(6-methoxypyridin-3-yl)-N-(methylsulfonyl)benzamide | 433 |
| 17 | 6-(4-chlorophenoxy)-3'-fluoro-N-(methylsulfonyl)-biphenyl-3-carboxamide | 420 |
| 18 | 6-(4-chlorophenoxy)-2'-fluoro-N-(methylsulfonyl)-biphenyl-3-carboxamide | 420 |
| 19 | 4-(4-chlorophenoxy)-N-(methylsulfonyl)-3-pyridin-3-ylbenzamide | 403 |
| 20 | 6-(4-chlorophenoxy)-3'-ethoxy-N-(methylsulfonyl)-biphenyl-3-carboxamide | 446 |
| 21 | 4-(4-chlorophenoxy)-N-(methylsulfonyl)-3-pyridin-4-ylbenzamide | 403 |
| 22 | 3'-chloro-6-(4-chlorophenoxy)-N-(methylsulfonyl)-biphenyl-3-carboxamide | 436 |
| 23 | 4-(4-chlorophenoxy)-N-(methylsulfonyl)-3-pyrimidin-5-ylbenzamide | 404 |
| 24 | 6-(4-chlorophenoxy)-N-(methylsulfonyl)-2'-(trifluoromethoxy)biphenyl-3-carboxamide | 486 |
| 25 | 6-(4-chlorophenoxy)-4'-cyano-N-(methylsulfonyl)-biphenyl-3-carboxamide | 427 |
| 26 | 6-(4-chlorophenoxy)-3'-cyano-N-(methylsulfonyl)-biphenyl-3-carboxamide | 427 |
| 27 | 4-(4-chlorophenoxy)-3-(1-methyl-1H-pyrazol-5-yl)-N-(methylsulfonyl)benzamide | 406 |
| 28 | 6-(4-chlorophenoxy)-N-(methylsulfonyl)-3'-(trifluoromethoxy)biphenyl-3-carboxamide | 486 |
| 29 | 6-(4-chlorophenoxy)-3'-methoxy-N-(methylsulfonyl)-biphenyl-3-carboxamide | 432 |
| 30 | 4-(4-chlorophenoxy)-N-(methylsulfonyl)-3-(1H-pyrazol-4-yl)benzamide | 392 |
| 31 | 2'-chloro-6-(4-chlorophenoxy)-N-(methylsulfonyl)-biphenyl-3-carboxamide | 436 |
| 32 | 6-(4-chlorophenoxy)-2'-ethoxy-N-(methylsulfonyl)-biphenyl-3-carboxamide | 446 |
| 33 | 6-(4-chlorophenoxy)-2'-cyano-N-(methylsulfonyl)-biphenyl-3-carboxamide | 427 |
| 34 | 4-(4-chlorophenoxy)-3-(2-methylpyridin-4-yl)-N-(methylsulfonyl)benzamide | 417 |
| 35 | 6-(4-chlorophenoxy)-N-(methylsulfonyl)-2'-(trifluoromethyl)biphenyl-3-carboxamide | 470 |
| 36 | 4-(4-chlorophenoxy)-3-(5-fluoro-6-methoxypyridin-3-yl)-N-(methylsulfonyl)benzamide | 451 |
| 37 | 4-(4-chlorophenoxy)-3-(5-chloropyridin-2-yl)-N-(methylsulfonyl)benzamide | 437 |
| 38 | 4-(4-chlorophenoxy)-3-(6-methylpyridin-3-yl)-N-(methylsulfonyl)benzamide | 417 |
| 39 | 4-(4-chlorophenoxy)-3-(6-cyanopyridin-3-yl)-N-(methylsulfonyl)benzamide | 428 |
| 40 | 4-(4-chlorophenoxy)-3-(2-methoxypyrimidin-5-yl)-N-(methylsulfonyl)benzamide | 434 |
| 41 | 4-(4-chlorophenoxy)-N-(methylsulfonyl)-3-(1-propyl-1H-pyrazol-4-yl)benzamide | 434 |
| 42 | 4-(4-chlorophenoxy)-3-(6-methoxy-2-methylpyridin-3-yl)-N-(methylsulfonyl)benzamide | 447 |
| 43 | 6-(4-chlorophenoxy)-N-(methylsulfonyl)-4'-(trifluoromethyl)biphenyl-3-carboxamide | 470 |
| 44 | 4-(4-chlorophenoxy)-3-(5-cyanopyridin-3-yl)-N-(methylsulfonyl)benzamide | 428 |
| 45 | 4-(4-chlorophenoxy)-3-(2-methoxypyridin-4-yl)-N-(methylsulfonyl)benzamide | 433 |
| 46 | 4-(4-chlorophenoxy)-3-(2-methylpyrimidin-5-yl)-N-(methylsulfonyl)benzamide | 418 |
| 47 | 4-(4-chlorophenoxy)-3-(2-methoxypyridin-3-yl)-N-(methylsulfonyl)benzamide | 433 |
| 48 | 4-(4-chlorophenoxy)-3-(1-methyl-1H-pyrazol-4-yl)-N-(methylsulfonyl)benzamide | 406 |
| 49 | 3-(2-aminopyrimidin-5-yl)-4-(4-chlorophenoxy)-N-(methylsulfonyl)benzamide | 419 |
| 50 | 6-(4-chlorophenoxy)-4'-methoxy-N-(methylsulfonyl)-biphenyl-3-carboxamide | 432 |

Examples 51 to 95 were made via a library protocol employing the following general method using the intermediate prepared in Preparation 23.

General Method for the Synthesis of 4-(aryloxy)-3-(2-methoxypyridin-3-yl)-N-(methylsulfonyl)benzamides Step1:
Potassium carbonate (30.3 mg, 0.22 mmol) and 4-fluoro-3-(2-methoxypyridin-3-yl)benzaldehyde (25.4 mg, 0.11 mmol) were added to a solution of alcohol monomer (0.11 mmol). The reaction mixture was heated with shaking at 80° C. for 16 hours. The reaction mixture was filtered and the filtrate evaporated to dryness in vacuo. The residue was purified by preparative HPLC to provide purified aldehyde intermediate.

Step2:
Methyl sulfonamide (9.5 mg, 0.10 mmol) was added to a solution of aldehyde intermediate from step1 (0.11 mmol) in isopropylacetate (0.5 mL). Bis(tert-butylcarbonyloxy)iodobenzene (40.6 mg, 0.10 mmol) and bis[rhodium($\alpha,\alpha,\alpha',\alpha'$-tetramethyl-1,3-benzenedipropionic acid)] (3.8 mg, 0.005 mmol) were added and the reaction mixture shaken at 50° C. for 1 hour. The reaction mixture was evaporated to dryness in vacuo and the product purified on a HPLC column with acetonitrile-water (0.1% trifluoroacetic acid) gradient. The equipment used in all cases was Agilent 1200 HPLC/1956 MSD/SEDEX 75 ELSD. The Ionisation mode used was API-ES with positive polarity.

All mass spectra, MS (m/z), are [MH]+ unless otherwise stated.

| Ex | NAME | MS |
|---|---|---|
| 51 | 4-(2-fluorophenoxy)-3-(2-methoxypyridin-3-yl)-N-(methylsulfonyl)benzamide | 417 |
| 52 | 4-(3-chlorophenoxy)-3-(2-methoxypyridin-3-yl)-N-(methylsulfonyl)benzamide | 433 |
| 53 | 4-(3-chloro-5-fluorophenoxy)-3-(2-methoxypyridin-3-yl)-N-(methylsulfonyl)benzamide | 451 |
| 54 | 4-(3-isopropylphenoxy)-3-(2-methoxypyridin-3-yl)-N-(methylsulfonyl)benzamide | 441 |
| 55 | 4-(3,4-difluorophenoxy)-3-(2-methoxypyridin-3-yl)-N-(methylsulfonyl)benzamide | 435 |
| 56 | 4-(4-cyanophenoxy)-3-(2-methoxypyridin-3-yl)-N-(methylsulfonyl)benzamide | 424 |
| 57 | 4-(3-chloro-5-methoxyphenoxy)-3-(2-methoxypyridin-3-yl)-N-(methylsulfonyl)benzamide | 463 |
| 58 | 3-(2-methoxypyridin-3-yl)-N-(methylsulfonyl)-4-[2-(trifluoromethoxy)phenoxy]benzamide | 483 |
| 59 | 4-(3-fluorophenoxy)-3-(2-methoxypyridin-3-yl)-N-(methylsulfonyl)benzamide | 417 |
| 60 | 4-(4-chloro-3-ethylphenoxy)-3-(2-methoxypyridin-3-yl)-N-(methylsulfonyl)benzamide | 461 |
| 61 | 3-(2-methoxypyridin-3-yl)-N-(methylsulfonyl)-4-[3-(trifluoromethyl)phenoxy]benzamide | 467 |
| 62 | 4-[4-(methoxymethyl)phenoxy]-3-(2-methoxypyridin-3-yl)-N-(methylsulfonyl)benzamide | 443 |
| 63 | 4-[(6-ethylpyridin-3-yl)oxy]-3-(2-methoxypyridin-3-yl)-N-(methylsulfonyl)benzamide | 428 |
| 64 | 4-(4-chloro-2-fluorophenoxy)-3-(2-methoxypyridin-3-yl)-N-(methylsulfonyl)benzamide | 451 |
| 65 | 4-(4-methoxyphenoxy)-3-(2-methoxypyridin-3-yl)-N-(methylsulfonyl)benzamide | 429 |
| 66 | 4-(4-chloro-3-fluorophenoxy)-3-(2-methoxypyridin-3-yl)-N-(methylsulfonyl)benzamide | 451 |
| 67 | 4-(2-ethoxyphenoxy)-3-(2-methoxypyridin-3-yl)-N-(methylsulfonyl)benzamide | 443 |
| 68 | 3-(2-methoxypyridin-3-yl)-N-(methylsulfonyl)-4-[3-(trifluoromethoxy)phenoxy]benzamide | 483 |
| 69 | 4-(3,5-difluorophenoxy)-3-(2-methoxypyridin-3-yl)-N-(methylsulfonyl)benzamide | 435 |

| Ex | NAME | MS |
|---|---|---|
| 70 | 3-(2-methoxypyridin-3-yl)-4-[(6-methoxypyridin-3-yl)oxy]-N-(methylsulfonyl)benzamide | 430 |
| 71 | 4-(3-cyanophenoxy)-3-(2-methoxypyridin-3-yl)-N-(methylsulfonyl)benzamide | 424 |
| 72 | 4-[3-fluoro-5-(trifluoromethyl)phenoxy]-3-(2-methoxypyridin-3-yl)-N-(methylsulfonyl)benzamide | 485 |
| 73 | 3-(2-methoxypyridin-3-yl)-4-(4-methylphenoxy)-N-(methylsulfonyl)benzamide | 413 |
| 74 | 4-(2,3-difluorophenoxy)-3-(2-methoxypyridin-3-yl)-N-(methylsulfonyl)benzamide | 435 |
| 75 | 4-(3-chloro-4-methoxyphenoxy)-3-(2-methoxypyridin-3-yl)-N-(methylsulfonyl)benzamide | 463 |
| 76 | 4-[(5-chloropyridin-2-yl)oxy]-3-(2-methoxypyridin-3-yl)-N-(methylsulfonyl)benzamide | 434 |
| 77 | 4-(4-ethylphenoxy)-3-(2-methoxypyridin-3-yl)-N-(methylsulfonyl)benzamide | 427 |
| 78 | 4-[4-fluoro-3-(trifluoromethyl)phenoxy]-3-(2-methoxypyridin-3-yl)-N-(methylsulfonyl)benzamide | 485 |
| 79 | 4-(2-fluoro-4-methoxyphenoxy)-3-(2-methoxypyridin-3-yl)-N-(methylsulfonyl)benzamide | 447 |
| 80 | 4-(2-ethylphenoxy)-3-(2-methoxypyridin-3-yl)-N-(methylsulfonyl)benzamide | 427 |
| 81 | 4-[2-fluoro-3-(trifluoromethyl)phenoxy]-3-(2-methoxypyridin-3-yl)-N-(methylsulfonyl)benzamide | 485 |
| 82 | 3-(2-methoxypyridin-3-yl)-N-(methylsulfonyl)-4-[2-(trifluoromethyl)phenoxy]benzamide | 467 |
| 83 | 4-(4-ethoxyphenoxy)-3-(2-methoxypyridin-3-yl)-N-(methylsulfonyl)benzamide | 443 |
| 84 | 4-(3-ethoxyphenoxy)-3-(2-methoxypyridin-3-yl)-N-(methylsulfonyl)benzamide | 443 |
| 85 | 4-(3-methoxyphenoxy)-3-(2-methoxypyridin-3-yl)-N-(methylsulfonyl)benzamide | 429 |
| 86 | 4-(2,4-difluorophenoxy)-3-(2-methoxypyridin-3-yl)-N-(methylsulfonyl)benzamide | 435 |
| 87 | 3-(2-methoxypyridin-3-yl)-N-(methylsulfonyl)-4-[4-(trifluoromethyl)phenoxy]benzamide | 467 |
| 88 | 4-(3-chloro-4-cyanophenoxy)-3-(2-methoxypyridin-3-yl)-N-(methylsulfonyl)benzamide | 458 |
| 89 | 4-(3-ethylphenoxy)-3-(2-methoxypyridin-3-yl)-N-(methylsulfonyl)benzamide | 427 |
| 90 | 4-[(5-chloropyridin-3-yl)oxy]-3-(2-methoxypyridin-3-yl)-N-(methylsulfonyl)benzamide | 434 |
| 91 | 4-(4-fluorophenoxy)-3-(2-methoxypyridin-3-yl)-N-(methylsulfonyl)benzamide | 417 |
| 92 | 4-(4-isopropylphenoxy)-3-(2-methoxypyridin-3-yl)-N-(methylsulfonyl)benzamide | 441 |
| 93 | 3-(2-methoxypyridin-3-yl)-N-(methylsulfonyl)-4-[4-(trifluoromethoxy)phenoxy]benzamide | 483 |

EXAMPLE 94

4-(5-chloro-6-cyclopropylpyridin-3-yloxy)-3-(2-methoxypyridin-3-yl)-N-(methylsulfonyl)benzamide

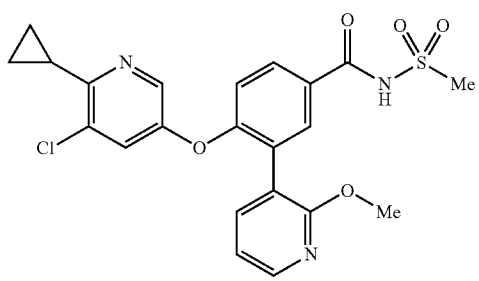 [SMILES: COc1ncccc1-c1cc(C(=O)NS(C)(=O)=O)ccc1Oc1cnc(C2CC2)c(Cl)c1]

To a solution of 4-(5-chloro-6-cyclopropylpyridin-3-yloxy)-3-(2-methoxypyridin-3-yl)benzamide (Preparation 40, 437 mg, 1.10 mmol) in anhydrous tetrahydrofuran (4 mL) under nitrogen was added 1M solution of lithium bis(trimethylsilyl)amide in tetrahydrofuran (4.40 mL, 4.40 mmol). The solution was stirred 30 minutes at room temperature then methane sulfonyl chloride (340 μL, 4.40 mmol) was added and the reaction mixture was stirred 2 hours at room temperature. Water (50 mL) was added and the solution was extracted with ethyl acetate (3×20 mL). The organic layers were combined, dried over magnesium sulfate, filtered and concentrated in vacuo. The crude material was purified by silica gel column chromatography eluting with Feb. 10, 1990 acetic acid/ethyl acetate/dichloromethane to afford the title compound as a white solid (230 mg, 44%).

$^1$H NMR (400 MHz, CDCl3): δ 1.04 (m, 4H), 2.46 (m, 1H), 3.43 (s, 3H), 3.85 (s, 3H), 6.98 (m, 2H), 7.28 (m, 1H), 7.56 (m, 1H), 7.82 (m, 1H), 7.85 (m, 1H), 8.09 (m, 1H), 8.20 (m, 1H), 8.63 (s, 1H).

LCMS rt=2.84 min MS m/z [M−H]−472.02

EXAMPLE 95

4-(4-chloro-3-ethylphenoxy)-N-(methylsulfonyl)-3-(1H-pyrazol-5-yl)benzamide hydrochloride salt

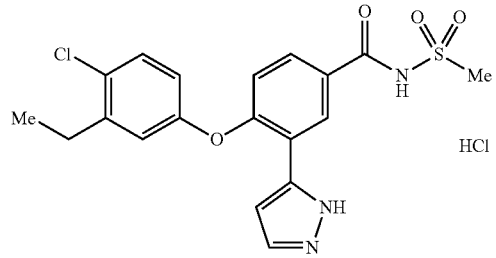 [SMILES: CCc1cc(Oc2ccc(C(=O)NS(C)(=O)=O)cc2-c2ccn[nH]2)ccc1Cl ; Cl]

4-(4-chloro-3-ethylphenoxy)-N-(methylsulfonyl)-3-(1-(tetrahydro-2H-pyran-2-yl)-1H-pyrazol-5-yl)benzamide (Preparation 22, 335 mg, 0.53 mmol) was dissolved in 4M hydrogen chloride in dioxane (5 mL). The reaction mixture was stirred 3 hours then concentrated in vacuo. The crude residue was dissolved in methanol (5 mL) and 12N aqueous solution of hydrochloric acid (0.5 mL) was added. The reaction mixture was stirred for 18 hours at room temperature. The reaction mixture was concentrated to dryness then the residue was azeotroped with methanol (25 mL). The crude solid was triturated with tert-butyl methyl ether (4 mL) and the suspension was filtered off. The filtrate was washed with tert-butyl methyl ether to afford the title compound as a cream coloured solid (HCl salt, 106 mg, 44%).

$^1$H NMR (400 MHz, DMSO-D6): δ 1.15 (m, 3H), 2.68 (m, 2H), 3.38 (s, 3H), 5.20 (bs, 1H), 6.70 (m, 1H), 6.90 (m, 1H), 7.03 (m, 1H), 7.11 (m, 1H), 7.43 (m, 1H), 7.74 (m, 1H), 7.88 (m, 1H), 8.58 (m, 1H), 12.20 (s, 1H).

LCMS rt=3.30 min MS m/z [MH]+420.02

Preparation 1

4-(4-chloro-2-methoxyphenoxy)-3-(2-methoxypyridin-3-yl)benzamide

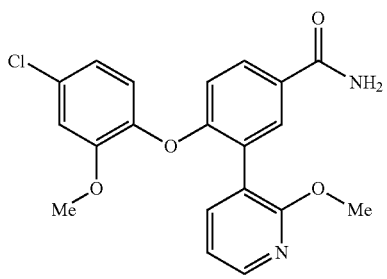 [SMILES: COc1cc(Cl)ccc1Oc1ccc(C(N)=O)cc1-c1cccnc1OC]

Potassium carbonate (0.194 g, 1.40 mmol) was added to a solution of 4-(4-chloro-2-methoxyphenoxy)-3-(2-methoxypyridin-3-yl)benzonitrile (Preparation 2, 0.257 g, 0.701 mmol) in dimethylsulfoxide (6 mL), followed by dropwise addition of 30% hydrogen peroxide aqueous solution (0.422 mL, 14.00 mmol). The mixture was stirred at room temperature for 1 hour, then quenched by addition of saturated aqueous solution of ammonium chloride (20.0 mL) and water (20.0 mL). The pH of the aqueous was adjusted to pH=7 by dropwise addition of saturated aqueous solution of potassium hydrogen sulfate and then extracted with DCM (3×20 mL). The combined organics were washed with brine (50 mL) and filtered to give the title compound as a solid (0.307 g).

$^1$H NMR (400 MHz, d$_6$-DMSO): δ 3.73 (s, 3H), 3.82 (s, 3H), 6.69 (d, 1H), 6.99-7.10 (m, 3H), 7.20 (d, 1H), 7.28 (br. s., 1H), 7.74 (m, 1H), 7.81 (m, 1H), 7.86 (d, 1H), 7.90 (br. s., 1H), 8.19 (m, 1H).

LCMS Rt=2.94 minutes MS m/z 385 [MH]$^+$

Preparation 2

4-(4-chloro-2-methoxyphenoxy)-3-(2-methoxypyridin-3-yl)benzonitrile

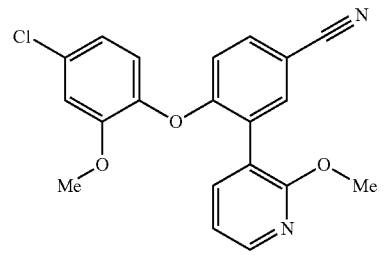 [SMILES: COc1cc(Cl)ccc1Oc1ccc(C#N)cc1-c1cccnc1OC]

Potassium carbonate (0.232 g, 1.68 mmol) and (2-methoxypyridin-3-yl)boronic acid (0.215 g, 1.26 mmol) were added to a solution of 3-bromo-4-(4-chloro-2-methoxyphenoxy)benzonitrile (Preparation 3, 0.284, 0.839 mmol) in dioxane (10 mL). The reaction was degassed three times, then tetrakis(triphenylphosphine)palladium(0) (0.020 g, 0.017 mmol) was added and the mixture was degassed three further times. The resulting mixture was heated at 70° C. over for 72 hours, then the reaction was cooled to room temperature. Then (2-methoxypyridin-3-yl)boronic acid (0.072 g, 0.42 mmol) and tetrakis(triphenylphosphine)palladium(0) (0.020 g, 0.017 mmol) were added and the reaction was heated at 90° C. for 3 hours. The reaction was allowed to cool to room temperature and the solvent removed in vacuo to give a black oil which was absorbed onto silica and purified by silica gel chromatography (Biotage®, SNAP cartridge 50 g, DCM 6CV then 99/1, DCM/MeOH 5 CV and then 9/1, DCM/MeOH 6 CV) to afford the title compound as a white solid (0.265 g).

$^1$H NMR (400 MHz, CDCl$_3$): δ 3.76 (s, 3H), 3.95 (s, 3H), 6.73 (d, 1H), 6.90-7.01 (m, 4H), 7.51 (m, 1H), 7.69 (m, 1H), 7.71 (d, 1H), 8.21 (m, 1H).

LCMS Rt=3.70 minutes MS m/z 366 [MH]$^+$

Preparation 3

3-bromo-4-(4-chloro-2-methoxyphenoxy)benzonitrile

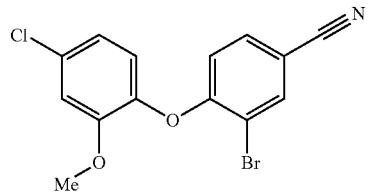 [SMILES: COc1cc(Cl)ccc1Oc1ccc(C#N)cc1Br]

Potassium carbonate (0.784 g, 5.68 mmol) and 3-bromo-4-fluorobenzonitrile (0.378 g, 1.89 mmol) was added to a solution of 4-chloro-2-methoxyphenol (0.300 g, 1.89 mmol) in DMSO (7 mL). The reaction was heated at 80° C. for 2 hours, then cooled and left stirring at room temperature for 18 hours. The reaction was diluted with water (70 mL) and extracted with EtOAc (3×50 mL). The combined organics were washed with 1M NaOH aqueous solution (50 mL), brine (2×70 mL) and then dried over sodium sulfate, filtered and concentrated in vacuo to yield the title compound as an off-white solid (0.625 g).

$^1$H NMR (400 MHz, CDCl$_3$): δ 3.78 (s, 3H), 6.62 (d, 1H), 6.95-7.07 (m, 3H), 7.45 (m, 1H), 7.90 (d, 1H).

Preparation 4

4-[(6-isobutoxypyridin-3-yl)oxy]-3-(2-methoxypyridin-3-yl)benzamide

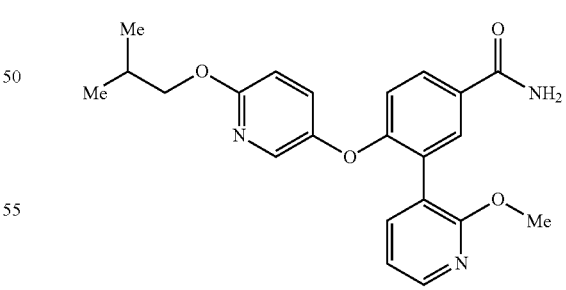

Prepared according to Preparation 1 with 4-[(6-isobutoxypyridin-3-yl)oxy]-3-(2-methoxypyridin-3-yl)benzonitrile (Preparation 5) to afford the title compound (0.308 g).

$^1$H NMR (400 MHz, d$_6$-DMSO): δ 0.96 (d, 6H), 2.01 (m, 1H), 3.79 (s, 3H), 3.99 (d, 2H), 6.83-6.88 (m, 2H), 7.09 (m, 1H), 7.31 (br. s., 1H), 7.44 (m, 1H), 7.74 (m, 1H), 7.84-7.96 (m, 4H), 8.19 (m, 1H).

LCMS Rt=3.16 minutes MS m/z 394 [MH]$^+$

Preparation 5

4-[(6-isobutoxypyridin-3-yl)oxy]-3-(2-methoxypyridin-3-yl)benzonitrile

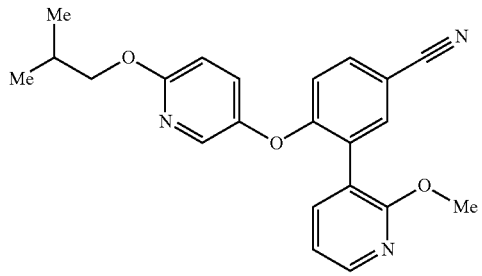 [SMILES: COc1ncccc1-c1cc(C#N)ccc1Oc1ccc(OCC(C)C)nc1]

Potassium carbonate (0.239 g, 1.73 mmol) and (2-methoxypyridin-3-yl)boronic acid (0.162 g, 0.950 mmol) were added to a solution of 3-bromo-4-[(6-isobutoxypyridin-3-yl)oxy]benzonitrile (Preparation 6, 0.300 g, 0.864 mmol) in dioxane (10 mL). The reaction was degassed three times. Tetrakis(triphenylphosphine)palladium(0) (0.010 g, 0.009 mmol) was added and the mixture was degassed three times more. The mixture was heated at 60° C. for 24 hours, then allowed to cool to room temperature and filtered through arbocel, washing with DCM/MeOH (1/1, 50 mL). The combined filtrates were concentrated in vacuo. The residue was absorbed onto silica and purified by silica gel chromatography (Biotage®, SNAP cartridge 50 g, gradient from 5 to 10% EtOAc in heptane 6, then 10% EtOAc in Heptane) to yield the title compound as a solid (0.257 g).

$^1$H NMR (400 MHz, CDCl$_3$): δ 1.02 (d, 6H), 2.09 (dt, 1H), 3.92 (s, 3H), 4.04 (d, 2H), 6.76 (d, 1H), 6.85 (d, 1H), 7.00 (m, 1H), 7.28 (m, 1H), 7.58 (m, 1H) 7.60 (m, 1H), 7.65 (d, 1H), 7.91 (d, 1H), 8.23 (m, 1H).

LCMS Rt=3.74 minutes MS m/z 376 [MH]$^+$

Preparation 6

3-bromo-4-[(6-isobutoxypyridin-3-yl)oxy]benzonitrile

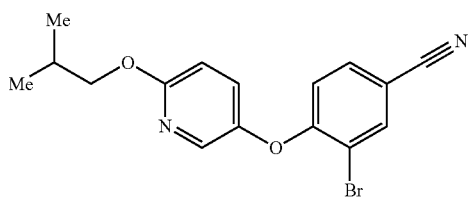 [SMILES: CC(C)COc1ccc(Oc2ccc(C#N)cc2Br)cn1]

Potassium carbonate (0.622, 4.50 mmol) and 6-isobutoxy-pyridin-3-ol (Preparation 7, 0.251 g, 1.50 mmol) were added to a solution of 3-bromo-4-fluorobenzonitrile (0.300 g, 1.50 mmol) in DMSO (7 mL). The reaction was heated at 80° C. for a total of 4 hours and then allowed to cool to room temperature. The mixture was diluted with water (50 mL) and extracted with DCM (3×30 mL). The combined organics were washed with brine (2×50 mL), filtered and concentrated in vacuo to yield the title compound as a solid (0.508 g).

$^1$H NMR (400 MHz, CDCl$_3$): δ 1.04 (d, 6H), 2.05-2.16 (m, 1H), 4.07 (d, 2H), 6.77 (d, 1H), 6.82 (d, 1H), 7.34 (m, 1H), 7.50 (m, 1H), 7.93 (d, 1H), 7.98 (d, 1H).

LCMS Rt=3.81 minutes MS m/z 347 [MH]$^+$

Preparation 7

6-isobutoxypyridin-3-ol

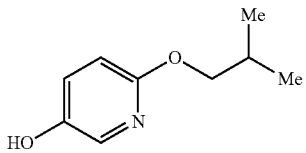 [SMILES: CC(C)COc1ccc(O)cn1]

A solution of nBuLi in hexane (2.5 M, 70 mL, 0.176 mol) was added to a solution of 5-bromo-2-isobutoxy-pyridine (Preparation 8, 27 g, 0.117 mol) in THF (300 mL) under a nitrogen atmosphere at −78° C. After stirring for 1 hour, trimethyl borate (18.3 g, 0.176 mol) was added. The mixture was stirred at 0° C. for 1 hour then diluted with 3N NaOH (15 mL) and hydrogen peroxide (30%, 175 mL). The resulting mixture was stirred at room temperature for 1 hour and extracted with EtOAc (3×500 mL). The combined organics were washed with saturated aqueous sodium sufite (3×500 mL), brine (300 mL) then dried over sodium sulfate and filtered. The filtrate was concentrated in vacuo to yield the crude product that was purified by silica gel chromatography (petroleum ether/EtOAc 100:1 to 10:1) to give the title compound as an off-white solid (6.0 g).

$^1$H NMR (400 MHz, d$_6$-DMSO): δ 0.92 (d, 6H), 1.90-2.00 (m, 1H), 3.88 (d, 2H), 6.62 (d, 1H), 7.14 (m, 1H), 7.62 (d, 1H), 9.22 (s, 1H)

Preparation 8

5-Bromo-2-isobutoxy-pyridine

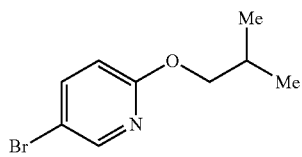 [SMILES: CC(C)COc1ccc(Br)cn1]

To 2-methyl-propan-1-ol (10 g, 0.41 mol) was added NaH (60%, 8.2 g, 0.204 mol) portionwise under a nitrogen atmosphere at room temperature over 10 minutes. The mixture was refluxed for 30 minutes. A solution of 5-bromo-2-fluoro-pyridine (24 g, 0.136 mol) in DMF (400 mL) was added dropwise and the mixture refluxed for 18 hours. The reaction mixture was then diluted with water (1 L) and extracted with EtOAc (3×500 mL). The combined organics were washed with brine (3×300 mL), dried over sodium sulfate, filtered and concentrated in vacuo. The crude residue obtained was purified by flash column chromatography eluting with petroleum ether to yield the title compound as a colourless oil (27 g).

Preparation 9

3-bromo-4-(4-chloro-3-ethyl phenoxy)benzaldehyde

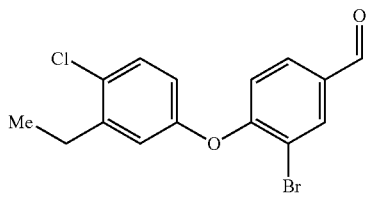 [SMILES: CCc1cc(Oc2ccc(C=O)cc2Br)ccc1Cl]

To a solution of DMSO (10 mL) was added 4-chloro-3-ethylphenol (5 g, 31.9 mmol), followed by potassium carbonate (11.0 g, 79.8 mmol). After 1 minute, 3-bromo-4-fluorobenzaldehyde (6.48 g, 31.9 mmol) was added in one portion, and the reaction heated to 50° C. for 5 hours. The reaction was diluted by addition of 1M NaOH solution (100 mL), and extracted into ethyl acetate (3×100 mL). The combined organic layers were then dried over magnesium sulfate, filtered, and concentrated in vacuo to leave a crude pink oil. The crude material was purified by column chromatography (silica), eluting with 4:1 heptane:ethyl acetate, the title compound as a white solid (8.22 g, 76%).

$^1$HNMR (400 MHz, CDCl3): δ 1.23 (t, 3H), 3.76 (q, 2H), 6.82 (d, 1H), 6.88 (d, 1H), 6.95 (s, 1H), 7.37 (d, 1H), 7.73 (d, 1H), 8.17 (s, 1H), 9.90 (1H).

LCMS (4.5 min) Rt=3.94 minutes, No mass ion observed.

Preparation 10

4-(4-chloro-3-ethylphenoxy)-3-(1-(tetrahydro-2H-pyran-2-yl)-1H-pyrazol-5-yl)benzaldehyde

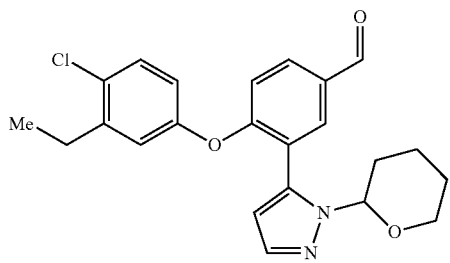 [SMILES: CCc1cc(Oc2ccc(C=O)cc2-c2ccnn2C2CCCCO2)ccc1Cl]

3-bromo-4-(4-chloro-3-ethylphenoxy)benzaldehyde (Preparation 9, 336 mg, 1.08 mmol), 1-(tetrahydro-2H-pyran-2-yl)-5-(4,4,5,5-tetramethyl-1,3,2-dioxaborolan-2-yl)-1H-pyrazole (300 mg, 1.08 mmol) and cesium carbonate (1.05 g, 3.24 mmol) were suspended in dioxane (4 mL) and water (2 mL). The suspension was degassed 40 minutes with nitrogen then tetrakis-triphenylphosphine palladium (62 mg, 0.054 mmol) was added and the reaction mixture was heated for 18 hours at 75° C. The solution was concentrated in vacuo to a quarter of its volume then diluted with water (20 mL) and extracted by ethyl acetate (3×20 mL). The organic layers were combined, dried over magnesium sulfate, filtered and concentrated in vacuo. The crude residue was purified by silica gel column chromatography eluting with a gradient from 15% diethyl ether in heptane to 50% diethyl ether in heptane to afford the title compound as a colourless oil (218 mg, 49%).

$^1$H NMR (400 MHz, CDCl3): δ 1.21 (m, 3H), 1.54 (m, 2H), 1.74 (m, 1H), 1.90 (m, 1H), 2.06 (m, 1H), 2.55 (m, 1H), 2.73 (m, 2H), 3.50 (m, 1H), 4.06 (m, 1H), 5.18 (m, 1H), 6.42 (m, 1H), 6.79 (m, 1H), 6.89 (m, 1H), 7.00 (m, 1H), 7.33 (m, 1H), 7.65 (m, 1H), 7.88 (m, 1H), 8.06 (m, 1H), 9.97 (s, 1H).

LCMS rt=3.76 min MS m/z [MH-tetrahydropyranyl]+ 327.11

Preparation 11

4-(4-chlorophenoxy)-3-(3-methoxypyridin-2-yl)benzamide

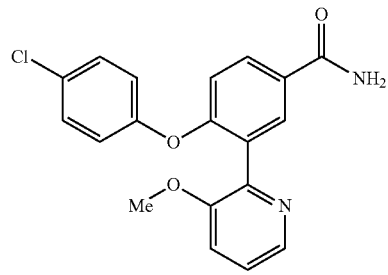 [SMILES: COc1cccnc1-c1cc(C(N)=O)ccc1Oc1ccc(Cl)cc1]

Potassium carbonate (0.143 g, 1.0 mmol) was added to a solution of 4-(4-chlorophenoxy)-3-(3-methoxypyridin-2-yl)benzonitrile (Preparation 12, 0.175 g, 0.52 mmol) in DMSO, followed by dropwise addition of 30% hydrogen peroxide aqueous solution (3.1 mL, 3.1 mmol). The mixture was stirred at room temperature for 1.5 hours. The reaction was quenched with aqueous potassium hydrogen sulfate (30 mL) and extracted with DCM (3×30 mL). The organic layer was washed with water (2×30 mL), dried over magnesium sulfate and concentrated in vacuo to afford the title compound as a white solid (0.269 g). This was taken to the next step without further purification.

LCMS Rt=2.58 minutes MS m/z 355 [MH]$^+$

Preparation 12

4-(4-chlorophenoxy)-3-(3-methoxypyridin-2-yl)benzonitrile

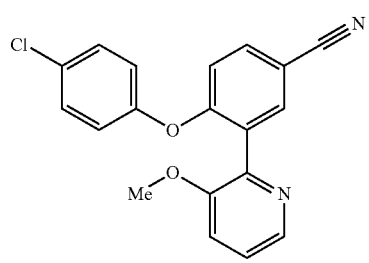 [SMILES: COc1cccnc1-c1cc(C#N)ccc1Oc1ccc(Cl)cc1]

Tetrakis(triphenylphosphine)palladium(0) (0.325 g, 0.28 mmol) and 1M aqueous solution of sodium hydrogen carbonate (5.6 mL, 5.6 mmol) were added to 4-(4-chlorophenoxy)-3-(4,4,5,5-tetramethyl-1,3,2-dioxaborolan-2-yl)benzonitrile (Preparation 13, 1.0 g, 2.8 mmol) and 2-bromo-3-methoxypyridine (0.528 g, 2.8 mmol) in 1,4-dioxane (30 mL). The mixture was heated at 85° C. for 18 hours under a nitrogen atmosphere, then cooled, diluted with water (30 mL) and extracted with EtOAc (3×30 mL). The organic layer was washed with water (2×30 mL), dried over magnesium sulfate, filtered and concentrated in vacuo to afford an oil. The crude product was purified by silica gel chromatography eluting with 10 to 80% tert-butyl dimethyl ether in heptane to yield the title compound as a white solid (0.175 g).

$^1$H NMR (400 MHz, CDCl$_3$): δ 3.70 (s, 3H), 6.90 (m, 3H), 7.25 (m, 4H), 7.58 (m, 1H), 7.79 (d, 1H), 8.27 (m, 1H).

LCMS Rt=3.29 minutes MS m/z 337 [MH]$^+$

Preparation 13

4-(4-chlorophenoxy)-3-(4,4,5,5-tetramethyl-1,3,2-dioxaborolan-2-yl)benzonitrile

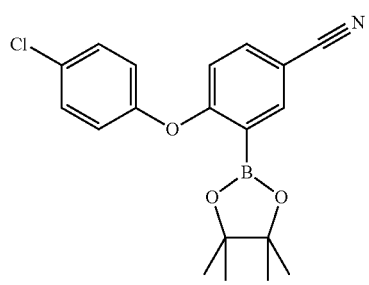 [SMILES: CC1(C)OB(c2cc(C#N)ccc2Oc2ccc(Cl)cc2)OC1(C)C]

[1,1'-Bis(diphenylphosphino)ferrocene]dichloropalladium(II) (0.530 g, 0.65 mmol) and potassium acetate (1.91 g, 19.4 mmol) were added to a solution of 3-bromo-4-(4-chlorophenoxy)benzonitrile (Preparation 14, 2.0 g, 6.48 mmol) and 4,4,4',4',5,5,5',5'-octamethyl-2,2'-bi-1,3,2-dioxaborolane (2.46 g, 9.7 mmol) in DMSO (30 mL). The mixture was heated at 100° C. under a nitrogen atmosphere for 2 hours then cooled to room temperature, poured onto water (50 mL) and extracted with EtOAc (4×50 mL). The organic layer was washed with water (2×30 mL), dried over magnesium sulfate, filtered and concentrated in vacuo to afford a black solid which was purified by silica gel chromatography eluting with 20 to 50% EtOAc in Heptane to yield the title compound as a white solid (2.13 g).

$^1$H NMR (400 MHz, CDCl$_3$): δ 1.24 (s, 12H), 6.89 (m, 1H), 7.27 (d, 1H), 7.50 (m, 1H), 7.65 (d, 1H), 7.75 (m, 1H), 7.93 (d, 1H), 8.22 (d, 1H),

LCMS Rt=3.55 minutes MS m/z mass ion not observed

Preparation 14

3-bromo-4-(4-chlorophenoxy)benzonitrile

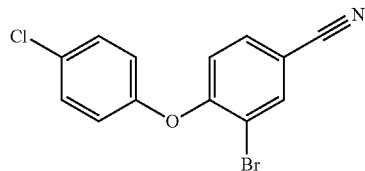 [SMILES: N#Cc1ccc(Oc2ccc(Cl)cc2)c(Br)c1]

A mixture of 3-bromo-4-fluorobenzonitrile (1.60 g, 8.00 mmol), 4-chlorophenol (1.028 g, 8 mmol) and potassium carbonate (2.487 g, 24 mmol) in DMSO (20 mL) was stirred for 18 hours at room temperature under a nitrogen atmosphere. The reaction was diluted with aqueous ammonium chloride (50 mL) and extracted with EtOAc (3×30 mL). The combined organic extract was washed with water (2×30 mL) and dried over magnesium sulfate, filtered and concentrated in vacuo to afford the title compound as a white solid (2.47 g).

$^1$H NMR (400 MHz, CDCl$_3$): δ 6.85 (d, 1H), 7.00 (d, 2H), 7.38 (d, 2H), 7.51 (m, 1H), 7.92 (d, 1H).

LCMS Rt=3.90 minutes MS m/z mass ion not observed

Preparation 15

4-(4-chloro-2-methoxyphenoxy)-2-fluoro-5-(2-methoxypyridin-3-yl)benzoic acid lithium salt

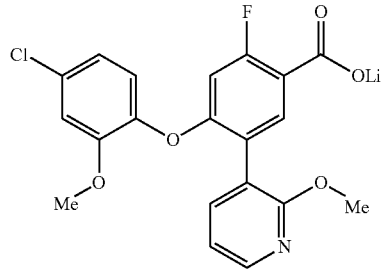

Aqueous lithium hydroxide solution (1M, 0.57 mL, 0.57 mmol) was added to a solution of methyl 4-(4-chloro-2-methoxyphenoxy)-2-fluoro-5-(2-methoxypyridin-3-yl)benzoate (Preparation 16, 0.0477 mg, 0.114 mmol) in THF (2.3 mL) and stirred for 72 hours at room temperature under a nitrogen atmosphere. The reaction was then concentrated in vacuo to afford the title compound as a white solid (0.070 g).

$^1$H NMR (400 MHz, d$^6$-DMSO): δ 3.73 (s, 3H), 3.78 (s, 3H), 6.28 (d, 1H), 6.96-6.98 (m, 2H), 7.02 (m, 1H), 7.15 (d, 1H), 7.50 (d, 1H), 7.63 (m, 1H), 8.13 (m, 1H).

LCMS Rt=3.26 minutes MS m/z 402 [M−H]$^−$

Preparation 16

Methyl 4-(4-chloro-2-methoxyphenoxy)-2-fluoro-5-(2-methoxypyridin-3-yl)benzoate

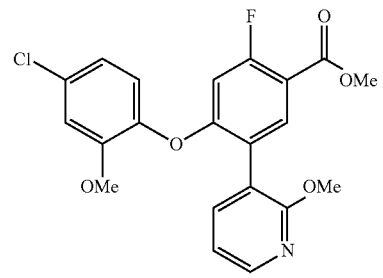 [SMILES: COC(=O)c1cc(-c2cccnc2OC)c(Oc2ccc(Cl)cc2OC)cc1F]

Prepared according to Preparation 2 using methyl 5-bromo-4-(4-chloro-2-methoxyphenoxy)-2-fluorobenzoate (Preparation 17, 0.165 g, 0.423 mmol) and (2-methoxypyridin-3-yl)boronic acid mono hydrate (0.109 g, 0.637 mmol) with an extra addition of water (0.5 mL) and heating for 18 hours at 50° C. The crude product was purified by silica gel chromatography eluting with 0 to 10% EtOAc in DCM to afford the title compound as a clear gum (47.7 mg).

$^1$H NMR (400 MHz, CDCl$_3$): δ 3.76 (s, 3H), 3.90 (s, 3H), 3.92 (s, 3H), 6.39 (d, 1H), 6.93-6.98 (m, 4H), 7.66 (m, 1H), 7.96 (d, 1H), 8.18 (m, 1H).

LCMS Rt=3.68 minutes MS m/z 418 [MH]$^+$

Preparation 17

Methyl 5-bromo-4-(4-chloro-2-methoxyphenoxy)-2-fluorobenzoate

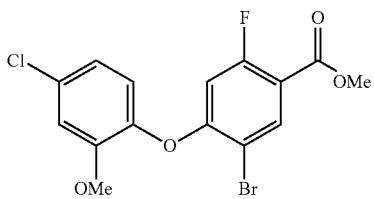 [SMILES: COC(=O)c1cc(Br)c(Oc2ccc(Cl)cc2OC)cc1F]

Prepared according to Preparation 3 with 4-chloro-2-methoxyphenol (0.13 mL, 1.07 mmol) and methyl 5-bromo-2,4-difluorobenzoate (Preparation 18, 255 mg, 1.02 mmol) at room temperature for 18 hours. The crude product was purified by silica gel chromatography eluting with 5% EtOAc in Heptane to afford the title compound as a white solid (0.165 g).

$^1$H NMR (400 MHz, CDCl$_3$): δ 3.77 (s, 3H), 3.91 (s, 3H), 6.31 (d, 1H), 6.97-7.05 (m, 3H), 8.25 (d, 1H).

LCMS Rt=3.73 minutes MS m/z 389 [MH]$^+$

Preparation 18 (Prov1 Prep 10)

Methyl 5-bromo-2,4-difluorobenzoate

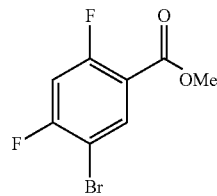 [SMILES: COC(=O)c1cc(Br)c(F)cc1F]

Concentrated hydrochloric acid (10.4 mL, 127 mmol) was slowly added to a mixture of 5-bromo-2,4-difluorobenzoic acid (0.999 g, 4.21 mmol) in methanol (26 mL). The mixture was heated at 95° C. for 18 hours. The reaction was cooled and then concentrated in vacuo. The residue was diluted with water (50 mL) and extracted with EtOAc (3×50 mL). The combined organic extract was washed with brine (2×50 mL), dried over sodium sulfate, filtered and concentrated in vacuo to afford a brown oil (0.847 g). The crude product was purified by silica gel chromatography (Biotage®, 100 g SNAP cartridge, 5 to 50% EtOAc in Heptane) to afford the title compound as clear crystalline solid (0.544 g).

$^1$H NMR (400 MHz, CDCl$_3$): δ 3.95 (s, 3H), 6.98 (m, 1H), 8.21 (t, 1H).

LCMS Rt=2.95 minutes

Preparation 19

3-(2-methoxypyridin-3-yl)-4-phenoxybenzamide

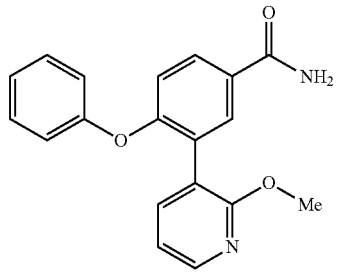 [SMILES: COc1ncccc1-c1cc(C(N)=O)ccc1Oc1ccccc1]

A solution of 30% aqueous hydrogen peroxide (1 mL, 7.6 mmol) was added dropwise to a suspension of 3-(2-methoxypyridin-3-yl)-4-phenoxybenzonitrile (Preparation 20, 0.23 g, 0.76 mmol) and potassium carbonate (0.64 g, 4.6 mmol) in DMSO (3 mL). The reaction mixture was stirred for 2 hours at room temperature, then quenched with aqueous sodium thiosulfate solution (10% w/v, 10 mL) and extracted with EtOAc (50 mL). The organic layer was dried over sodium sulfate and the solvent removed in vacuo to afford the title compound as a pale yellow solid (0.2 g).

$^1$H NMR (400 MHz, CDCl$_3$): δ 3.78 (s, 3H), 6.85 (m, 4H), 7.02 (t, 1H), 7.25 (t, 2H), 7.55 (d, 1H), 7.85 (d, 1H), 7.88 (s, 1H), 8.06 (d, 1H).

LCMS Rt=2.26 minutes MS m/z 321 [MH]$^+$

Preparation 20

3-(2-methoxypyridin-3-yl)-4-phenoxybenzonitrile

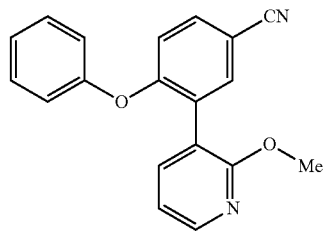 [SMILES: COc1ncccc1-c1cc(C#N)ccc1Oc1ccccc1]

A mixture of 3-bromo-4-phenoxybenzonitrile (Preparation 21, 0.21 g, 0.7 mmol), (2-methoxypyridin-3-yl)boronic acid (0.2 g, 1.1 mmol) and sodium hydrogen carbonate (0.19 g, 2.1 mmol) was suspended in dioxane (10 mL) and water (3 mL). The reaction mixture was degassed for 10 minutes. Tetrakis(triphenylphosphine)palladium (0) (0.050 g, 0.07 mmol) was added and the mixture heated at 100° C. for 1 hour. After the reaction was allowed to cool to room temperature, the reaction was partitioned between EtOAc (50 mL) and water (15 mL). The organic layer was filtered through a pad of celite and the solvent removed in vacuo to provide a crude brown solid. The crude material was purified by silica gel chromatography eluting with 30% EtOAc in Heptane to afford the title compound as a yellow solid (0.23 g).

$^1$H NMR (400 MHz, CDCl$_3$): δ 3.80 (s, 3H), 6.85 (d, 1H), 6.95 (m, 3H), 7.05 (t, 1H), 7.12 (m, 2H), 7.50 (m, 2H), 7.80 (s, 1H), 8.15 (m, 1H),

LCMS Rt=3.17 minutes MS m/z 304 [MH]$^+$

Preparation 21

3-Bromo-4-phenoxybenzonitrile

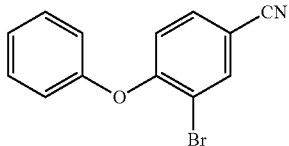 [SMILES: N#Cc1ccc(Oc2ccccc2)c(Br)c1]

3-Bromo-4-fluorobenzonitrile (0.5 g, 2.4 mmol) was added to a suspension of phenol (0.23 g, 2.4 mmol) and potassium carbonate (0.67 g, 4.8 mmol) in DMSO (2 mL) and the reaction mixture was allowed to stir at room temperature for 18 hours. The reaction mixture was diluted with EtOAc (30 mL) and washed with water (3×30 mL). The combined organics were dried over sodium sulfate and concentrated in vacuo to afford the title compound (0.59 g).

$^1$H NMR (400 MHz, CDCl$_3$): δ 6.82 (d, 1H), 7.05 (m, 2H), 7.22 (m, 1H), 7.42 (m, 2H), 7.50 (m, 1H), 7.95 (s, 1H).

LCMS Rt=3.55 minutes MS m/z 274 [MH]$^+$

Preparation 22

4-(4-chloro-3-ethylphenoxy)-N-(methylsulfonyl-1)-3-(1-(tetrahydro-2H-pyran-2-yl)-1H-pyrazol-5-yl)benzamide

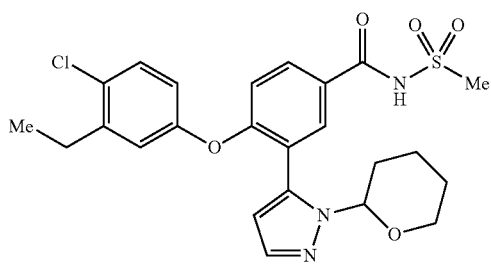 [SMILES: CCc1cc(Oc2ccc(C(=O)NS(C)(=O)=O)cc2-c2ccnn2C2CCCCO2)ccc1Cl]

A solution of 4-(4-chloro-3-ethylphenoxy)-3-(1-(tetrahydro-2H-pyran-2-yl)-1H-pyrazol-5-yl)benzaldehyde (Preparation 10, 218 mg, 0.53 mmol), methanesulfonamide (51 mg, 0.53 mmol) and di-(pivaloyl)iodobenzene (323 mg, 0.80 mmol) in isopropyl acetate (4 mL) was degassed 5 minutes with nitrogen then bis[rhodium(α,α,α',α'-tetramethyl-1,3-benzene dipropionic acid)] (20 mg, 0.026 mmol) was added and the reaction mixture was stirred 2 hours at room temperature. The solution was concentrated in vacuo then purified by silica gel column chromatography eluting with 5% ethyl acetate in heptane then 5% methanol in dichloromethane to afford the title compound as yellow foam (335 mg, 125%).

LCMS rt=3.64 min MS m/z [MH]+504.12

Preparation 23

4-fluoro-3-(2-methoxypyridin-3-yl)benzaldehyde

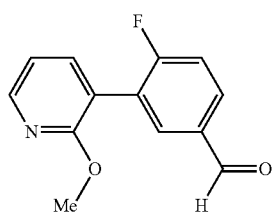 [SMILES: COc1ncccc1-c1cc(C=O)ccc1F]

A mixture of 3-bromo-4-fluorobenzaldehyde (1.0 g, 4.9 mmol), (2-methoxypyridin-3-yl)boronic acid (1.2 g, 7 mmol) and sodium hydrogen carbonate (1.5 g, 15 mmol) was stirred in dioxane (20 mL) and water (8 mL). The mixture was degassed for 10 minutes, then tetrakis(triphenylphosphine)palladium (0) (0.130 g, 0.1 mol) was added. The reaction mixture was stirred at 100° C. for 1 hour then cooled and concentrated in vacuo. The resulting residue was partitioned between EtOAc (60 mL) and water (15 mL), dried over sodium sulfate and concentrated in vacuo to afford the crude product, which was purified by silica gel chromatography eluting with 20% EtOAc in heptane to afford the title compound as a white solid (0.85 g).

$^1$H NMR (400 MHz, CDCl$_3$): δ 3.90 (s, 3H), 7.05 (m, 1H), 7.15 (m, 1H), 7.60 (m, 1H), 7.95 (m, 2H), 8.12 (d, 1H), 10.02 (s, 1H).

LCMS Rt=2.27 minutes MS m/z 232 [MH]$^+$

Preparation 24

3-Bromo-4-(4-chlorophenoxy)-N-(methylsulfonyl)benzamide

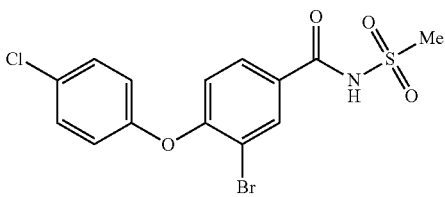 [SMILES: CS(=O)(=O)NC(=O)c1ccc(Oc2ccc(Cl)cc2)c(Br)c1]

A mixture of 3-bromo-4-(4-chlorophenoxy)-benzoic acid (Preparation 29, 19 g, 58 mmol), methanesulfonamide (9.67 g, 102 mmol), EDCI (19.33 g, 101.5 mmol) and DMAP (12.34 g, 101.5 mmol) in DMF (200 mL) was stirred at room temperature for 16 hours. The reaction mixture was evaporated in vacuo, diluted with DCM (500 mL), washed with aqueous 1M HCl (3×100 mL), dried over sodium sulfate, filtered and concentrated in vacuo. The residue was purified by silica gel chromatography eluting with 50% petroleum ether in EtOAc to afford the title compound as a white solid (5.4 g).

$^1$H NMR (400 MHz, d$_6$-DMSO) δ 3.36 (s, 3H); 7.07 (m, 1H); 7.13 (m, 2H); 7.51 (m, 2H); 7.95 (m, 1H); 8.34 (m, 1H)

Preparation 25

3-Bromo-4-[(5-chloro-6-isopropoxypyridin-3-yl)oxy]benzonitrile

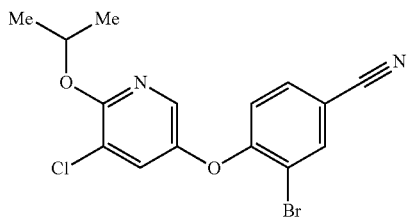 [SMILES: CC(C)Oc1ncc(Oc2ccc(C#N)cc2Br)cc1Cl]

To a solution of 5-chloro-6-isopropoxypyridin-3-ol (Preparation 35, 350 mg, 1.87 mmol) in dimethyl sulfoxide (2 mL) was added 3-bromo-4-fluorobenzonitrile (333 mg, 1.87 mmol) and potassium carbonate (386 mg, 2.80 mmol). The reaction was stirred at 50° C. for 4 hours and then partitioned between water (100 mL) and EtOAc. The aqueous phase was separated and extracted with EtOAc (2×25 mL). The combined organic extracts were dried over anhydrous sodium sulfate, filtered and concentrated in vacuo to afford the title compound as a colourless oil which crystallised on standing (920 mg) and which was used without further purification in the next step.

$^1$H NMR (400 MHz, CDCl$_3$): δ 1.40 (m, 6H), 5.35 (m, 1H), 6.80 (m, 1H), 7.43 (s, 1H), 7.55 (m, 1H), 7.85 (s, 1H), 7.95 (s, 1H).

LCMS Rt=3.93 minutes MS m/z 325 [MH–C$_3$H$_7$]$^+$

Preparation 26

4-[(5-Chloro-6-isopropoxypyridin-3-yl)oxy]-3-(2-methoxypyridin-3-yl)benzonitrile

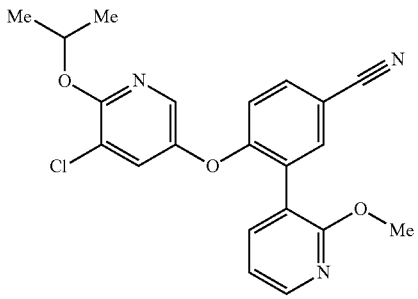 [SMILES: COc1ncccc1-c1cc(C#N)ccc1Oc1cnc(OC(C)C)c(Cl)c1]

To a solution of 3-bromo-4-[(5-chloro-6-isopropoxypyridin-3-yl)oxy]benzonitrile (Preparation 25, 638 mg, 1.74 mmol) and 2-methoxy-3-pyridylboronic acid (265 mg, 1.74 mmol) in dioxan (10.5 mL) was added a 1 M aqueous solution of sodium carbonate (5.2 mL, 5.21 mmol). The reaction was sparged with nitrogen before the addition of tetrakis(triphenylphosphine)palladium(0) (200 mg, 0.17 mmol). The reaction mixture was heated to 100° C. and stirred for 16 hours and then concentrated in vacuo The residue was partitioned between water (30 mL) and EtOAc (25 mL). The aqueous phase was separated and extracted with EtOAc (2×25 mL).

The combined organic extracts were dried over anhydrous sodium sulfate, filtered and concentrated in vacuo to afford a yellow oil which was purified by silica gel column chromatography, eluting with 9:1 heptane/EtOAc. Fractions containing product were combined and concentrated in vacuo to obtain the title compound as a colourless oil (534 mg, 60%).

$^1$H NMR (400 MHz, CDCl$_3$): δ 1.40 (m, 6H), 3.90 (s, 3H), 5.30 (m, 1H), 6.90 (m, 1H), 6.95 (m, 1H), 7.35 (m, 1H), 7.50 (m, 2H), 7.65 (m, 1H), 7.80 (m, 1H), 8.20 (m, 1H).

LCMS Rt=4.19 minutes MS m/z 396 [MH]$^+$

Preparation 27

4-[(5-Chloro-6-isopropoxypyridin-3-yl)oxy]-3-(2-methoxypyridin-3-yl)benzamide

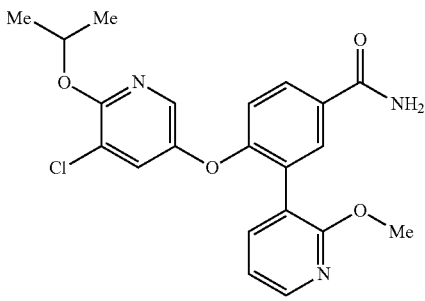 [SMILES: COc1ncccc1-c1cc(C(N)=O)ccc1Oc1cnc(OC(C)C)c(Cl)c1]

To a solution of 4-[(5-chloro-6-isopropoxypyridin-3-yl)oxy]-3-(2-methoxypyridin-3-yl)benzonitrile (Preparation 26, 534 mg, 1.35 mmol) in DMSO (10.0 mL) was added potassium carbonate (560 mg, 4.05 mmol) and a 30% aqueous solution of hydrogen peroxide (690 μL, 6.74 mmol). The reaction was stirred at room temperature for 1 hour. Water (50 mL) was added to the reaction mixture resulting in the formation of a white precipitate. The precipitate was filtered, washed with water (50 mL) and dried in vacuo to obtain the title compound as a colourless solid (436 mg, 85%), which was used without further purification in the next step.

$^1$H NMR (400 MHz, CDCl$_3$): 1.40 (m, 6H), 3.85 (s, 3H), 5.25 (m, 1H), 6.95 (m, 2H), 7.35 (m, 1H), 7.58 (m, 1H), 7.80 (m, 3H), 8.20 (m, 1H).

LCMS Rt=3.03 minutes MS m/z 414 [MH]$^+$

Preparation 28

Methyl-3-bromo-4-(4-chlorophenoxy)-benzoate

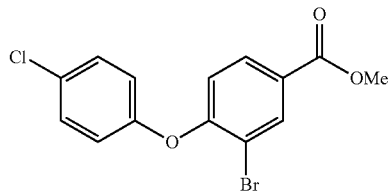 [SMILES: COC(=O)c1ccc(Oc2ccc(Cl)cc2)c(Br)c1]

To a solution of methyl-3-bromo-4-fluoro benzoate (20 g, 86 mmol) and 4-chlorophenol (11.0 g, 171 mmol) in dimethylsulfoxide (500 mL) was added potassium tert-butoxide (19.3 g, 171 mmol) and the reaction mixture was stirred at 120° C. for 16 hours and then poured into 500 mL of water and extracted with dichloromethane (3×100 mL). The combined extracts were dried over anhydrous sodium sulfate, filtered and evaporated in vacuo. The residue was purified via column chromatography on silica gel (1:1 petroleum ether: EtOAc) to yield 18 g (55 mmol) of 3-bromo-4-(4-chlorophenoxy)-benzoic acid and 2 g of the title compound.

$^1$H NMR (CDCl$_3$, 400 MHz): δ 3.90 (s, 3H); 6.86 (m, 1H); 6.97 (m, 2H); 7.35 (m, 2H); 7.91 (m, 1H); 8.32 (m, 1H).

Preparation 29

3-Bromo-4-(4-chlorophenoxy)-benzoic acid

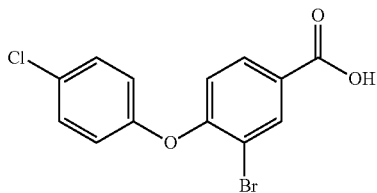 [SMILES: O=C(O)c1ccc(Oc2ccc(Cl)cc2)c(Br)c1]

To a solution of methyl-3-bromo-4-(4-chlorophenoxy)-benzoate (Preparation 28, 2 g, 6 mmol) in 40 mL methanol was added sodium hydroxide (0.486 g, 11.7 mmol) in 10 mL water. The reaction mixture was stirred at 50° C. for 16 hours and then acidified to pH 4 with 1M hydrochloric acid, stirred for 1 hour, filtered and dried in vacuo to afford the title compound (1.53 g, 78%).

$^1$H NMR (CDCl$_3$, 400 MHz): δ 6.87 (m, 1H); 6.99 (m, 2H); 7.36 (m, 2H); 7.95 (m, 1H); 8.37 (m, 1H).

Preparation 30

4-(4-Chlorophenoxy)-2-fluoro-5-(2-methoxypyridin-3-yl)benzoic acid lithium salt

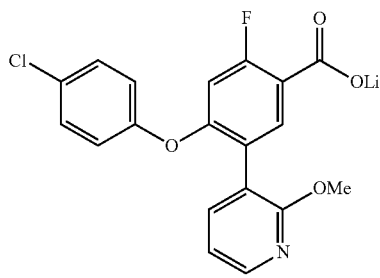

To a solution of methyl 4-(4-chlorophenoxy)-2-fluoro-5-(2-methoxypyridin-3-yl)benzoate (Preparation 31, 194 mg, 0.50 mmol) in THF (10 mL) was added aqueous lithium hydroxide solution (1M, 2.51 mL, 2.51 mmol) and the mixture stirred for 72 hours at room temperature under a nitrogen atmosphere. The reaction was then concentrated in vacuo to afford the title compound as a white solid (236 mg, 100%).

$^1$H NMR (400 MHz, d$_6$-DMSO): δ 3.70 (s, 3H), 6.63 (d, 1H), 6.92 (d, 2H), 6.99 (m, 1H), 7.34 (d, 2H), 7.51 (d, 1H), 7.56 (m, 1H), 8.10 (m, 1H).

LCMS Rt=3.33 minutes MS m/z 374 [MH]$^+$

Preparation 31

Methyl 4-(4-chlorophenoxy)-2-fluoro-5-(2-methoxypyridin-3-yl)benzoate

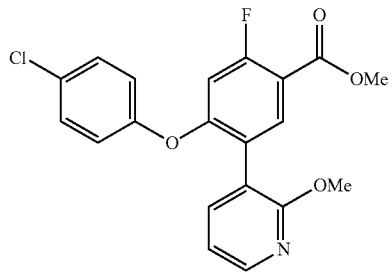 [SMILES: COC(=O)c1cc(-c2cccnc2OC)c(Oc2ccc(Cl)cc2)cc1F]

To a stirred solution of methyl 5-bromo-4-(4-chlorophenoxy)-2-fluorobenzoate (Preparation 32, 199 mg, 0.55 mmol) in dioxane (10 mL) and water (0.5 mL) was added potassium carbonate (158 mg, 1.14 mmol) and 2-methoxypyridin-3-ylboronic acid mono hydrate (147 mg, 0.86 mmol). The reaction was degassed three times followed by the addition of tetrakis(triphenylphosphine)palladium(0) (13.2 mg, 0.012 mmol). The reaction was degassed three times and heated at 50° C. overnight under a nitrogen atmosphere. The reaction was cooled to room temperature, concentrated in vacuo to afford a brown residue. The residue was partitioned between EtOAc (25 mL) and water (25 mL). The aqueous phase was extracted with EtOAc (2×25 mL). The combined organic extracts were washed with water (25 mL), brine (25 mL), dried over sodium sulfate, filtered and concentrated in vacuo to afford brown oil (383 mg). The oil was then purified by flash column chromatography using the Biotage System™ (50 g silica column, eluting with DCM). Fractions containing product were combined and concentrated in vacuo to afford the title compound as a grey oil (194 mg, 91%).

$^1$H NMR (400 MHz, CDCl$_3$): δ 3.86 (s, 3H), 3.92 (s, 3H), 6.59 (d, 1H), 6.94-6.98 (m, 3H), 7.32 (d, 2H), 7.56 (m, 1H), 7.95 (d, 1H), 8.18 (m, 1H).

LCMS Rt=3.78 minutes MS m/z 388 [MH]$^+$

Preparation 32

Methyl 5-bromo-4-(4-chlorophenoxy)-2-fluorobenzoate

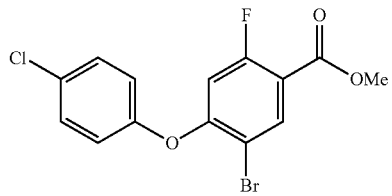 [SMILES: COC(=O)c1cc(Br)c(Oc2ccc(Cl)cc2)cc1F]

A mixture of 4-chlorophenol (94.7 mg, 0.74 mmol), methyl 5-bromo-2,4-difluorobenzoate (Preparation 18, 168 mg, 0.67 mmol), and potassium carbonate (277 mg, 2.01 mmol) in dimethyl sulfoxide (3 mL) was stirred for 16 hours at room temperature under a nitrogen atmosphere. The reaction was diluted with water (30 mL) and extracted with EtOAc (3×20 mL). The combined organic extracts were successively washed with aqueous sodium hydroxide solution (1.0 M, 20 mL), brine (2×30 mL), dried over sodium sulfate, filtered and concentrated in vacuo to afford the title compound as a colourless oil (199 mg, 83%).

$^1$H NMR (400 MHz, CDCl$_3$): δ 3.92 (s, 3H), 6.52 (d, 1H), 7.01 (d, 2H), 7.40 (d, 2H), 8.23 (d, 1H).

LCMS Rt=3.79 minutes MS m/z 359 [MH]$^+$

Preparation 33

3-Chloro-2-isopropoxypyridine

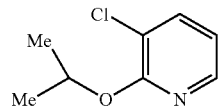 [SMILES: CC(C)Oc1ncccc1Cl]

To a 3-necked flask equipped with a dropping funnel, thermometer and a condenser was added sodium hydride (64.10 g; 1.07 mol) followed by THF (1.65 L). The suspension was cooled to 5° C. and iso-propanol (128 mL; 1.07 mol) was added dropwise over 50 minutes. Upon complete addition the ice bath was removed and the mixture was brought to room temperature and was left to stir for 1 hour. Then 2,3-dichloropyridine (154.6 g; 1.11 mol) was added and the reaction mixture brought to a gentle reflux and left to stir for 18 hours. The reaction mixture was cooled to 5-10° C. and was carefully quenched with brine:water mixture (50:50; 100 mL) followed by water (300 mL). The aqueous layer was extracted with EtOAc (3×600 mL), the organic layers combined and washed with brine, dried (MgSO$_4$), filtered and evaporated to give the title compound as a dark red oil (164.1 g; 89%).

$^1$H NMR (400 MHz, CDCl$_3$): δ 1.40 (6H, d), 5.36 (1H, m), 6.80 (1H, m), 7.6 (1H, m), 8.05 (1H, m).

LCMS Rt=3.09 minutes MS m/z 130 [M−iPr]$^+$

Preparation 34

3-Chloro-2-isopropoxy-5-(4,4,5,5-tetramethyl-1,3,2-dioxaborolan-2-yl)pyridine

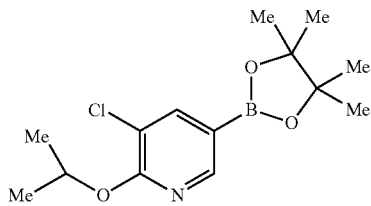 [SMILES: CC(C)Oc1ncc(B2OC(C)(C)C(C)(C)O2)cc1Cl]

A round bottom flask was charged with 3-chloro-2-isopropoxypyridine (Preparation 33, 154.1 g; 897.9 mmol), bispinacolatodiboron (273.6 g, 1.077 mol) and 4,4-di-tert-butyl-2,2-dipyridyl (2.45 g; 8.97 mmol) in heptane (1.55 L). The reaction mixture was cycled between vacuum and nitrogen 6 times over 15 minutes. Di-mu-methanolatodiiridium(Ir-Ir)-cycloocta-1,5-diene (1:2) (2.45 g; 4.49 mmol) was added and the reaction left to stir for 18 hours under nitrogen. Once all starting materials have been consumed the reaction mixture was cooled to 5° C. and quenched with methanol (70 mL). After complete addition the reaction mixture was evaporated to dryness to afford the title compound as a red viscous oil, which was used in the next step without further purification.

$^1$H NMR (400 MHz, CDCl$_3$): δ 1.20 (6H, d), 1.30-1.35 (12H, s), 4.40 (1H, m), 7.96 (1H, m), 8.38 (1H, m).

LCMS Rt=4.55 minutes

Preparation 35

5-Chloro-6-isopropoxypyridin-3-ol

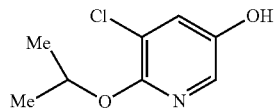

To a solution of 3-chloro-2-isopropoxy-5-(4,4,5,5-tetramethyl-1,3,2-dioxaborolan-2-yl)pyridine (Preparation 34, 297.6 g, 897.9 mmol) in acetic acid:water (2.2 L:1.0 L) at 0° C. was added peracetic acid (191 mL; 1.077 mol) and the reaction was allowed to warm gradually to room temperature. After 4 hours the reaction was complete and was quenched with 0.5 M solution of sodium thiosulfate (225 mL). The resulting dark solution was evaporated to dryness and the residue was passed through a plug of silica (flushed with neat heptane gradually up to 10% EtOAc:heptane) to remove base line boronate salts. The filtrate evaporated to give a pale yellow viscous oil which contained 8% of the wrong regioisomer. Further column chromatography was performed (SiO$_2$ 80 g/1.5 Kg using 30% EtOAc in heptane as eluent). Relevant fractions were evaporated to give a pale yellow solid which was triturated with heptane, dried under suction to give the title compound as a white solid.

$^1$H NMR (400 MHz, CDCl$_3$): δ 1.38 (6H, d), 4.20 (1H, m), 7.25 (1H, m), 7.70 (1H, m).

LCMS Rt=2.15 minutes MS m/z 186 [M−H]$^−$

Preparation 36

3-Chloro-2-cyclopropylpyridine

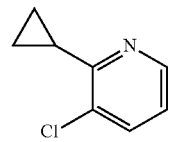

3-Chloro-2-bromopyridine (5.0 g, 26 mmol) and potassium phosphate tribasic (19.3 g, 90.9 mol) were suspended in toluene (40.0 mL) and water (2.0 mL). The mixture was sonicated for 10 minutes, then cyclopropylboronic acid (1.12 g, 13.0 mmol), palladium diacetate (0.093 g, 0.414 mol) and tricyclohexylphosphine (0.243 g, 0.867 mol) were added to the reaction mixture, which was heated into a pre heated DrySyn® at 100° C., under a nitrogen atmosphere for 2 hours. Then cyclopropylboronic acid (1.12 g, 13.0 mmol), palladium diacetate (0.093 g, 0.41 mol) and tricyclohexylphosphine (0.243 g, 0.87 mol) were added to the reaction mixture and the mixture was stirred for 2 hours. Then cyclopropylboronic acid (1.12 g, 13.0 mmol), palladium diacetate (0.093 g, 0.41 mol) and tricyclohexylphosphine (0.243 g, 0.87 mol) were added to the reaction mixture and the mixture was stirred for 2 hours more. The reaction mixture was then left to stir at room temperature for 16 hours. The reaction mixture was diluted with EtOAc (40.0 mL) and water (40.0 mL) and was filtered on a pad of Arbocel® under a stream of nitrogen. The organic layer was separated and washed with a 10% solution of aqueous citric acid (3×25.0 mL), followed by an aqueous hydrochloric acid solution (3×1.0 M, 20.0 mL). The organic layer was discarded and the aqueous layer basified again with careful addition of a saturated aqueous solution of sodium hydrogen carbonate (100.0 mL). The product was extracted with tert-butyl methyl ether (3×20.0 mL). The combined organics were washed once more with a 10% solution of aqueous citric acid (25.0 mL). The organic layer was then dried over sodium sulfate, filtered, and concentrated in vacuo to yield the title compound as a pale brown oil (2.45 g, 62%).

$^1$H NMR (400 MHz, d$_6$-DMSO): δ 0.94-1.01 (m, 4H), 2.40-2.48 (m, 1H), 7.13-7.16 (m, 1H), 7.78-7.81 (m, 1H), 8.33-8.34 (m, 1H).

LCMS Rt=2.27 minutes MS m/z 154 [MH]$^+$

Preparation 37

5-Chloro-6-cyclopropyl pyridin-3-ol

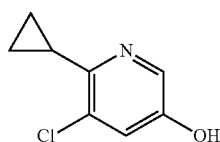 [SMILES: Oc1cnc(C2CC2)c(Cl)c1]

A round bottom flask was charged with 3-chloro-2-cyclopropylpyridine (Preparation 36, 0.475 g; 3.092 mmol), bis(pinacolato)diboron (0.980 g, 3.86 mol) and 4,4-di-tert-butyl-2,2-dipyridyl (0.025 g; 0.093 mmol) in heptane (1.55 L). The reaction mixture was cycled between vacuum and nitrogen 6 times over 15 minutes. Di-μ-methanolatodiiridium(Ir—Ir)-cycloocta-1,5-diene (1:2) (0.063 g; 0.093 mmol) was then added and the reaction stirred for 18 hours under nitrogen atmosphere at room temperature. The reaction mixture was evaporated to dryness to afford a red viscous oil. The resulting oil was dissolved in acetone (10.0 mL) and cooled to 0° C. with an ice bath. Then potassium peroxymonosulfate (2.55 g, 4.15 mmol) in water (10.0 mL) was added dropwise to the mixture and stirred at this temperature for 1 hour. The reaction was then diluted in tert-butyl methyl ether (25.0 mL) and washed with brine (3×25.0 mL). The organic layer was then dried over sodium sulfate, filtered, and concentrated in vacuo. The resulting crude product was purified with silica gel chromatography eluting with 0 to 30% EtOAc in heptane to yield the title compound as a pale yellow solid (0.220 g, 1.28 mmol, 42%).

$^1$H NMR (400 MHz, d$_6$-DMSO): δ 0.81-0.85 (m, 2H), 0.86-0.91 (m, 2H), 2.26-2.32 (m, 1H), 7.19 (d, 1H), 7.94-7.95 (d, 1H), 10.05 (s, 1H).

Preparation 38

3-bromo-4-(5-chloro-6-cyclopropylpyridin-3-yloxy)benzonitrile

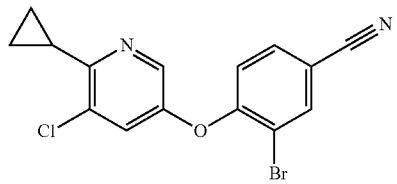 [SMILES: N#Cc1ccc(Oc2cnc(C3CC3)c(Cl)c2)c(Br)c1]

5-chloro-6-cyclopropylpyridin-3-ol (250 mg, 1.47 mmol), 3-bromo-4-fluorobenzonitrile (Preparation 37, 295 mg, 1.47 mmol) and potassium carbonate (611 mg, 4.42 mmol) were suspended in dimethylsulfoxide (6 mL). The reaction mixture was stirred at 5 hours at 50° C. then water (60 mL) was added and the suspension was extracted by ethyl acetate (3×30 mL). The organic layers were combined, washed with brine (3×15 mL), dried over magnesium sulfate, filtered and concentrated under vacuum to afford the title compound as a clear oil which solidified on standing (485 mg, 94%).

$^1$H NMR (400 MHz, CDCl3): δ 1.07 (m, 4H), 2.50 (m, 1H), 6.88 (m, 1H), 7.34 (m, 1H), 7.55 (m, 1H), 7.94 (m, 1H), 8.16 (m, 1H).

LCMS rt=3.80 min MS m/z [MH]+348.94

Preparation 39

4-(5-chloro-6-cyclopropyl pyridin-3-yloxy)-3-(2-methoxypyridin-3-yl)benzonitrile

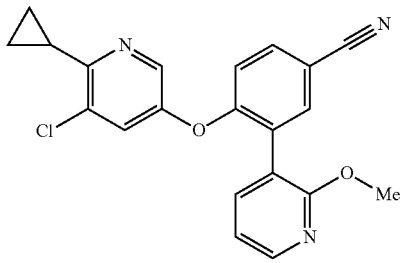 [SMILES: COc1ncccc1-c1cc(C#N)ccc1Oc1cnc(C2CC2)c(Cl)c1]

3-bromo-4-(5-chloro-6-cyclopropylpyridin-3-yloxy)benzonitrile (Preparation 38, 485 mg, 1.37 mmol), 2-methoxypyridin-3-ylboronic acid (233 mg, 1.53 mmol) and cesium carbonate were suspended in dioxane (6 mL) and water (3 mL). The suspension was degassed 20 minutes with nitrogen then tetrakis-triphenylphosphinepalladium (80 mg, 0.07 mmol) were added and the reaction mixture was heated overnight at 75° C. The solution was concentrated in vacuo to a quarter of the volume then diluted with water (20 mL) and extracted with ethyl acetate (3×20 mL). The organic layers were combined, dried over magnesium sulfate, filtered and concentrated in vacuo. The crude material was purified by silica gel column chromatography to afford the title compound as a foam (478 mg, 91%).

¹H NMR (400 MHz, CDCl3): δ 1.04 (m, 4H), 2.46 (m, 1H), 3.86 (s, 3H), 6.97 (m, 2H), 7.27 (m, 1H), 7.54 (m, 1H), 7.61 (m, 1H), 7.67 (m, 1H), 8.08 (m, 1H), 8.20 (m, 1H).

LCMS rt=3.75 min MS m/z [MH]+378.03

Preparation 40

4-(5-chloro-6-cyclopropyl pyridin-3-yloxy)-3-(2-methoxypyridin-3-yl)benzamide

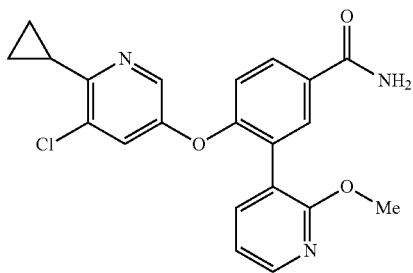 [SMILES: COc1ncccc1-c1cc(C(N)=O)ccc1Oc1cnc(C2CC2)c(Cl)c1]

To a solution of 4-(5-chloro-6-cyclopropylpyridin-3-yloxy)-3-(2-methoxypyridin-3-yl)benzonitrile (Preparation 39, 478 mg, 1.27 mmol) in dimethyl sulfoxide (5 mL) was added potassium carbonate (1.05 g, 7.62 mmol) followed by a 30% aqueous solution of hydrogen peroxide (650 µL, 6.35 mmol). The reaction was stirred 1 hour at room temperature. Water (50 mL) was added and the solution was extracted by ethyl acetate (3×20 mL). The organic layers were combined, dried over magnesium sulfate, filtered and concentrated in vacuo. The crude material was purified by silica gel chromatography eluting with 3% methanol in dichloromethane to afford the title compound as a white solid (528 mg, 87%).

¹H NMR (400 MHz, CDCl3): δ 1.02 (m, 4H), 2.44 (m, 1H), 3.82 (s, 3H), 5.66 (bs, 1H), 6.01 (bs, 1H), 7.96 (m, 2H), 7.25 (m, 1H), 7.56 (m, 1H), 7.79 (m, 1H), 7.83 (m, 1H), 8.07 (m, 1H), 8.17 (m, 1H).

LCMS rt=3.12 min MS m/z [MH]+396.02

The ability of the compounds of formula (I) to block the Nav1.7 (or SCN9A) channel were measured using the assay described below.

Cell Line Construction and Maintenance

Human Embryonic Kidney (HEK) cells were transfected with an hSCN9A construct using lipofectamine reagent (Invitrogen), using standard techniques. Cells stably expressing the hSCN9A constructs were identified by their resistance to G-418 (400 µg/ml). Clones were screened for expression using the whole-cell voltage-clamp technique.

Cell Culture

HEK cells stably transfected with hSCN9A were maintained in DMEM medium supplemented with 10% heat-inactivated fetal bovine serum and 400 µg/ml G-418 in an incubator at 37° C. with a humidified atmosphere of 10% $CO_2$. For HTS, cells were harvested from flasks by trypsinization and replated in an appropriate multi-well plate (typically 96 or 384 wells/plate) such that confluence would be achieved within 24 hours of plating. For electrophysiological studies, cells were removed from the culture flask by brief trypsinization and re-plated at low density onto glass cover slips. Cells were typically used for electrophysiological experiments within 24 to 72 hours after plating.

Electrophysiological Recording

Cover slips containing HEK cells expressing hSCN9A were placed in a bath on the stage of an inverted microscope and perfused (approximately 1 ml/minutes) with extracellular solution of the following composition: 138 mM NaCl, 2 mM $CaCl_2$, 5.4 mM KCl, 1 mM $MgCl_2$, 10 mM glucose, and 10 mM HEPES, pH 7.4, with NaOH. Pipettes were filled with an intracellular solution of the following composition: 135 mM CsF, 5 mM CsCl, 2 mM $MgCl_2$, 10 mM EGTA, 10 mM HEPES, pH 7.3 with NaOH, and had a resistance of 1 to 2 megaohms. The osmolarity of the extracellular and intracellular solutions was 300 mOsm/kg and 295 mOsm/kg, respectively. All recordings were made at room temperature (22-24° C.) using AXOPATCH 200B amplifiers and PCLAMP software (Axon Instruments, Burlingame, Calif.).

hSCN9A currents in HEK cells were measured using the whole-cell configuration of the patch-clamp technique (Hamill et al., 1981). Uncompensated series resistance was typically 2 to 5 mega ohms and >85% series resistance compensation was routinely achieved. As a result, voltage errors were negligible and no correction was applied. Current records were acquired at 20 to 50 KHz and filtered at 5 to 10 KHz.

HEK cells stably transfected with hSCN9A were viewed under Hoffman contrast optics and placed in front of an array of flow pipes emitting either control or compound-containing extracellular solutions. All compounds were dissolved in dimethyl sulfoxide to make 10 mM stock solutions, which were then diluted into extracellular solution to attain the final concentrations desired. The final concentration of dimethyl sulfoxide (<0.3% dimethyl sulfoxide) was found to have no significant effect on hSCN9A sodium currents. The voltage-dependence of inactivation was determined by applying a series of depolarizing prepulses (8 sec long in 10 mV increments) from a negative holding potential. The voltage was then immediately stepped to 0 mV to assess the magnitude of the sodium current. Currents elicited at 0 mV were plotted as a function of prepulse potential to allow estimation of the voltage at which 50% of the channels were inactivated (midpoint of inactivation or V1/2). Compounds were tested for their ability to inhibit hSCN9A sodium channels by activating the channel with a 20 msec voltage step to 0 mV following an 8 second conditioning prepulse to the empirically determined V1/2. Compound effect (% inhibition) was determined by difference in current amplitude before and after application of test compounds. For ease of comparison, "estimated IC-50" ($EIC_{50}$) values were calculated from single point electrophysiology data by the following equation, (tested concentration, uM)×(100-% inhibition/% inhibition). Inhibition values<20% and >80% were excluded from the calculation.

Electrophysiological assays were conducted with PatchXpress 7000 hardware and associated software (Molecular Devices Corp). All assay buffers and solutions were identical to those used in conventional whole-cell voltage clamp experiments described above. hSCN9A cells were grown as above to 50%-80% confluency and harvested by trypsinization. Trypsinized cells were washed and resuspended in extracellular buffer at a concentration of $1×10^6$ cells/ml. The onboard liquid handling facility of the PatchXpress was used for dispensing cells and application of test compounds. Determination of the voltage midpoint of inactivation was as described for conventional whole-cell recordings. Cells were then voltage-clamped to the empirically determined V1/2 and current was activated by a 20 msec voltage step to 0 mV.

Electrophysiological assays were also conducted using the Ionworks Quattro automated electrophysiological platform (Molecular Devices Corp). Intracellular and extracellular solutions were as described above with the following changes, 120 µg/ml amphotericin was added to the intracellular solution to perforate the membrane and allow electrical access to the cells. hSCN9A cells were grown and harvested as for PatchXpress and cells were resuspended in extracellular solution at a concentration of $1\times10^6$ cells/ml. The onboard liquid handling facility of the Ionworks Quattro was used for dispensing cells and application of test compounds. A voltage protocol was then applied that comprised of a voltage step to fully inactivate the sodium channels, followed by a brief hyperpolarized recovery period to allow partial recovery from inactivation for unblocked sodium channels, followed by a test depolarized voltage step to assess magnitude of inhibition by test compound. Compound effect was determined based on current amplitude difference between the pre-compound addition and post-compound addition scans.

Compounds of the Examples were tested in the assays described above and found to have the Nav1.7 $EIC_{50}$ (uM) values specified in the table below. All data are derived from the PatchXpress assay unless expressly stated otherwise.

| Ex | EIC50 |
|---|---|
| 1 | 2.7 |
| 2 | 0.22 |
| 3 | 0.99 |
| 4 | 4.5 |
| 5 | 0.90 |
| 6 | 1.3 |
| 7 | 0.066 |
| 8 | 0.049 |
| 9 | 0.11 |
| 10 | 0.94 |
| 11 | 0.10 |
| 12 | 3.5 |
| 13 | 24 (IW) |
| 14 | >3 |
| 15 | 0.18 |
| 16 | 0.91 |
| 17 | 13 (IW) |
| 18 | 0.57 |
| 19 | 28 (IW) |
| 20 | 0.82 |
| 21 | 4.6 |
| 22 | 15 (IW) |
| 23 | 2.8 |
| 24 | 0.50 |
| 25 | 10 (IW) |
| 26 | 17 (IW) |
| 27 | >3 |
| 28 | 16 (IW) |
| 29 | 0.57 |
| 30 | 18 (IW) |
| 31 | 0.27 |
| 32 | 0.12 |
| 33 | 0.29 |
| 34 | 8.6 |
| 35 | 8.0 |
| 36 | 3.9 |
| 37 | 0.34 |
| 38 | >3 |
| 39 | 1.1 |
| 40 | 69 (IW) |
| 41 | >3 |
| 42 | 7.5 |
| 43 | 0.63 |
| 44 | 17 (IW) |
| 45 | 2.0 |
| 46 | 151 (IW) |
| 47 | 0.092 |
| 48 | 9.8 |
| 49 | >3 |
| 50 | 0.73 |
| 51 | 1.7 |
| 52 | 0.46 |
| 53 | 0.12 |
| 54 | 0.12 |
| 55 | 0.44 |
| 56 | 2.4 |

-continued

| Ex | EIC50 |
|---|---|
| 57 | 0.66 |
| 58 | >1 |
| 59 | 0.37 |
| 60 | 0.018 |
| 61 | 0.066 |
| 62 | 1.2 |
| 63 | 3.9 |
| 64 | 0.54 |
| 65 | 0.64 |
| 66 | 0.098 |
| 67 | 2.8 |
| 68 | 0.083 |
| 69 | 0.44 |
| 70 | 2.2 |
| 71 | 2.5 |
| 72 | 0.10 |
| 73 | 0.17 |
| 74 | 1.9 |
| 75 | 0.31 |
| 76 | >1 |
| 77 | <1 |
| 78 | 0.15 |
| 79 | 2.4 |
| 80 | >1 |
| 81 | 1.1 |
| 82 | >1 |
| 83 | 0.49 |
| 84 | 0.49 |
| 85 | 0.64 |
| 86 | 1.1 |
| 87 | 0.086 |
| 88 | 2.5 |
| 89 | 0.16 |
| 90 | 1.4 |
| 91 | 0.68 |
| 92 | 0.038 |
| 93 | 0.066 |
| 94 | 0.40 |
| 95 | 0.10 |

The ability of compounds of formula (I) to block the Nav1.5 (or SCN5A) channel can also be measured using an assay analogous to that described above but replacing the SCN9A gene with the SCN5A gene. All other conditions remain the same including the same cell line and conditions for cell growth. The estimated IC50s are determined at the half inactivation for Nav1.5. These results can be compared to the $EIC_{50}$ value at the Nav1.7 channel to determine the selectivity of a given compound for Nav1.7 vs Nav1.5.

The invention claimed is:
1. A compound of formula (I):

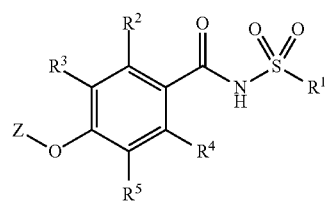

or a pharmaceutically acceptable salt thereof, wherein:
Z is a group selected from naphthyl, phenyl and $Het^1$, said group being optionally independently substituted by one to three substituents selected from $Y^1$ and $Y^2$;
$Y^1$ and $Y^2$ are independently selected from F; Cl; CN; $(C_1-C_8)$alkyl, optionally substituted by $(C_3-C_8)$cycloalkyl or one to three F; $(C_3-C_8)$cycloalkyl, optionally substituted by one to three F; $NR^7R^8$; $(C_1-C_8)$alkyloxy, optionally independently substituted by one to three $R^9$; $(C_3-C_8)$cycloalkyloxy; phenyl, optionally independently substituted by one to three $R^{10}$; $Het^2$; and $Het^3$; wherein $(C_3-C_8)$cycloalkyloxy may be optionally fused to a phenyl ring or may be independently substituted by one to three $R^{10}$;

$R^1$ is $(C_1-C_6)$alkyl or $(C_3-C_8)$cycloalkyl, each of which is optionally substituted by one to three F;

$R^2$, $R^3$, $R^4$ are independently H, F, Cl or —OCH$_3$;

$R^5$ is phenyl optionally substituted by one to three substituents independently selected from CN, Cl, F and $R^6$; or $Het^3$;

$R^6$ is a group selected from $(C_1-C_6)$alkyl and $(C_1-C_6)$alkyloxy, wherein each group is optionally substituted, valency permitting, by one to five F;

$R^7$ and $R^8$ are independently H; $(C_1-C_8)$alkyl, optionally independently substituted by one to three $R^{11}$; $(C_3-C_8)$cycloalkyl; or 'C-linked' $Het^2$; wherein (C3-C8)cycloalkyl may be optionally fused to a phenyl ring or may be independently substituted by one to three $R^{10}$; or $R^7$ and $R^8$, taken together with the nitrogen atom to which they are attached, form a saturated, bridged, 7- to 9-membered ring;

$R^9$ is F; $(C_1-C_6)$alkyloxy; $(C_3-C_8)$cycloalkyl, optionally substituted by one to three F; $Het^1$; or phenyl, optionally independently substituted by one to three $R^6$;

$R^{10}$ is F, Cl or $R^6$;

$R^{11}$ is F; $(C_1-C_6)$alkyloxy; $(C_3-C_8)$cycloalkyl, optionally substituted by one to three F; 'C-linked' $Het^1$; or phenyl, optionally independently substituted by one to three $R^6$;

$Het^1$ is a 6-, 9- or 10-membered heteroaryl comprising one to three nitrogen atoms;

$Het^2$ is a 3- to 8-membered saturated monoheterocycloalkyl comprising one or two ring members selected from —$NR^{12}$— and —O—, said monoheterocycloalkyl being optionally substituted on a ring carbon atom by one to three substituents independently selected from F, $(C_1-C_6)$alkyl, $(C_1-C_4)$alkyloxy$(C_0-C_4)$alkylene and $(C_3-C_8)$cycloalkyl;

$Het^3$ is a 5- or 6-membered heteroaryl comprising one to three nitrogen atoms, said heteroaryl being optionally substituted by one to three substituents selected from F, Cl, CN and $R^6$; and $R^{12}$ is H, $(C_1-C_6)$alkyl or $(C_3-C_8)$cycloalkyl, wherein $(C_1-C_6)$alkyl and $(C_3-C_8)$cycloalkyl are optionally substituted by one to three F; or, when $Het^2$ is 'N-linked', is absent.

2. A compound according to claim 1 wherein Z is phenyl optionally independently substituted by one to three substituents selected from $Y^1$ and $Y^2$.

3. A compound according to claim 1 wherein wherein Z is phenyl optionally independently substituted by one or two substituents selected from $Y^1$ and $Y^2$.

4. A compound according to claim 1 wherein Z is phenyl para-substituted by $Y^2$.

5. A compound according to claim 1 wherein Z is a 6-membered heteroaryl comprising one to three nitrogen atoms, said heteroaryl being optionally independently substituted by one to three substituents selected from $Y^1$ and $Y^2$.

6. A compound according to claims 1 wherein Z is pyridyl optionally independently substituted by one to three substituents selected from $Y^1$ and $Y^2$.

7. A compound according to claim 1 wherein Z is pyridyl optionally independently substituted by one or two substituents selected from $Y^1$ and $Y^2$.

8. A compound according to claim 1 wherein Z is pyridyl optionally independently substituted by one or two substituents selected from $Y^1$ and $Y^2$ and wherein said pyridyl is orientated as below:

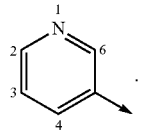

9. A compound according to claim 8 wherein said pyridyl is 2-substituted or, where di-substituted, 2- and 3-substituted.

10. A compound according to claim 1 wherein $R^1$ is $(C_1-C_4)$alkyl or $(C_3-C_6)$cycloalkyl.

11. A compound according to claim 1 wherein $R^2$, $R^3$ and $R^4$ are independently H or F.

12. A compound according to claim 1 wherein $R^5$ is (i) phenyl optionally substituted by one or two substituents independently selected from CN, Cl, F and $R^6$; or (ii) a 5- or 6-membered heteroaryl comprising one or two nitrogen atoms, said heteroaryl being optionally substituted by one or two substituents selected from F, Cl, CN and $R^6$.

13. A compound according to claim 1 wherein $R^5$ is (i) phenyl optionally substituted by CN, Cl, F or $R^6$; or (ii) a heteroaryl selected from pyrazolyl, pyridyl or pyrimidinyl, said heteroaryl being optionally substituted by $(C_1-C_6)$alkyloxy or $(C_1-C_6)$alkyloxy substituted, valency permitting, by one to five F.

14. A compound according to claim 1 wherein $R^6$ is a group selected from $CH_3$, $C_2H_5$, $CF_3$, —$OCH_3$, —$OC_2H_5$ or —$OCF_3$.

15. A pharmaceutical composition comprising a compound of formula (I) or a pharmaceutically acceptable salt thereof together, as defined in claim 1, with one or more pharmaceutically acceptable excipients.

16. A pharmaceutical composition according to claim 15 including one or more additional therapeutic agents.

* * * * *